(12) United States Patent
Chien et al.

(10) Patent No.: US 7,871,625 B2
(45) Date of Patent: Jan. 18, 2011

(54) HCV MULTIPLE EPITOPE FUSION ANTIGENS WITH MODIFIED PROTEOLYTIC CLEAVAGE SITES AND USES THEREOF

(75) Inventors: David Chien, Alamo, CA (US); Doris Coit, Petaluma, CA (US); Carlos George-Nascimento, Walnut Creek, CA (US); Sansan Lin, Albany, CA (US); Angelica Medina-Selby, San Francisco, CA (US); Laura Tandeske, San Leandro, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 182 days.

(21) Appl. No.: 11/661,577

(22) PCT Filed: Aug. 26, 2005

(86) PCT No.: PCT/US2005/030324

§ 371 (c)(1),
(2), (4) Date: Mar. 17, 2008

(87) PCT Pub. No.: WO2006/033768

PCT Pub. Date: Mar. 30, 2006

(65) Prior Publication Data

US 2008/0299544 A1    Dec. 4, 2008

Related U.S. Application Data

(60) Provisional application No. 60/604,858, filed on Aug. 27, 2004, provisional application No. 60/618,390, filed on Oct. 12, 2004, provisional application No. 60/621,502, filed on Oct. 22, 2004, provisional application No. 60/621,790, filed on Oct. 25, 2004.

(51) Int. Cl.
*A61K 39/00* (2006.01)
*C12N 15/00* (2006.01)

(52) U.S. Cl. .............. 424/189.1; 424/201.1; 424/228.1; 435/69.1

(58) Field of Classification Search .............. 424/228.1, 424/109.1
See application file for complete search history.

(56) References Cited

U.S. PATENT DOCUMENTS

| | | |
|---|---|---|
| 5,843,752 A | 12/1998 | Dasmahapatra et al. |
| 6,333,186 B1 | 12/2001 | Wittekind et al. |
| 6,428,792 B1 | 8/2002 | Valenzuela et al. |
| 6,514,731 B1 | 2/2003 | Valenzuela et al. |
| 6,630,298 B2 | 10/2003 | Chien et al. |
| 6,632,601 B2 | 10/2003 | Chien et al. |
| 6,797,809 B2 | 9/2004 | Chien et al. |
| 6,800,456 B2 | 10/2004 | Wittekind et al. |
| 6,986,892 B1 | 1/2006 | Coit et al. |
| 7,056,658 B2 | 6/2006 | Valenzuela et al. |
| 7,108,967 B2 | 9/2006 | Chien et al. |
| 7,166,426 B2 | 1/2007 | Arcangel et al. |
| 7,241,879 B2 * | 7/2007 | Chien et al. ................ 536/23.4 |
| 7,319,144 B2 | 1/2008 | Chien et al. |
| 7,449,566 B2 | 11/2008 | Coit et al. |
| 7,491,808 B2 | 2/2009 | Chien et al. |
| 2005/0074465 A1 | 4/2005 | Houghton |

FOREIGN PATENT DOCUMENTS

| | | |
|---|---|---|
| WO | WO 01/96870 A2 | 12/2001 |
| WO | WO 2004/005473 A2 | 1/2004 |
| WO | WO 2004/021871 | 3/2004 |

OTHER PUBLICATIONS

Trambas et al. Blood, Aug. 1, 2005, vol. 106, No. 3, pp. 932-937.*
Anglister et al. FASEB Journal 1993, vol. 7, pp. 1156-1162.*
Chien, et al., "Use Of A Novel Hepatitis C Virus (HCV) Major-Epitope Chimeric Polypeptide For Diagnosis Of HCV Infection," *J Clin Microbiol* 37(5) :1393-1397 (1999).
Written Opinion of the International Searching Authority from related WO Patent application No. PCT/US05/30324, 4 pages, mailed on Jul. 7, 2008.
Supplementary European Search Report for 05814007.0.

* cited by examiner

*Primary Examiner*—Bao Li
(74) *Attorney, Agent, or Firm*—Mark Seka; Roberta Robins

(57) ABSTRACT

Modified HCV multiple epitope fusion antigens (MEFAs) are described. The proteins include modified sequences such that proteolytic cleavage of the MEFAs by HCV NS3 protease is inhibited. HCV immunoassays including the modified MEFAs are also described.

17 Claims, 33 Drawing Sheets

```
  1                                          10
  M   A   T   K   A   V   C   V   L   K   G   D   G   P   V
ATG GCT ACA AAG GCT GTT TGT GTT TTG AAG GGT GAC GGC CCA GTT 20                                 30
  Q   G   I   I   N   F   E   Q   K   E   S   N   G   P   V
CAA GGT ATT ATT AAC TTC GAG CAG AAG GAA AGT AAT GGA CCA GTG

40
  K   V   W   G   S   I   K   G   L   T   E   G   L   H   G
AAG GTG TGG GGA AGC ATT AAA GGA CTG ACT GAA GGC CTG CAT GGA 50                                 60
  F   H   V   H   E   F   G   D   N   T   A   G   C   T   S
TTC CAT GTT CAT GAG TTT GGA GAT AAT ACA GCA GGC TGT ACC AGT

70
  A   G   P   H   F   N   P   L   S   R   K   H   G   G   P
GCA GGT CCT CAC TTT AAT CCT CTA TCC AGA AAA CAC GGT GGG CCA 80                                 90
  K   D   E   E   R   H   V   G   D   L   G   N   V   T   A
AAG GAT GAA GAG AGG CAT GTT GGA GAC TTG GGC AAT GTG ACT GCT

100
  D   K   D   G   V   A   D   V   S   I   E   D   S   V   I
GAC AAA GAT GGT GTG GCC GAT GTG TCT ATT GAA GAT TCT GTG ATC 110                                120
  S   L   S   G   D   H   C   I   I   G   R   T   L   V   V
TCA CTC TCA GGA GAC CAT TGC ATC ATT GGC CGC ACA CTG GTG GTC

130
  H   E   K   A   D   D   L   G   K   G   G   N   E   E   S
CAT GAA AAA GCA GAT GAC TTG GGC AAA GGT GGA AAT GAA GAA AGT 140                                150
  T   K   T   G   N   A   G   S   R   L   A   C   G   V   I
ACA AAG ACA GGA AAC GCT GGA AGT CGT TTG GCT TGT GGT GTA ATT

160
  G   I   A   Q   N   L   N   S   G   C   N   C   S   I   Y
GGG ATC GCC CAG AAT TTG AAT TCT GGT TGC AAT TGC TCT ATC TAT 170                                180
  P   G   H   I   T   G   H   R   M   A   W   K   L   G   S
CCC GGC CAT ATA ACG GGT CAC CGC ATG GCA TGG AAG CTT GGT TCC

190
  A   A   R   T   T   S   G   F   V   S   L   F   A   P   G
GCC GCC AGA ACT ACC TCG GGC TTT GTC TCC TTG TTC GCC CCA GGT
```

FIG. 5A

```
            200                                              210
 A   K   Q   N   E   T   H   V   T   G   G   A   A   A   R
GCC AAA CAA AAC GAA ACT CAC GTC ACG GGA GGC GCA GCC GCC CGA

220
 T   T   S   G   L   T   S   L   F   S   P   G   A   S   Q
ACT ACG TCT GGG TTG ACC TCT TTG TTC TCC CCA GGT GCC AGC CAA 230                                     240
 N   I   Q   L   I   V   D   F   I   P   V   E   N   L   E
AAC ATT CAA TTG ATT GTC GAC TTT ATC CCT GTG GAG AAC CTA GAG

250
 T   T   M   R   S   P   V   F   T   D   N   S   S   P   P
ACA ACC ATG CGA TCT CCG GTG TTC ACG GAT AAC TCC TCT CCA CCA 260                                         270
 V   V   P   Q   S   F   Q   V   A   H   L   H   A   P   T
GTA GTG CCC CAG AGC TTC CAG GTG GCT CAC CTC CAT GCT CCC ACA

280
 G   S   G   K   S   T   K   V   P   A   A   Y   A   A   Q
GGC AGC GGC AAA AGC ACC AAG GTC CCG GCT GCA TAT GCA GCT CAG 290                                         300
 G   Y   K   V   L   V   L   N   P   S   V   A   A   T   L
GGC TAT AAG GTG CTA GTA CTC AAC CCC TCT GTT GCT GCA ACA CTG

310
 G   F   G   A   Y   M   S   K   A   H   G   I   D   P   N
GGC TTT GGT GCT TAC ATG TCC AAG GCT CAT GGG ATC GAT CCT AAC 320                                         330
 I   R   T   G   V   R   T   I   T   T   G   S   P   I   T
ATC AGG ACC GGG GTG AGA ACA ATT ACC ACT GGC AGC CCC ATC ACG

340
 Y   S   T   Y   G   K   F   L   A   D   G   G   C   S   G
TAC TCC ACC TAC GGC AAG TTC CTT GCC GAC GGC GGG TGC TCG GGG 350                                         360
 G   A   Y   D   I   I   I   C   D   E   C   H   S   T   D
GGC GCT TAT GAC ATA ATA ATT TGT GAC GAG TGC CAC TCC ACG GAT

370
 A   T   S   I   L   G   I   G   T   V   L   D   Q   A   E
GCC ACA TCC ATC TTG GGC ATT GGC ACT GTC CTT GAC CAA GCA GAG 380                                         390
 T   A   G   A   R   L   V   V   L   A   T   A   T   P   P
ACT GCG GGG GCG AGA CTG GTT GTG CTC GCC ACC GCC ACC CCT CCG
```

FIG. 5B

```
                                    400
G   S   V   T   V   P   H   P   N   I   E   E   V   A   L
GGC TCC GTC ACT GTG CCC CAT CCC AAC ATC GAG GAG GTT GCT CTG 410                                     420
S   T   T   G   E   I   P   F   Y   G   K   A   I   P   L
TCC ACC ACC GGA GAG ATC CCT TTT TAC GGC AAG GCT ATC CCC CTC

430
E   V   I   K   G   G   R   H   L   I   F   C   H   S   K
GAA GTA ATC AAG GGG GGG AGA CAT CTC ATC TTC TGT CAT TCA AAG 440                                 450
K   K   C   D   E   L   A   A   K   L   V   A   L   G   I
AAG AAG TGC GAC GAA CTC GCC GCA AAG CTG GTC GCA TTG GGC ATC

460
N   A   V   A   Y   Y   R   G   L   D   V   S   V   I   P
AAT GCC GTG GCC TAC TAC CGC GGT CTT GAC GTG TCC GTC ATC CCG 470                                     480
T   S   G   D   V   V   V   V   A   T   D   A   L   M   T
ACC AGC GGC GAT GTT GTC GTC GTG GCA ACC GAT GCC CTC ATG ACC

490
G   Y   T   G   D   F   D   S   V   I   D   C   N   T   C
GGC TAT ACC GGC GAC TTC GAC TCG GTG ATA GAC TGC AAT ACG TGT 500                                 510
V   T   Q   T   V   D   F   S   L   D   P   T   F   T   I
GTC ACC CAG ACA GTC GAT TTC AGC CTT GAC CCT ACC TTC ACC ATT

520
E   T   I   T   L   P   Q   D   A   V   S   R   T   Q   R
GAG ACA ATC ACG CTC CCC CAA GAT GCT GTC TCC CGC ACT CAA CGT 530                                 540
R   G   R   T   G   R   G   K   P   G   I   Y   R   F   V
CGG GGC AGG ACT GGC AGG GGG AAG CCA GGC ATC TAC AGA TTT GTG

550
A   P   G   E   R   P   S   G   M   F   D   S   S   V   L
GCA CCG GGG GAG CGC CCC TCC GGC ATG TTC GAC TCG TCC GTC CTC 560                                 570
C   E   C   Y   D   A   G   C   A   W   Y   E   L   T   P
TGT GAG TGC TAT GAC GCA GGC TGT GCT TGG TAT GAG CTC ACG CCC

580
A   E   T   T   V   R   L   R   A   Y   M   N   T   P   G
GCC GAG ACT ACA GTT AGG CTA CGA GCG TAC ATG AAC ACC CCG GGG
```

FIG. 5C

```
                590                                                600
     L   P   V   C   Q   D   H   L   E   F   W   E   G   V   F
    CTT CCC GTG TGC CAG GAC CAT CTT GAA TTT TGG GAG GGC GTC TTT

610
     T   G   L   T   H   I   D   A   H   F   L   S   Q   T   K
    ACA GGC CTC ACT CAT ATA GAT GCC CAC TTT CTA TCC CAG ACA AAG 620                                        630
     Q   S   G   E   N   L   P   Y   L   V   A   Y   Q   A   T
    CAG AGT GGG GAG AAC CTT CCT TAC CTG GTA GCG TAC CAA GCC ACC

640
     V   C   A   R   A   Q   A   P   P   P   S   W   D   Q   M
    GTG TGC GCT AGG GCT CAA GCC CCT CCC CCA TCG TGG GAC CAG ATG 650                                    660
     W   K   C   L   I   R   L   K   P   T   L   H   G   P   T
    TGG AAG TGT TTG ATT CGC CTC AAG CCC ACC CTC CAT GGG CCA ACA

670
     P   L   L   Y   R   L   G   A   V   Q   N   E   I   T   L
    CCC CTG CTA TAC AGA CTG GGC GCT GTT CAG AAT GAA ATC ACC CTG 680                                690
     T   H   P   V   T   K   Y   I   M   T   C   M   S   A   D
    ACG CAC CCA GTC ACC AAA TAC ATC ATG ACA TGC ATG TCG GCC GAC

700
     L   E   V   V   T   S   A   C   S   G   K   P   A   I   I
    CTG GAG GTC GTC ACG AGC GCA TGC TCC GGG AAG CCG GCA ATC ATA 710                            720
     P   D   R   E   V   L   Y   R   E   F   D   E   M   E   E
    CCT GAC AGG GAA GTC CTC TAC CGA GAG TTC GAT GAG ATG GAA GAG

730
     C   S   Q   H   L   P   Y   I   E   Q   G   M   M   L   A
    TGC TCT CAG CAC TTA CCG TAC ATC GAG CAA GGG ATG ATG CTC GCC 740                                        750
     E   Q   F   K   Q   K   A   L   G   L   S   R   G   G   K
    GAG CAG TTC AAG CAG AAG GCC CTC GGC CTC TCG CGA GGG GGC AAG

760
     P   A   I   V   P   D   K   E   V   L   Y   Q   Q   Y   D
    CCG GCA ATC GTT CCA GAC AAA GAG GTG TTG TAT CAA CAA TAC GAT 770                                    780
     E   M   E   E   C   S   Q   A   A   P   Y   I   E   Q   A
    GAG ATG GAA GAG TGC TCA CAA GCT GCC CCA TAT ATC GAA CAA GCT
```

FIG. 5D

```
                                              790
      Q    V    I    A    H    Q    F    K    E    K    V    L    G    L    I
      CAG  GTA  ATA  GCT  CAC  CAG  TTC  AAG  GAA  AAA  GTC  CTT  GGA  TTG  ATC 800                                              810
      D    N    D    Q    V    V    V    T    P    D    K    E    I    L    Y
      GAT  AAT  GAT  CAA  GTG  GTT  GTG  ACT  CCT  GAC  AAA  GAA  ATC  TTA  TAT

820
      E    A    F    D    E    M    E    E    C    A    S    K    A    A    L
      GAG  GCC  TTT  GAT  GAG  ATG  GAA  GAA  TGC  GCC  TCC  AAA  GCC  GCC  CTC 830                                         840
      I    E    E    G    Q    R    M    A    E    M    L    K    S    K    I
      ATT  GAG  GAA  GGG  CAG  CGG  ATG  GCG  GAG  ATG  CTC  AAG  TCT  AAG  ATA

850
      Q    G    L    L    G    I    L    R    R    H    V    G    P    G    E
      CAA  GGC  CTC  CTC  GGG  ATA  CTG  CGC  CGG  CAC  GTT  GGT  CCT  GGC  GAG 860                                    870
      G    A    V    Q    W    M    N    R    L    I    A    F    A    S    R
      GGG  GCA  GTG  CAG  TGG  ATG  AAC  CGG  CTG  ATA  GCC  TTC  GCC  TCC  AGA

880
      G    N    H    V    S    P    T    H    Y    V    P    S    R    S    R
      GGG  AAC  CAT  GTT  TCC  CCC  ACG  CAC  TAC  GTT  CCG  TCT  AGA  TCC  CGG 890                                    900
      R    F    A    Q    A    L    P    V    W    A    R    P    D    Y    N
      AGA  TTC  GCC  CAG  GCC  CTG  CCC  GTT  TGG  GCG  CGG  CCG  GAC  TAT  AAC

910
      P    P    L    V    E    T    W    K    K    P    D    Y    E    P    P
      CCC  CCG  CTA  GTG  GAG  ACG  TGG  AAA  AAG  CCC  GAC  TAC  GAA  CCA  CCT 920                                    930
      V    V    H    G    R    S    S    R    R    F    A    Q    A    L    P
      GTG  GTC  CAC  GGC  AGA  TCT  TCT  CGG  AGA  TTC  GCC  CAG  GCC  CTG  CCC

940
      V    W    A    R    P    D    Y    N    P    P    L    V    E    T    W
      GTT  TGG  GCG  CGG  CCG  GAC  TAT  AAC  CCC  CCG  CTA  GTG  GAG  ACG  TGG 950                                         960
      K    K    P    D    Y    E    P    P    V    V    H    G    R    K    T
      AAA  AAG  CCC  GAC  TAC  GAA  CCA  CCT  GTG  GTC  CAT  GGC  AGA  AAG  ACC

970
      K    R    N    T    N    R    R    P    Q    D    V    K    F    P    G
      AAA  CGT  AAC  ACC  AAC  CGG  CGG  CCG  CAG  GAC  GTC  AAG  TTC  CCG  GGT
```

FIG. 5E

```
                980                                                      990
   G   G   Q   I   V   G   R   R   G   P   P   I   P   K   A
   GGC GGT CAG ATC GTT GGT CGC AGG GGC CCT CCT ATC CCC AAG GCT

1000
   R   R   P   E   G   R   T   W   A   Q   P   G   Y   P   W
   CGT CGG CCC GAG GGC AGG ACC TGG GCT CAG CCC GGT TAC CCT TGG 1010                                                     1020
   P   L   Y   G   N   K   D   R   R   S   T   G   K   S   W
   CCC CTC TAT GGC AAT AAG GAC AGA CGG TCT ACA GGT AAG TCC TGG

1030
   G   K   P   G   Y   P   W   P   R   K   T   K   R   N   T
   GGT AAG CCA GGG TAC CCT TGG CCA AGA AAG ACC AAA CGT AAC ACC 1040                                             1050
   N   R   R   P   Q   D   V   K   F   P   G   G   G   Q   I
   AAC CGA CGG CCG CAG GAC GTC AAG TTC CCG GGT GGC GGT CAG ATC

1060
   V   G   R   R   G   P   P   I   P   K   A   R   R   P   E
   GTT GGT CGC AGG GGC CCT CCT ATC CCC AAG GCT CGT CGG CCC GAG 1070                                                 1080
   G   R   T   W   A   Q   P   G   Y   P   W   P   L   Y   G
   GGC AGG ACC TGG GCT CAG CCC GGT TAC CCT TGG CCC CTC TAT GGC

1090
   N   K   D   R   R   S   T   G   K   S   W   G   K   P   G
   AAT AAG GAC AGA CGG TCT ACC GGT AAG TCC TGG GGT AAG CCA GGG

1099
   Y   P   W   P
   TAT CCT TGG CCC
```

FIG. 5F

```
  1                                           10
  M   A   T   K   A   V   C   V   L   K   G   D   G   P   V
ATG GCT ACA AAG GCT GTT TGT GTT TTG AAG GGT GAC GGC CCA GTT 20                                          30
  Q   G   I   I   N   F   E   Q   K   E   S   N   G   P   V
CAA GGT ATT ATT AAC TTC GAG CAG AAG GAA AGT AAT GGA CCA GTG

40
  K   V   W   G   S   I   K   G   L   T   E   G   L   H   G
AAG GTG TGG GGA AGC ATT AAA GGA CTG ACT GAA GGC CTG CAT GGA 50                                          60
  F   H   V   H   E   F   G   D   N   T   A   G   C   T   S
TTC CAT GTT CAT GAG TTT GGA GAT AAT ACA GCA GGC TGT ACC AGT

70
  A   G   P   H   F   N   P   L   S   R   K   H   G   G   P
GCA GGT CCT CAC TTT AAT CCT CTA TCC AGA AAA CAC GGT GGG CCA 80                                          90
  K   D   E   E   R   H   V   G   D   L   G   N   V   T   A
AAG GAT GAA GAG AGG CAT GTT GGA GAC TTG GGC AAT GTG ACT GCT

100
  D   K   D   G   V   A   D   V   S   I   E   D   S   V   I
GAC AAA GAT GGT GTG GCC GAT GTG TCT ATT GAA GAT TCT GTG ATC 110                                         120
  S   L   S   G   D   H   C   I   I   G   R   T   L   V   V
TCA CTC TCA GGA GAC CAT TGC ATC ATT GGC CGC ACA CTG GTG GTC

130
  H   E   K   A   D   D   L   G   K   G   N   E   E   S
CAT GAA AAA GCA GAT GAC TTG GGC AAA GGT GGA AAT GAA GAA AGT 140                                         150
  T   K   T   G   N   A   G   S   R   L   A   C   G   V   I
ACA AAG ACA GGA AAC GCT GGA AGT CGT TTG GCT TGT GGT GTA ATT

160
  G   I   A   Q   N   L   N   S   G   C   N   C   S   I   Y
GGG ATC GCC CAG AAT TTG AAT TCT GGT TGC AAT TGC TCT ATC TAT 170                                         180
  P   G   H   I   T   G   H   R   M   A   W   K   L   G   S
CCC GGC CAT ATA ACG GGT CAC CGC ATG GCA TGG AAG CTT GGT TCC

190
  A   A   R   T   T   S   G   F   V   S   L   F   A   P   G
GCC GCC AGA ACT ACC TCG GGC TTT GTC TCC TTG TTC GCC CCA GGT
```

FIG. 9A

```
            200                                           210
 A   K   Q   N   E   T   H   V   T   G   G   A   A   A   R
GCC AAA CAA AAC GAA ACT CAC GTC ACG GGA GGC GCA GCC GCC CGA

220
 T   T   S   G   L   T   S   L   F   S   P   G   A   S   Q
ACT ACG TCT GGG TTG ACC TCT TTG TTC TCC CCA GGT GCC AGC CAA 230                                           240
 N   I   Q   L   I   V   D   F   I   P   V   E   N   L   E
AAC ATT CAA TTG ATT GTC GAC TTT ATC CCT GTG GAG AAC CTA GAG

250
 T   T   M   R   S   P   V   F   T   D   N   S   P   P
ACA ACC ATG CGA TCT CCG GTG TTC ACG GAT AAC TCC TCT CCA CCA 260                                   270
 V   V   P   Q   S   F   Q   V   A   H   L   H   A   P   T
GTA GTG CCC CAG AGC TTC CAG GTG GCT CAC CTC CAT GCT CCC ACA

280
 G   S   G   K   S   T   K   V   P   A   A   Y   A   A   Q
GGC AGC GGC AAA AGC ACC AAG GTC CCG GCT GCA TAT GCA GCT CAG 290                              300
 G   Y   K   V   L   V   L   N   P   S   V   A   A   T   L
GGC TAT AAG GTG CTA GTA CTC AAC CCC TCT GTT GCT GCA ACA CTG

310
 G   F   G   A   Y   M   S   K   A   H   G   I   D   P   N
GGC TTT GGT GCT TAC ATG TCC AAG GCT CAT GGG ATC GAT CCT AAC 320                          330
 I   R   T   G   V   R   T   I   T   T   G   S   P   I   T
ATC AGG ACC GGG GTG AGA ACA ATT ACC ACT GGC AGC CCC ATC ACG

340
 Y   S   T   Y   G   K   F   L   A   D   G   G   C   S   G
TAC TCC ACC TAC GGC AAG TTC CTT GCC GAC GGC GGG TGC TCG GGG 350                      360
 G   A   Y   D   I   I   I   C   D   E   C   H   S   T   D
GGC GCT TAT GAC ATA ATA ATT TGT GAC GAG TGC CAC TCC ACG GAT

370
 A   T   S   I   L   G   I   G   T   V   L   D   Q   A   E
GCC ACA TCC ATC TTG GGC ATT GGC ACT GTC CTT GAC CAA GCA GAG 380                  390
 T   A   G   A   R   L   V   V   L   A   T   A   T   P   P
ACT GCG GGG GCG AGA CTG GTT GTG CTC GCC ACC GCC ACC CCT CCG
```

FIG. 9B

```
                                       400
     G    S    V    T    V    P    H    P    N    I    E    E    V    A    L
    GGC  TCC  GTC  ACT  GTG  CCC  CAT  CCC  AAC  ATC  GAG  GAG  GTT  GCT  CTG 410                                          420
     S    T    T    G    E    I    P    F    Y    G    K    A    I    P    L
    TCC  ACC  ACC  GGA  GAG  ATC  CCT  TTT  TAC  GGC  AAG  GCT  ATC  CCC  CTC

430
     E    V    I    K    G    G    R    H    L    I    F    C    H    S    K
    GAA  GTA  ATC  AAG  GGG  GGG  AGA  CAT  CTC  ATC  TTC  TGT  CAT  TCA  AAG 440                                          450
     K    K    C    D    E    L    A    A    K    L    V    A    L    G    I
    AAG  AAG  TGC  GAC  GAA  CTC  GCC  GCA  AAG  CTG  GTC  GCA  TTG  GGC  ATC

460
     N    A    V    A    Y    Y    R    G    L    D    V    S    V    I    P
    AAT  GCC  GTG  GCC  TAC  TAC  CGC  GGT  CTT  GAC  GTG  TCC  GTC  ATC  CCG 470                                          480
     L    P    G    D    V    V    V    V    A    T    D    A    L    M    T
    CTG  CCC  GGC  GAT  GTT  GTC  GTC  GTG  GCA  ACC  GAT  GCC  CTC  ATG  ACC

490
     G    Y    T    G    D    F    D    S    V    I    D    C    L    P    C
    GGC  TAT  ACC  GGC  GAC  TTC  GAC  TCG  GTG  ATA  GAC  TGC  CTG  CCC  TGT 500                                          510
     V    T    Q    T    V    D    F    S    L    D    P    T    F    T    I
    GTC  ACC  CAG  ACA  GTC  GAT  TTC  AGC  CTT  GAC  CCT  ACC  TTC  ACC  ATT

520
     E    T    I    T    L    P    Q    D    A    V    S    R    T    Q    R
    GAG  ACA  ATC  ACG  CTC  CCC  CAA  GAT  GCT  GTC  TCC  CGC  ACT  CAA  CGT 530                                          540
     R    G    R    T    G    R    G    K    P    G    I    Y    R    F    V
    CGG  GGC  AGG  ACT  GGC  AGG  GGG  AAG  CCA  GGC  ATC  TAC  AGA  TTT  GTG

550
     A    P    G    E    R    P    S    G    M    F    D    S    S    V    L
    GCA  CCG  GGG  GAG  CGC  CCC  TCC  GGC  ATG  TTC  GAC  TCG  TCC  GTC  CTC 560                                          570
     C    E    C    Y    D    A    G    C    A    W    Y    E    L    T    P
    TGT  GAG  TGC  TAT  GAC  GCA  GGC  TGT  GCT  TGG  TAT  GAG  CTC  ACG  CCC

580
     A    E    T    T    V    R    L    R    A    Y    M    N    T    P    G
    GCC  GAG  ACT  ACA  GTT  AGG  CTA  CGA  GCG  TAC  ATG  AAC  ACC  CCG  GGG
```

FIG. 9C

```
                  590                                            600
    L   P   V   C   Q   D   H   L   E   F   W   E   G   V   F
    CTT CCC GTG TGC CAG GAC CAT CTT GAA TTT TGG GAG GGC GTC TTT

610
    T   G   L   T   H   I   D   A   H   F   L   S   Q   T   K
    ACA GGC CTC ACT CAT ATA GAT GCC CAC TTT CTA TCC CAG ACA AAG 620                                            630
    Q   S   G   E   N   L   P   Y   L   V   A   Y   Q   A   T
    CAG AGT GGG GAG AAC CTT CCT TAC CTG GTA GCG TAC CAA GCC ACC

640
    V   C   A   R   A   Q   A   P   P   P   S   W   D   Q   M
    GTG TGC GCT AGG GCT CAA GCC CCT CCC CCA TCG TGG GAC CAG ATG 650                                        660
    W   K   C   L   I   R   L   K   P   T   L   H   G   P   T
    TGG AAG TGT TTG ATT CGC CTC AAG CCC ACC CTC CAT GGG CCA ACA

670
    P   L   L   Y   R   L   G   A   V   Q   N   E   I   T   L
    CCC CTG CTA TAC AGA CTG GGC GCT GTT CAG AAT GAA ATC ACC CTG 680                                    690
    T   H   P   V   T   K   Y   I   M   T   C   M   S   A   D
    ACG CAC CCA GTC ACC AAA TAC ATC ATG ACA TGC ATG TCG GCC GAC

700
    L   E   V   V   L   P   A   C   S   G   K   P   A   I   I
    CTG GAG GTC GTC CTG CCC GCA TGC TCC GGG AAG CCG GCA ATC ATA 710                                720
    P   D   R   E   V   L   Y   R   E   F   D   E   M   E   E
    CCT GAC AGG GAA GTC CTC TAC CGA GAG TTC GAT GAG ATG GAA GAG

730
    P   I   Q   H   L   P   Y   I   E   Q   G   M   M   L   A
    CCC ATT CAG CAC TTA CCG TAC ATC GAG CAA GGG ATG ATG CTC GCC 740                            750
    E   Q   F   K   Q   K   A   L   G   L   S   R   G   G   K
    GAG CAG TTC AAG CAG AAG GCC CTC GGC CTC TCG CGA GGG GGC AAG

760
    P   A   I   V   P   D   K   E   V   L   Y   Q   Q   Y   D
    CCG GCA ATC GTT CCA GAC AAA GAG GTG TTG TAT CAA CAA TAC GAT 770                        780
    E   M   E   E   P   I   Q   A   A   P   Y   I   E   Q   A
    GAG ATG GAA GAG CCT ATA CAA GCT GCC CCA TAT ATC GAA CAA GCT
```

FIG. 9D

```
                                        790
  Q   V   I   A   H   Q   F   K   E   K   V   L   G   L   I
 CAG GTA ATA GCT CAC CAG TTC AAG GAA AAA GTC CTT GGA TTG ATC 800                                 810
  D   N   D   Q   V   V   V   T   P   D   K   E   I   L   Y
 GAT AAT GAT CAA GTG GTT GTG ACT CCT GAC AAA GAA ATC TTA TAT

820
  E   A   F   D   E   M   E   E   P   I   S   K   A   A   L
 GAG GCC TTT GAT GAG ATG GAA GAA CCA ATC TCC AAA GCC GCC CTC 830                                     840
  I   E   E   G   Q   R   M   A   E   M   L   K   S   K   I
 ATT GAG GAA GGG CAG CGG ATG GCG GAG ATG CTC AAG TCT AAG ATA

850
  Q   G   L   L   G   I   L   R   H   V   G   P   G   E
 CAA GGC CTC CTC GGG ATA CTG CGC CGG CAC GTT GGT CCT GGC GAG 860                                     870
  G   A   V   Q   W   M   N   R   L   I   A   F   A   S   R
 GGG GCA GTG CAG TGG ATG AAC CGG CTG ATA GCC TTC GCC TCC AGA

880
  G   N   H   V   S   P   T   H   Y   V   P   S   R   S   R
 GGG AAC CAT GTT TCC CCC ACG CAC TAC GTT CCG TCT AGA TCC CGG 890                                     900
  R   F   A   Q   A   L   P   V   W   A   R   P   D   Y   N
 AGA TTC GCC CAG GCC CTG CCC GTT TGG GCG CGG CCG GAC TAT AAC

910
  P   P   L   V   E   T   W   K   K   P   D   Y   E   P   P
 CCC CCG CTA GTG GAG ACG TGG AAA AAG CCC GAC TAC GAA CCA CCT 920                                     930
  V   V   H   G   R   S   S   R   R   F   A   Q   A   L   P
 GTG GTC CAC GGC AGA TCT TCT CGG AGA TTC GCC CAG GCC CTG CCC

940
  V   W   A   R   P   D   Y   N   P   P   L   V   E   T   W
 GTT TGG GCG CGG CCG GAC TAT AAC CCC CCG CTA GTG GAG ACG TGG 950                                     960
  K   K   P   D   Y   E   P   P   V   V   H   G   R   K   T
 AAA AAG CCC GAC TAC GAA CCA CCT GTG GTC CAT GGC AGA AAG ACC

970
  K   R   N   T   N   R   R   P   Q   D   V   K   F   P   G
 AAA CGT AAC ACC AAC CGG CGG CCG CAG GAC GTC AAG TTC CCG GGT
```

FIG. 9E

```
                        980                                              990
     G   G   Q   I   V   G   R   R   G   P   P   I   P   K   A
    GGC GGT CAG ATC GTT GGT CGC AGG GGC CCT CCT ATC CCC AAG GCT

1000
     R   R   P   E   G   R   T   W   A   Q   P   G   Y   P   W
    CGT CGG CCC GAG GGC AGG ACC TGG GCT CAG CCC GGT TAC CCT TGG 1010                                         1020
     P   L   Y   G   N   K   D   R   R   S   T   G   K   S   W
    CCC CTC TAT GGC AAT AAG GAC AGA CGG TCT ACA GGT AAG TCC TGG

1030
     G   K   P   G   Y   P   W   P   R   K   T   K   R   N   T
    GGT AAG CCA GGG TAC CCT TGG CCA AGA AAG ACC AAA CGT AAC ACC 1040                                     1050
     N   R   R   P   Q   D   V   K   F   P   G   G   G   Q   I
    AAC CGA CGG CCG CAG GAC GTC AAG TTC CCG GGT GGC GGT CAG ATC

1060
     V   G   R   R   G   P   P   I   P   K   A   R   R   P   E
    GTT GGT CGC AGG GGC CCT CCT ATC CCC AAG GCT CGT CGG CCC GAG 1070                                 1080
     G   R   T   W   A   Q   P   G   Y   P   W   P   L   Y   G
    GGC AGG ACC TGG GCT CAG CCC GGT TAC CCT TGG CCC CTC TAT GGC

1090
     N   K   D   R   R   S   T   G   K   S   W   G   K   P   G
    AAT AAG GAC AGA CGG TCT ACC GGT AAG TCC TGG GGT AAG CCA GGG

1099
     Y   P   W   P
    TAT CCT TGG CCC
```

FIG. 9F

```
              1                                                    50
mefa7.1aa   MATKAVCVLK GDGPVQGIIN FEQKESNGPV KVWGSIKGLT EGLHGFHVHE
mefa7.2aa   MATKAVCVLK GDGPVQGIIN FEQKESNGPV KVWGSIKGLT EGLHGFHVHE 51                                                   100
mefa7.1aa   FGDNTAGCTS AGPHFNPLSR KHGGPKDEER HVGDLGNVTA DKDGVADVSI
mefa7.2aa   FGDNTAGCTS AGPHFNPLSR KHGGPKDEER HVGDLGNVTA DKDGVADVSI 101                                                  150
mefa7.1aa   EDSVISLSGD HCIIGRTLVV HEKADDLGKG GNEESTKTGN AGSRLACGVI
mefa7.2aa   EDSVISLSGD HCIIGRTLVV HEKADDLGKG GNEESTKTGN AGSRLACGVI 151                                                  200
mefa7.1aa   GIAQNLNSGC NCSIYPGHIT GHRMAWKLGS AARTTSGFVS LFAPGAKQNE
mefa7.2aa   GIAQNLNSGC NCSIYPGHIT GHRMAWKLGS AARTTSGFVS LFAPGAKQNE 201                                                  250
mefa7.1aa   THVTGGAAAR TTSGLTSLFS PGASQNIQLI VDFIPVENLE TTMRSPVFTD
mefa7.2aa   THVTGGAAAR TTSGLTSLFS PGASQNIQLI VDFIPVENLE TTMRSPVFTD 251                                                  300
mefa7.1aa   NSSPPVVPQS FQVAHLHAPT GSGKSTKVPA AYAAQGYKVL VLNPSVAATL
mefa7.2aa   NSSPPVVPQS FQVAHLHAPT GSGKSTKVPA AYAAQGYKVL VLNPSVAATL 301                                                  350
mefa7.1aa   GFGAYMSKAH GIDPNIRTGV RTITTGSPIT YSTYGKFLAD GGCSGGAYDI
mefa7.2aa   GFGAYMSKAH GIDPNIRTGV RTITTGSPIT YSTYGKFLAD GGCSGGAYDI 351                                                  400
mefa7.1aa   IICDECHSTD ATSILGIGTV LDQAETAGAR LVVLATATPP GSVTVPHPNI
mefa7.2aa   IICDECHSTD ATSILGIGTV LDQAETAGAR LVVLATATPP GSVTVPHPNI 401                                                  450
mefa7.1aa   EEVALSTTGE IPFYGKAIPL EVIKGGRHLI FCHSKKKCDE LAAKLVALGI
mefa7.2aa   EEVALSTTGE IPFYGKAIPL EVIKGGRHLI FCHSKKKCDE LAAKLVALGI 451                                                  500
mefa7.1aa   NAVAYYRGLD VSVIPTSGDV VVVATDALMT GYTGDFDSVI DCNTCVTQTV
mefa7.2aa   NAVAYYRGLD VSVIPLPGDV VVVATDALMT GYTGDFDSVI DCLPCVTQTV 501                                                  550
mefa7.1aa   DFSLDPTFTI ETITLPQDAV SRTQRRGRTG RGKPGIYRFV APGERPSGMF
mefa7.2aa   DFSLDPTFTI ETITLPQDAV SRTQRRGRTG RGKPGIYRFV APGERPSGMF 551                                                  600
mefa7.1aa   DSSVLCECYD AGCAWYELTP AETTVRLRAY MNTPGLPVCQ DHLEFWEGVF
mefa7.2aa   DSSVLCECYD AGCAWYELTP AETTVRLRAY MNTPGLPVCQ DHLEFWEGVF 601                                                  650
mefa7.1aa   TGLTHIDAHF LSQTKQSGEN LPYLVAYQAT VCARAQAPPP SWDQMWKCLI
mefa7.2aa   TGLTHIDAHF LSQTKQSGEN LPYLVAYQAT VCARAQAPPP SWDQMWKCLI
```

FIG. 10A

```
              651                                                              700
mefa7.1aa    RLKPTLHGPT  PLLYRLGAVQ  NEITLTHPVT  KYIMTCMSAD  LEVVTSACSG
mefa7.2aa    RLKPTLHGPT  PLLYRLGAVQ  NEITLTHPVT  KYIMTCMSAD  LEVVLPACSG 701                                                              750
mefa7.1aa    KPAIIPDREV  LYREFDEMEE  CSQHLPYIEQ  GMMLAEQFKQ  KALGLSRGGK
mefa7.2aa    KPAIIPDREV  LYREFDEMEE  PIQHLPYIEQ  GMMLAEQFKQ  KALGLSRGGK 751                                                              800
mefa7.1aa    PAIVPDKEVL  YQQYDEMEEC  SQAAPYIEQA  QVIAHQFKEK  VLGLIDNDQV
mefa7.2aa    PAIVPDKEVL  YQQYDEMEEP  IQAAPYIEQA  QVIAHQFKEK  VLGLIDNDQV 801                                                              850
mefa7.1aa    VVTPDKEILY  EAFDEMEECA  SKAALIEEGQ  RMAEMLKSKI  QGLLGILRRH
mefa7.2aa    VVTPDKEILY  EAFDEMEEPI  SKAALIEEGQ  RMAEMLKSKI  QGLLGILRRH 851                                                              900
mefa7.1aa    VGPGEGAVQW  MNRLIAFASR  GNHVSPTHYV  PSRSRRFAQA  LPVWARPDYN
mefa7.2aa    VGPGEGAVQW  MNRLIAFASR  GNHVSPTHYV  PSRSRRFAQA  LPVWARPDYN 901                                                              950
mefa7.1aa    PPLVETWKKP  DYEPPVVHGR  SSRRFAQALP  VWARPDYNPP  LVETWKKPDY
mefa7.2aa    PPLVETWKKP  DYEPPVVHGR  SSRRFAQALP  VWARPDYNPP  LVETWKKPDY 951                                                             1000
mefa7.1aa    EPPVVHGRKT  KRNTNRRPQD  VKFPGGGQIV  GRRGPPIPKA  RRPEGRTWAQ
mefa7.2aa    EPPVVHGRKT  KRNTNRRPQD  VKFPGGGQIV  GRRGPPIPKA  RRPEGRTWAQ 1001                                                             1050
mefa7.1aa    PGYPWPLYGN  KDRRSTGKSW  GKPGYPWPRK  TKRNTNRRPQ  DVKFPGGGQI
mefa7.2aa    PGYPWPLYGN  KDRRSTGKSW  GKPGYPWPRK  TKRNTNRRPQ  DVKFPGGGQI 1051                                                             1100
mefa7.1aa    VGRRGPPIPK  ARRPEGRTWA  QPGYPWPLYG  NKDRRSTGKS  WGKPGYPWP.
mefa7.2aa    VGRRGPPIPK  ARRPEGRTWA  QPGYPWPLYG  NKDRRSTGKS  WGKPGYPWP.
```

FIG. 10B

MEFA-3 ANTIGEN

| hSOD-(1-154) | CORE | CORE | c33c | 5-1-1 type 1 | 5-1-1 type 3 | 5-1-1 type 2 | C-100 | C-100 | NS5 | NS5 |
|---|---|---|---|---|---|---|---|---|---|---|
| AMINO ACIDS | 10 - 53 | 10 - 53 | 1192 - 1457 | 1694 - 1735 | 1694 - 1735 | 1694 - 1735 | 1901 - 1940 | 1901 - 1940 | 2278 - 2310 | 2278 - 2310 |

FIG. 12A

MEFA-5 ANTIGEN

| hSOD-(1-154) | CORE | CORE | E1 | E2 | c33c | 5-1-1 type 1 | 5-1-1 type 3 | 5-1-1 type 2 | C-100 | NS5 |
|---|---|---|---|---|---|---|---|---|---|---|
| AMINO ACIDS | 10 - 53 | 10 - 53 | 303 - 320 | 405 - 444 | 1192 - 1457 | 1689 - 1735 | 1689 - 1735 | 1689 - 1735 | 1901 - 1940 | 2278 - 2313 |

FIG. 12B

MEFA-6 ANTIGEN

| hSOD-(1-154) | E1 | E2 | c33c | 5-1-1 type 1 | 5-1-1 type 3 | 5-1-1 type 2 | C-100 | NS5 | NS5 | CORE |
|---|---|---|---|---|---|---|---|---|---|---|
| AMINO ACIDS | 303 - 320 | 405 - 444 | 1192 - 1457 | 1689 - 1735 | 1689 - 1735 | 1689 - 1735 | 1901 - 1940 | 2278 - 2313 | 2278 - 2313 | 10 - 53 |

FIG. 12C

```
                              1                                              10
                              M    A    P    I    T    A    Y    A    Q    Q
                              ATG  GCG  CCC  ATC  ACG  GCG  TAC  GCC  CAG  CAG

20
T    R    G    L    L    G    C    I    I    T    S    L    T    G    R
ACA  AGG  GGC  CTC  CTA  GGG  TGC  ATA  ATC  ACC  AGC  CTA  ACT  GGC  CGG 30                                                  40
D    K    N    Q    V    E    G    E    V    Q    I    V    S    T    A
GAC  AAA  AAC  CAA  GTG  GAG  GGT  GAG  GTC  CAG  ATT  GTG  TCA  ACT  GCT

50
A    Q    T    F    L    A    T    G    I    N    G    V    C    W    T
GCC  CAA  ACC  TTC  CTG  GCA  ACG  TGC  ATC  AAT  GGG  GTG  TGC  TGG  ACT 60                                             70
V    Y    H    G    A    G    T    R    T    I    A    S    P    K    G
GTC  TAC  CAC  GGG  GCC  GGA  ACG  AGG  ACC  ATC  GCG  TCA  CCC  AAG  GGT

80
P    V    I    Q    M    Y    T    N    V    D    Q    D    L    V    G
CCT  GTC  ATC  CAG  ATG  TAT  ACC  AAT  GTA  GAC  CAA  GAC  CTT  GTG  GGC 90                                            100
W    P    A    P    Q    G    S    R    S    L    T    P    C    T    C
TGG  CCC  GCT  CCG  CAA  GGT  AGC  CGA  TCA  TTG  ACA  CCC  TGC  ACT  TGC

110
G    S    S    D    L    Y    L    V    T    R    H    A    D    V    I
GGC  TCC  TCG  GAC  CTT  TAC  CTG  GTC  ACG  AGG  CAC  GCC  GAT  GTC  ATT 120                                                130
P    V    R    R    R    G    D    S    R    G    S    L    L    S    P
CCC  GTG  CGC  CGG  CGG  GGT  GAT  AGC  AGG  GGC  AGC  CTG  CTG  TCG  CCC

140
R    P    I    S    Y    L    K    G    S    S    G    G    P    L    L
CGG  CCC  ATT  TCC  TAC  TTG  AAA  GGC  TCC  TCG  GGG  GGT  CCG  CTG  TTG 150                                                160
C    P    A    G    H    A    V    G    I    F    R    A    A    V    C
TGC  CCC  GCG  GGG  CAC  GCC  GTG  GGC  ATA  TTT  AGG  GCC  GCG  GTG  TGC

170
T    R    G    V    A    K    A    V    D    F    I    P    V    E    N
ACC  CGT  GGA  GTG  GCT  AAG  GCG  GTG  GAC  TTT  ATC  CCT  GTG  GAG  AAC 180                                                190
L    E    T    T    M    R    S    P    V    F    T    D    N    S    S
CTA  GAG  ACA  ACC  ATG  AGG  TCC  CCG  GTG  TTC  ACG  GAT  AAC  TCC  TCT
```

FIG. 13A

```
                                              200
    P   P   V   V   P   Q   S   F   Q   V   A   H   L   H   A
    CCA CCA GTA GTG CCC CAG AGC TTC CAG GTG GCT CAC CTC CAT GCT 210                                     220
    P   T   G   S   G   K   S   T   K   V   P   A   A   Y   A
    CCC ACA GGC AGC GGC AAA AGC ACC AAG GTC CCG GCT GCA TAT GCA

230
    A   Q   G   Y   K   V   L   V   L   N   P   S   V   A   A
    GCT CAG GGC TAT AAG GTG CTA GTA CTC AAC CCC TCT GTT GCT GCA 240                                     250
    T   L   G   F   G   A   Y   M   S   K   A   H   G   I   D
    ACA CTG GGC TTT GGT GCT TAC ATG TCC AAG GCT CAT GGG ATC GAT

260
    P   N   I   R   T   G   V   R   T   I   T   T   G   S   P
    CCT AAC ATC AGG ACC GGG GTG AGA ACA ATT ACC ACT GGC AGC CCC 270                                     280
    I   T   Y   S   T   Y   G   K   F   L   A   D   G   G   C
    ATC ACG TAC TCC ACC TAC GGC AAG TTC CTT GCC GAC GGC GGG TGC

290
    S   G   G   A   Y   D   I   I   I   C   D   E   C   H   S
    TCG GGG GGC GCT TAT GAC ATA ATA ATT TGT GAC GAG TGC CAC TCC 300                                     310
    T   D   A   T   S   I   L   G   I   G   T   V   L   D   Q
    ACG GAT GCC ACA TCC ATC TTG GGC ATT GGC ACT GTC CTT GAC CAA

320
    A   E   T   A   G   A   R   L   V   V   L   A   T   A   T
    GCA GAG ACT GCG GGG GCG AGA CTG GTT GTG CTC GCC ACC GCC ACC 330                                     340
    P   P   G   S   V   T   V   P   H   P   N   I   E   E   V
    CCT CCG GGC TCC GTC ACT GTG CCC CAT CCC AAC ATC GAG GAG GTT

350
    A   L   S   T   T   G   E   I   P   F   Y   G   K   A   I
    GCT CTG TCC ACC ACC GGA GAG ATC CCT TTT TAC GGC AAG GCT ATC 360                                     370
    P   L   E   V   I   K   G   G   R   H   L   I   F   C   H
    CCC CTC GAA GTA ATC AAG GGG GGA AGA CAT CTC ATC TTC TGT CAT

380
    S   K   K   K   C   D   E   L   A   A   K   L   V   A   L
    TCA AAG AAG AAG TGC GAC GAA CTC GCC GCA AAG CTG GTC GCA TTG
```

FIG. 13B

```
            390                                                400
 G   I   N   A   V   A   Y   Y   R   G   L   D   V   S   V
GGC ATC AAT GCC GTG GCC TAC TAC CGC GGT CTT GAC GTG TCC GTC

410
 I   P   P   I   G   D   V   V   V   A   T   D   A   L
ATC CCG CCC ATC GGC GAT GTT GTC GTC GTG GCA ACC GAT GCC CTC 420                                                430
 M   T   G   Y   T   G   D   F   D   S   V   I   D   C   N
ATG ACC GGC TAT ACG GGC GAC TTC GAC TCG GTG ATA GAC TGC AAT

440
 T   C   V   T   Q   T   V   D   F   S   L   D   P   T   F
ACG TGT GTC ACC CAG ACA GTC GAT TTC AGC CTT GAC CCT ACC TTC 450                                                460
 T   I   E   T   I   T   L   P   Q   D   A   V   S   R   T
ACC ATT GAG ACA ATC ACG CTC CCC CAA GAT GCT GTC TCC CGC ACT

470
 Q   R   R   G   R   T   G   R   G   K   P   G   I   Y   R
CAA CGT CGG GGC AGG ACT GGC AGG GGG AAG CCA GGC ATC TAC AGA 480                                                490
 F   V   A   P   G   E   R   P   S   G   M   F   D   S   S
TTT GTG GCA CCG GGG GAG CGC CCC TCC GGC ATG TTC GAC TCG TCC

500
 V   L   C   E   C   Y   D   A   G   C   A   W   Y   E   L
GTC CTC TGT GAG TGC TAT GAC GCA GGC TGT GCT TGG TAT GAG CTC 510                                                520
 T   P   A   E   T   T   V   R   L   R   A   Y   M   N   T
ACG CCC GCC GAG ACT ACA GTT AGG CTA CGA GCG TAC ATG AAC ACC

530
 P   G   L   P   V   C   Q   D   H   L   E   F   W   E   G
CCG GGG CTT CCC GTG TGC CAG GAC CAT CTT GAA TTT TGG GAG GGC 540                                                550
 V   F   T   G   L   T   H   I   D   A   H   F   L   S   Q
GTC TTT ACA GGC CTC ACT CAT ATA GAT GCC CAC TTT CTA TCC CAG

560
 T   K   Q   S   G   E   N   L   P   Y   L   V   A   Y   Q
ACA AAG CAG AGT GGG GAG AAC CTT CCT TAC CTG GTA GCG TAC CAA 570                                                580
 A   T   V   C   A   R   A   Q   A   P   P   P   S   W   D
GCC ACC GTG TGC GCT AGG GCT CAA GCC CCT CCC CCA TCG TGG GAC
```

FIG. 13C

```
                                                590
 Q    M    W    K    C    L    I    R    L    K    P    T    L    H    G
CAG  ATG  TGG  AAG  TGT  TTG  ATT  CGC  CTC  AAG  CCC  ACC  CTC  CAT  GGG 600                                              610
 P    T    P    L    L    Y    R    L    G    A    V    Q    N    E    I
CCA  ACA  CCC  CTG  CTA  TAC  AGA  CTG  GGC  GCT  GTT  CAG  AAT  GAA  ATC

620
 T    L    T    H    P    V    T    K    Y    I    M    T    C    M    S
ACC  CTG  ACG  CAC  CCA  GTC  ACC  AAA  TAC  ATC  ATG  ACA  TGC  ATG  TCG 630                                              640
 A    D    L    E    V    V    T    S    T    W    V    L    V    G    G
GCC  GAC  CTG  GAG  GTC  GTC  ACG  AGC  ACC  TGG  GTG  CTC  GTT  GGC  GGC

650
 V    L    A    A    L    A    A    Y    C    L    S    T    G    C    V
GTC  CTG  GCT  GCT  TTG  GCC  GCG  TAT  TGC  CTG  TCA  ACA  GGC  TGC  GTG 660                                              670
 V    I    V    G    R    V    V    L    S    G    K    P    A    I    I
GTC  ATA  GTG  GGC  AGG  GTC  GTC  TTG  TCC  GGG  AAG  CCG  GCA  ATC  ATA

680
 P    D    R    E    V    L    Y    R    E    F    D    E    M    E    E
CCT  GAC  AGG  GAA  GTC  CTC  TAC  CGA  GAG  TTC  GAT  GAG  ATG  GAA  GAG

686
 C
TGC
```

FIG. 13D

```
                        SEQUENCE LISTING

<160> NUMBER OF SEQ ID NOS: 7

<210> SEQ ID NO 1
<211> LENGTH: 3297
<212> TYPE: DNA
<213> ORGANISM: Artificial
<220> FEATURE:
<223> OTHER INFORMATION: MEFA 7.1

<400> SEQUENCE: 1
atggctacaa aggctgtttg tgttttgaag ggtgacggcc cagttcaagg tattattaac      60
ttcgagcaga aggaaagtaa tggaccagtg aaggtgtggg aagcattaa aggactgact      120 gaaggcctgc atggattcca tgttcatgag tttggagata atacagcagg ctgtaccagt      180
gcaggtcctc actttaatcc tctatccaga aaacacggtg ggccaaagga tgaagagagg      240
catgttggag acttgggcaa tgtgactgct gacaaagatg gtgtggccga tgtgtctatt      300
gaagattctg tgatctcact ctcaggagac cattgcatca ttggccgcac actggtggtc      360
catgaaaaag cagatgactt gggcaaaggt ggaaatgaag aaagtacaaa gacaggaaac      420
gctggaagtc gtttggcttg tggtgtaatt gggatcgccc agaatttgaa ttctggttgc      480
aattgctcta tctatcccgg ccatataacg ggtcaccgca tggcatggaa gcttggttcc      540
gccgccagaa ctacctcggg ctttgtctcc ttgttcgccc aggtgccaa acaaaacgaa      600 actcacgtca cgggaggcgc agccgcccga actacgtctg ggttgacctc tttgttctcc      660
ccaggtgcca gccaaaacat tcaattgatt gtcgacttta ccctgtgga gaacctagag      720 acaaccatgc gatctccggt gttcacggat aactcctctc caccagtagt gccccagagc      780
```

```
ttccaggtgg ctcacctcca tgctcccaca ggcagcggca aaagcaccaa ggtcccggct     840
gcatatgcag ctcagggcta taaggtgcta gtactcaacc cctctgttgc tgcaacactg     900
ggctttggtg cttacatgtc caaggctcat gggatcgatc ctaacatcag gaccggggtg     960
agaacaatta ccactggcag ccccatcacg tactccacct acggcaagtt ccttgccgac    1020
ggcgggtgct cggggggcgc ttatgacata taatttgtg acgagtgcca ctccacggat     1080
gccacatcca tcttgggcat tggcactgtc cttgaccaag cagagactgc gggggcgaga    1140
ctggttgtgc tcgccaccgc cacccctccg ggctccgtca ctgtgcccca tcccaacatc    1200
gaggaggttg ctctgtccac caccggagag atccctttt acggcaaggc tatccccctc     1260
gaagtaatca aggggggag acatctcatc ttctgtcatt caaagaagaa gtgcgacgaa     1320
ctcgccgcaa agctggtcgc attgggcatc aatgccgtgg cctactaccg cggtcttgac    1380
gtgtccgtca tcccgaccag cggcgatgtt gtcgtcgtgg caaccgatgc cctcatgacc    1440
ggctataccg gcgacttcga ctcggtgata gactgcaata cgtgtgtcac ccagacagtc    1500
gatttcagcc ttgaccctac cttcaccatt gagacaatca cgctccccca agatgctgtc    1560
tcccgcactc aacgtcgggg caggactggc aggggaagc caggcatcta cagatttgtg     1620
gcaccggggg agcgcccctc cggcatgttc gactcgtccg tcctctgtga gtgctatgac    1680
gcaggctgtg cttggtatga gctcacgccc gccgagacta cagttaggct acgagcgtac    1740
atgaacaccc cggggcttcc cgtgtgccag gaccatcttg aattttggga gggcgtcttt    1800
acaggcctca ctcatataga tgcccacttt ctatcccaga caaagcagag tggggagaac    1860
cttccttacc tggtagcgta ccaagccacc gtgtgcgcta gggctcaagc ccctccccca    1920
tcgtgggacc agatgtggaa gtgtttgatt cgcctcaagc ccaccctcca tgggccaaca    1980
cccctgctat acagactggg cgctgttcag aatgaaatca ccctgacgca cccagtcacc    2040
aaatacatca tgacatgcat gtcggccgac ctggaggtcg tcacgagcgc atgctccggg    2100
aagccggcaa tcatacctga cagggaagtc ctctaccgag agttcgatga gatggaagag    2160
tgctctcagc acttaccgta catcgagcaa gggatgatgc tcgccgagca gttcaagcag    2220
aaggccctcg gcctctcgcg agggggcaag ccggcaatcg ttccagacaa agaggtgttg    2280
tatcaacaat acgatgagat ggaagagtgc tcacaagctg ccccatatat cgaacaagct    2340
caggtaatag ctcaccagtt caaggaaaaa gtccttggat tgatcgataa tgatcaagtg    2400
gttgtgactc ctgacaaaga aatcttatat gaggcctttg atgagatgga agaatgcgcc    2460
tccaaagccg ccctcattga ggaagggcag cggatggcgg agatgctcaa gtctaagata    2520
caaggcctcc tcgggatact cgccggcac gttggtcctg cgagggggc agtgcagtgg      2580 atgaaccggc tgatagcctt cgcctccaga gggaaccatg tttcccccac gcactacgtt    2640
ccgtctagat cccggagatt cgcccaggcc ctgcccgttt gggcgcggcc ggactataac    2700
cccccgctag tggagacgtg gaaaagccc gactacgaac cacctgtggt ccacggcaga    2760
tcttctcgga gattcgccca ggccctgccc gtttgggcgc ggccggacta taaccccccg    2820
ctagtggaga cgtggaaaaa gcccgactac gaaccacctg tggtccatgg cagaaagacc    2880
aaacgtaaca ccaaccggcg gccgcaggac gtcaagttcc cgggtggcgg tcagatcgtt    2940
ggtcgcaggg gccctcctat ccccaaggct cgtcggcccg agggcaggac ctgggctcag    3000
cccggttacc cttggccct ctatggcaat aaggacagac ggtctacagg taagtcctgg    3060
ggtaagccag ggtacccttg gccaagaaag accaaacgta acaccaaccg acggccgcag    3120
gacgtcaagt tccgggtgg cggtcagatc gttggtcgca ggggccctcc tatccccaag     3180
```

-continued

```
gctcgtcggc ccgagggcag gacctgggct cagcccggtt acccttggcc cctctatggc    3240
aataaggaca gacggtctac cggtaagtcc tggggtaagc cagggtatcc ttggccc       3297
```

<210> SEQ ID NO 2
<211> LENGTH: 1099
<212> TYPE: PRT
<213> ORGANISM: Artificial
<220> FEATURE:
<223> OTHER INFORMATION: MEFA 7.1

<400> SEQUENCE: 2

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
        130                 135                 140

Leu Ala Cys Gly Val Ile Gly Ile Ala Gln Asn Leu Asn Ser Gly Cys
145                 150                 155                 160

Asn Cys Ser Ile Tyr Pro Gly His Ile Thr Gly His Arg Met Ala Trp
                165                 170                 175

Lys Leu Gly Ser Ala Ala Arg Thr Thr Ser Gly Phe Val Ser Leu Phe
            180                 185                 190

Ala Pro Gly Ala Lys Gln Asn Glu Thr His Val Thr Gly Gly Ala Ala
        195                 200                 205

Ala Arg Thr Thr Ser Gly Leu Thr Ser Leu Phe Ser Pro Gly Ala Ser
    210                 215                 220

Gln Asn Ile Gln Leu Ile Val Asp Phe Ile Pro Val Glu Asn Leu Glu
225                 230                 235                 240

Thr Thr Met Arg Ser Pro Val Phe Thr Asp Asn Ser Ser Pro Pro Val
                245                 250                 255

Val Pro Gln Ser Phe Gln Val Ala His Leu His Ala Pro Thr Gly Ser
            260                 265                 270

Gly Lys Ser Thr Lys Val Pro Ala Ala Tyr Ala Ala Gln Gly Tyr Lys
        275                 280                 285

Val Leu Val Leu Asn Pro Ser Val Ala Ala Thr Leu Gly Phe Gly Ala
    290                 295                 300

Tyr Met Ser Lys Ala His Gly Ile Asp Pro Asn Ile Arg Thr Gly Val
305                 310                 315                 320

Arg Thr Ile Thr Thr Gly Ser Pro Ile Thr Tyr Ser Thr Tyr Gly Lys
                325                 330                 335

Phe Leu Ala Asp Gly Gly Cys Ser Gly Gly Ala Tyr Asp Ile Ile Ile
            340                 345                 350
```

```
Cys Asp Glu Cys His Ser Thr Asp Ala Thr Ser Ile Leu Gly Ile Gly
        355                 360                 365

Thr Val Leu Asp Gln Ala Glu Thr Ala Gly Ala Arg Leu Val Val Leu
    370                 375                 380

Ala Thr Ala Thr Pro Pro Gly Ser Val Thr Val Pro His Pro Asn Ile
385                 390                 395                 400

Glu Glu Val Ala Leu Ser Thr Thr Gly Glu Ile Pro Phe Tyr Gly Lys
                405                 410                 415

Ala Ile Pro Leu Glu Val Ile Lys Gly Gly Arg His Leu Ile Phe Cys
            420                 425                 430

His Ser Lys Lys Lys Cys Asp Glu Leu Ala Ala Lys Leu Val Ala Leu
        435                 440                 445

Gly Ile Asn Ala Val Ala Tyr Tyr Arg Gly Leu Asp Val Ser Val Ile
    450                 455                 460

Pro Thr Ser Gly Asp Val Val Val Ala Thr Asp Ala Leu Met Thr
465                 470                 475                 480

Gly Tyr Thr Gly Asp Phe Asp Ser Val Ile Asp Cys Asn Thr Cys Val
                485                 490                 495

Thr Gln Thr Val Asp Phe Ser Leu Asp Pro Thr Phe Thr Ile Glu Thr
            500                 505                 510

Ile Thr Leu Pro Gln Asp Ala Val Ser Arg Thr Gln Arg Arg Gly Arg
        515                 520                 525

Thr Gly Arg Gly Lys Pro Gly Ile Tyr Arg Phe Val Ala Pro Gly Glu
    530                 535                 540

Arg Pro Ser Gly Met Phe Asp Ser Ser Val Leu Cys Glu Cys Tyr Asp
545                 550                 555                 560

Ala Gly Cys Ala Trp Tyr Glu Leu Thr Pro Ala Glu Thr Thr Val Arg
                565                 570                 575

Leu Arg Ala Tyr Met Asn Thr Pro Gly Leu Pro Val Cys Gln Asp His
            580                 585                 590

Leu Glu Phe Trp Glu Gly Val Phe Thr Gly Leu Thr His Ile Asp Ala
        595                 600                 605

His Phe Leu Ser Gln Thr Lys Gln Ser Gly Glu Asn Leu Pro Tyr Leu
    610                 615                 620

Val Ala Tyr Gln Ala Thr Val Cys Ala Arg Ala Gln Ala Pro Pro Pro
625                 630                 635                 640

Ser Trp Asp Gln Met Trp Lys Cys Leu Ile Arg Leu Lys Pro Thr Leu
                645                 650                 655

His Gly Pro Thr Pro Leu Leu Tyr Arg Leu Gly Ala Val Gln Asn Glu
            660                 665                 670

Ile Thr Leu Thr His Pro Val Thr Lys Tyr Ile Met Thr Cys Met Ser
        675                 680                 685

Ala Asp Leu Glu Val Val Thr Ser Ala Cys Ser Gly Lys Pro Ala Ile
    690                 695                 700

Ile Pro Asp Arg Glu Val Leu Tyr Arg Glu Phe Asp Glu Met Glu Glu
705                 710                 715                 720

Cys Ser Gln His Leu Pro Tyr Ile Glu Gln Gly Met Met Leu Ala Glu
                725                 730                 735

Gln Phe Lys Gln Lys Ala Leu Gly Leu Ser Arg Gly Gly Lys Pro Ala
            740                 745                 750

Ile Val Pro Asp Lys Glu Val Leu Tyr Gln Gln Tyr Asp Glu Met Glu
        755                 760                 765
```

| | | | | | | | | | | | |
|---|---|---|---|---|---|---|---|---|---|---|---|
| Glu | Cys | Ser | Gln | Ala | Ala | Pro | Tyr | Ile | Glu | Gln | Ala | Gln | Val | Ile | Ala |
| 770 | | | | | 775 | | | | | 780 | |

Glu Cys Ser Gln Ala Ala Pro Tyr Ile Glu Gln Ala Gln Val Ile Ala
770                 775                 780

His Gln Phe Lys Glu Lys Val Leu Gly Leu Ile Asp Asn Asp Gln Val
785                 790                 795                 800

Val Val Thr Pro Asp Lys Glu Ile Leu Tyr Glu Ala Phe Asp Glu Met
                805                 810                 815

Glu Glu Cys Ala Ser Lys Ala Ala Leu Ile Glu Glu Gly Gln Arg Met
            820                 825                 830

Ala Glu Met Leu Lys Ser Lys Ile Gln Gly Leu Leu Gly Ile Leu Arg
        835                 840                 845

Arg His Val Gly Pro Gly Glu Gly Ala Val Gln Trp Met Asn Arg Leu
    850                 855                 860

Ile Ala Phe Ala Ser Arg Gly Asn His Val Ser Pro Thr His Tyr Val
865                 870                 875                 880

Pro Ser Arg Ser Arg Arg Phe Ala Gln Ala Leu Pro Val Trp Ala Arg
                885                 890                 895

Pro Asp Tyr Asn Pro Pro Leu Val Glu Thr Trp Lys Lys Pro Asp Tyr
            900                 905                 910

Glu Pro Pro Val Val His Gly Arg Ser Ser Arg Phe Ala Gln Ala
        915                 920                 925

Leu Pro Val Trp Ala Arg Pro Asp Tyr Asn Pro Pro Leu Val Glu Thr
    930                 935                 940

Trp Lys Lys Pro Asp Tyr Glu Pro Pro Val Val His Gly Arg Lys Thr
945                 950                 955                 960

Lys Arg Asn Thr Asn Arg Arg Pro Gln Asp Val Lys Phe Pro Gly Gly
                965                 970                 975

Gly Gln Ile Val Gly Arg Gly Pro Pro Ile Pro Lys Ala Arg Arg
            980                 985                 990

Pro Glu Gly Arg Thr Trp Ala Gln Pro Gly Tyr Pro Trp Pro Leu Tyr
        995                 1000                1005

Gly Asn Lys Asp Arg Arg Ser Thr Gly Lys Ser Trp Gly Lys Pro
    1010                1015                1020

Gly Tyr Pro Trp Pro Arg Lys Thr Lys Arg Asn Thr Asn Arg Arg
    1025                1030                1035

Pro Gln Asp Val Lys Phe Pro Gly Gly Gly Gln Ile Val Gly Arg
    1040                1045                1050

Arg Gly Pro Pro Ile Pro Lys Ala Arg Arg Pro Glu Gly Arg Thr
    1055                1060                1065

Trp Ala Gln Pro Gly Tyr Pro Trp Pro Leu Tyr Gly Asn Lys Asp
    1070                1075                1080

Arg Arg Ser Thr Gly Lys Ser Trp Gly Lys Pro Gly Tyr Pro Trp
    1085                1090                1095

Pro

<210> SEQ ID NO 3
<211> LENGTH: 3297
<212> TYPE: DNA
<213> ORGANISM: Artificial
<220> FEATURE:
<223> OTHER INFORMATION: MEFA 7.2

<400> SEQUENCE: 3
atggctacaa aggctgtttg tgttttgaag ggtgacggcc cagttcaagg tattattaac    60
ttcgagcaga aggaaagtaa tggaccagtg aaggtgtggg aagcattaa aggactgact   120

-continued

```
gaaggcctgc atggattcca tgttcatgag tttggagata atacagcagg ctgtaccagt    180
gcaggtcctc actttaatcc tctatccaga aaacacggtg ggccaaagga tgaagagagg    240
catgttggag acttgggcaa tgtgactgct gacaaagatg gtgtggccga tgtgtctatt    300
gaagattctg tgatctcact ctcaggagac cattgcatca ttggccgcac actggtggtc    360
catgaaaaag cagatgactt gggcaaaggt ggaaatgaag aaagtacaaa gacaggaaac    420
gctggaagtc gtttggcttg tggtgtaatt gggatcgccc agaatttgaa ttctggttgc    480
aattgctcta tctatcccgg ccatataacg ggtcaccgca tggcatggaa gcttggttcc    540
gccgccagaa ctacctcggg ctttgtctcc ttgttcgccc aggtgccaa acaaaacgaa     600
actcacgtca cgggaggcgc agccgcccga actacgtctg ggttgacctc tttgttctcc    660
ccaggtgcca gccaaaacat tcaattgatt gtcgacttta tccctgtgga gaacctagag    720
acaaccatgc gatctccggt gttcacggat aactcctctc caccagtagt gccccagagc    780
ttccaggtgg ctcacctcca tgctcccaca ggcagcggca aaagcaccaa ggtcccggct    840
gcatatgcag ctcagggcta taaggtgcta gtactcaacc cctctgttgc tgcaacactg    900
ggctttggtg cttacatgtc caaggctcat gggatcgatc ctaacatcag gaccggggtg    960
agaacaatta ccactggcag ccccatcacg tactccacct acggcaagtt ccttgccgac   1020
ggcgggtgct cgggggcgc ttatgacata ataatttgtg acgagtgcca ctccacggat    1080
gccacatcca tcttgggcat tggcactgtc cttgaccaag cagagactgc gggggcgaga   1140
ctggttgtgc tcgccaccgc cacccctccg ggctccgtca ctgtgcccca tcccaacatc   1200
gaggaggttg ctctgtccac caccggagag atcccttttt acggcaaggc tatccccctc   1260
gaagtaatca agggggggag acatctcatc ttctgtcatt caaagaagaa gtgcgacgaa   1320
ctcgccgcaa agctggtcgc attgggcatc aatgccgtgg cctactaccg cggtcttgac   1380
gtgtccgtca tcccgctgcc cggcgatgtt gtcgtcgtgg caaccgatgc cctcatgacc   1440
ggctataccg gcgacttcga ctcggtgata gactgcctgc cctgtgtcac ccagacagtc   1500
gatttcagcc ttgaccctac cttcaccatt gagacaatca cgctcccca agatgctgtc    1560
tcccgcactc aacgtcgggg caggactggc agggggaagc caggcatcta cagatttgtg   1620
gcaccggggg agcgcccctc cggcatgttc gactcgtccg tcctctgtga gtgctatgac   1680
gcaggctgtg cttggtatga gctcacgccc gccgagacta cagttaggct acgagcgtac   1740
atgaacaccc cggggcttcc cgtgtgccag gaccatcttg aattttggga gggcgtcttt   1800
acaggcctca ctcatataga tgcccacttt ctatcccaga caaagcagag tggggagaac   1860
cttccttacc tggtagcgta ccaagccacc gtgtgcgcta gggctcaagc ccctcccca    1920
tcgtgggacc agatgtggaa gtgtttgatt cgcctcaagc ccaccctcca tgggccaaca   1980
cccctgctat acagactggg cgctgttcag aatgaaatca ccctgacgca cccagtcacc   2040
aaatacatca tgacatgcat gtcggccgac ctggaggtcg tcctgcccgc atgctccggg   2100
aagccggcaa tcatacctga cagggaagtc ctctaccgag agttcgatga gatggaagag   2160
cccattcagc acttaccgta catcgagcaa gggatgatgc tcgccgagca gttcaagcag   2220
aaggccctcg gcctctcgcg aggggggcaag ccggcaatcg ttccagacaa agaggtgttg   2280
tatcaacaat acgatgagat ggaagagcct atacaagctg ccccatatat cgaacaagct   2340
caggtaatag ctcaccagtt caaggaaaaa gtccttggat tgatcgataa tgatcaagtg   2400
gttgtgactc ctgacaaaga aatcttatat gaggcctttg atgagatgga agaaccaatc   2460
tccaaagccg ccctcattga ggaagggcag cggatggcgg agatgctcaa gtctaagata   2520
```

```
caaggcctcc tcgggatact gcgccggcac gttggtcctg gcgagggggc agtgcagtgg   2580
atgaaccggc tgatagcctt cgcctccaga gggaaccatg tttcccccac gcactacgtt   2640
ccgtctagat cccggagatt cgcccaggcc ctgcccgttt gggcgcggcc ggactataac   2700
cccccgctag tggagacgtg aaaaagccc gactacgaac cacctgtggt ccacggcaga   2760
tcttctcgga gattcgccca ggccctgccc gtttgggcgc ggccggacta accccccg    2820 ctagtggaga cgtggaaaaa gcccgactac gaaccacctg tggtccatgg cagaaagacc   2880
aaacgtaaca ccaaccggcg gccgcaggac gtcaagttcc cgggtggcgg tcagatcgtt   2940
ggtcgcaggg gccctcctat ccccaaggct cgtcggcccg agggcaggac ctgggctcag   3000
cccggttacc cttggcccct ctatggcaat aaggacagac ggtctacagg taagtcctgg   3060
ggtaagccag ggtacccttg gccaagaaag accaaacgta acaccaaccg acggccgcag   3120
gacgtcaagt tcccgggtgg cggtcagatc gttggtcgca ggggccctcc tatccccaag   3180
gctcgtcggc ccgagggcag gacctgggct cagcccggtt acccttggcc cctctatggc   3240
aataaggaca gacggtctac cggtaagtcc tggggtaagc cagggtatcc ttggccc      3297
```

<210> SEQ ID NO 4
<211> LENGTH: 1099
<212> TYPE: PRT
<213> ORGANISM: Artificial
<220> FEATURE:
<223> OTHER INFORMATION: MEFA 7.2

<400> SEQUENCE: 4

```
Met Ala Thr Lys Ala Val Cys Val Leu Lys Gly Asp Gly Pro Val Gln
 1               5                  10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Asn Ser Gly Cys
145                 150                 155                 160

Asn Cys Ser Ile Tyr Pro Gly His Ile Thr Gly His Arg Met Ala Trp
                165                 170                 175

Lys Leu Gly Ser Ala Ala Arg Thr Thr Ser Gly Phe Val Ser Leu Phe
            180                 185                 190

Ala Pro Gly Ala Lys Gln Asn Glu Thr His Val Thr Gly Gly Ala Ala
        195                 200                 205

Ala Arg Thr Thr Ser Gly Leu Thr Ser Leu Phe Ser Pro Gly Ala Ser
    210                 215                 220
```

```
Gln Asn Ile Gln Leu Ile Val Asp Phe Ile Pro Val Glu Asn Leu Glu
225                 230                 235                 240

Thr Thr Met Arg Ser Pro Val Phe Thr Asp Asn Ser Ser Pro Pro Val
            245                 250                 255

Val Pro Gln Ser Phe Gln Val Ala His Leu His Ala Pro Thr Gly Ser
        260                 265                 270

Gly Lys Ser Thr Lys Val Pro Ala Ala Tyr Ala Ala Gln Gly Tyr Lys
        275                 280                 285

Val Leu Val Leu Asn Pro Ser Val Ala Ala Thr Leu Gly Phe Gly Ala
    290                 295                 300

Tyr Met Ser Lys Ala His Gly Ile Asp Pro Asn Ile Arg Thr Gly Val
305                 310                 315                 320

Arg Thr Ile Thr Thr Gly Ser Pro Ile Thr Tyr Ser Thr Tyr Gly Lys
                325                 330                 335

Phe Leu Ala Asp Gly Gly Cys Ser Gly Gly Ala Tyr Asp Ile Ile Ile
                340                 345                 350

Cys Asp Glu Cys His Ser Thr Asp Ala Thr Ser Ile Leu Gly Ile Gly
            355                 360                 365

Thr Val Leu Asp Gln Ala Glu Thr Ala Gly Ala Arg Leu Val Val Leu
    370                 375                 380

Ala Thr Ala Thr Pro Pro Gly Ser Val Thr Val Pro His Pro Asn Ile
385                 390                 395                 400

Glu Glu Val Ala Leu Ser Thr Thr Gly Glu Ile Pro Phe Tyr Gly Lys
                405                 410                 415

Ala Ile Pro Leu Glu Val Ile Lys Gly Gly Arg His Leu Ile Phe Cys
                420                 425                 430

His Ser Lys Lys Lys Cys Asp Glu Leu Ala Ala Lys Leu Val Ala Leu
            435                 440                 445

Gly Ile Asn Ala Val Ala Tyr Tyr Arg Gly Leu Asp Val Ser Val Ile
    450                 455                 460

Pro Leu Pro Gly Asp Val Val Val Ala Thr Asp Ala Leu Met Thr
465                 470                 475                 480

Gly Tyr Thr Gly Asp Phe Asp Ser Val Ile Asp Cys Leu Pro Cys Val
                485                 490                 495

Thr Gln Thr Val Asp Phe Ser Leu Asp Pro Thr Phe Thr Ile Glu Thr
            500                 505                 510

Ile Thr Leu Pro Gln Asp Ala Val Ser Arg Thr Gln Arg Arg Gly Arg
    515                 520                 525

Thr Gly Arg Gly Lys Pro Gly Ile Tyr Arg Phe Val Ala Pro Gly Glu
    530                 535                 540

Arg Pro Ser Gly Met Phe Asp Ser Ser Val Leu Cys Glu Cys Tyr Asp
545                 550                 555                 560

Ala Gly Cys Ala Trp Tyr Glu Leu Thr Pro Ala Glu Thr Thr Val Arg
                565                 570                 575

Leu Arg Ala Tyr Met Asn Thr Pro Gly Leu Pro Val Cys Gln Asp His
            580                 585                 590

Leu Glu Phe Trp Glu Gly Val Phe Thr Gly Leu Thr His Ile Asp Ala
        595                 600                 605

His Phe Leu Ser Gln Thr Lys Gln Ser Gly Glu Asn Leu Pro Tyr Leu
        610                 615                 620

Val Ala Tyr Gln Ala Thr Val Cys Ala Arg Ala Gln Ala Pro Pro Pro
625                 630                 635                 640
```

-continued

```
Ser Trp Asp Gln Met Trp Lys Cys Leu Ile Arg Leu Lys Pro Thr Leu
            645                 650                 655

His Gly Pro Thr Pro Leu Leu Tyr Arg Leu Gly Ala Val Gln Asn Glu
            660                 665                 670

Ile Thr Leu Thr His Pro Val Thr Lys Tyr Ile Met Thr Cys Met Ser
            675                 680                 685

Ala Asp Leu Glu Val Val Leu Pro Ala Cys Ser Gly Lys Pro Ala Ile
            690                 695                 700

Ile Pro Asp Arg Glu Val Leu Tyr Arg Glu Phe Asp Glu Met Glu Glu
705                 710                 715                 720

Pro Ile Gln His Leu Pro Tyr Ile Glu Gln Gly Met Met Leu Ala Glu
                725                 730                 735

Gln Phe Lys Gln Lys Ala Leu Gly Leu Ser Arg Gly Gly Lys Pro Ala
            740                 745                 750

Ile Val Pro Asp Lys Glu Val Leu Tyr Gln Gln Tyr Asp Glu Met Glu
            755                 760                 765

Glu Pro Ile Gln Ala Ala Pro Tyr Ile Glu Gln Ala Gln Val Ile Ala
770                 775                 780

His Gln Phe Lys Glu Lys Val Leu Gly Leu Ile Asp Asn Asp Gln Val
785                 790                 795                 800

Val Val Thr Pro Asp Lys Glu Ile Leu Tyr Glu Ala Phe Asp Glu Met
            805                 810                 815

Glu Glu Pro Ile Ser Lys Ala Ala Leu Ile Glu Glu Gly Gln Arg Met
            820                 825                 830

Ala Glu Met Leu Lys Ser Lys Ile Gln Gly Leu Leu Gly Ile Leu Arg
            835                 840                 845

Arg His Val Gly Pro Gly Glu Gly Ala Val Gln Trp Met Asn Arg Leu
850                 855                 860

Ile Ala Phe Ala Ser Arg Gly Asn His Val Ser Pro Thr His Tyr Val
865                 870                 875                 880

Pro Ser Arg Ser Arg Arg Phe Ala Gln Ala Leu Pro Val Trp Ala Arg
            885                 890                 895

Pro Asp Tyr Asn Pro Pro Leu Val Glu Thr Trp Lys Lys Pro Asp Tyr
            900                 905                 910

Glu Pro Pro Val Val His Gly Arg Ser Ser Arg Phe Ala Gln Ala
915                 920                 925

Leu Pro Val Trp Ala Arg Pro Asp Tyr Asn Pro Leu Val Glu Thr
            930                 935                 940

Trp Lys Lys Pro Asp Tyr Glu Pro Pro Val Val His Gly Arg Lys Thr
945                 950                 955                 960

Lys Arg Asn Thr Asn Arg Arg Pro Gln Asp Val Lys Phe Pro Gly Gly
                965                 970                 975

Gly Gln Ile Val Gly Arg Arg Gly Pro Ile Pro Lys Ala Arg Arg
            980                 985                 990

Pro Glu Gly Arg Thr Trp Ala Gln Pro Gly Tyr Pro Trp Pro Leu Tyr
            995                 1000                1005

Gly Asn Lys Asp Arg Arg Ser Thr Gly Lys Ser Trp Gly Lys Pro
            1010                1015                1020

Gly Tyr Pro Trp Pro Arg Lys Thr Lys Arg Asn Thr Asn Arg Arg
            1025                1030                1035

Pro Gln Asp Val Lys Phe Pro Gly Gly Gly Gln Ile Val Gly Arg
            1040                1045                1050
```

```
Arg Gly Pro Pro Ile Pro Lys Ala Arg Arg Pro Glu Gly Arg Thr
    1055                1060                1065

Trp Ala Gln Pro Gly Tyr Pro Trp Pro Leu Tyr Gly Asn Lys Asp
    1070                1075                1080

Arg Arg Ser Thr Gly Lys Ser Trp Gly Lys Pro Gly Tyr Pro Trp
    1085                1090                1095

Pro

<210> SEQ ID NO 5
<211> LENGTH: 2058
<212> TYPE: DNA
<213> ORGANISM: Artificial
<220> FEATURE:
<223> OTHER INFORMATION: a representative NS3/4a conformational antigen
      (NS3/4a PI)

<400> SEQUENCE: 5
```

| | | | | |
|---|---|---|---|---|
| atggcgccca | tcacggcgta | cgcccagcag | acaaggggcc | tcctagggtg cataatcacc | 60 |
| agcctaactg | gccgggacaa | aaaccaagtg | gagggtgagg | tccagattgt gtcaactgct | 120 |
| gcccaaacct | tcctggcaac | gtgcatcaat | ggggtgtgct | ggactgtcta ccacggggcc | 180 |
| ggaacgagga | ccatcgcgtc | acccaagggt | cctgtcatcc | agatgtatac caatgtagac | 240 |
| caagaccttg | tgggctggcc | cgctccgcaa | ggtagccgat | cattgacacc ctgcacttgc | 300 |
| ggctcctcgg | acctttacct | ggtcacgagg | cacgccgatg | tcattcccgt cgccggcggg | 360 |
| ggtgatagca | ggggcagcct | gctgtcgccc | cggcccattt | cctacttgaa aggctcctcg | 420 |
| ggggtccgc | tgttgtgccc | cgcggggcac | gccgtgggca | tatttagggc gcggtgtgc | 480 |
| acccgtggag | tggctaaggc | ggtggacttt | atccctgtgg | agaacctaga gacaaccatg | 540 |
| aggtccccgg | tgttcacgga | taactcctct | ccaccagtag | tgccccagag cttccaggtg | 600 |
| gctcacctcc | atgctcccac | aggcagcggc | aaaagcacca | aggtcccggc tgcatatgca | 660 |
| gctcagggct | ataaggtgct | agtactcaac | ccctctgttg | ctgcaacact gggcttttggt | 720 |
| gcttacatgt | ccaaggctca | tgggatcgat | cctaacatca | ggaccggggt gagaacaatt | 780 |
| accactggca | gccccatcac | gtactccacc | tacggcaagt | tccttgccga cggcgggtgc | 840 |
| tcgggggggcg | cttatgacat | aataaatttgt | gacgagtgcc | actccacgga tgccacatcc | 900 |
| atcttgggca | ttggcactgt | ccttgaccaa | gcagagactg | cggggggcgag actggttgtg | 960 |
| ctcgccaccg | ccaccccctcc | gggctccgtc | actgtgcccc | atccaacat cgaggaggtt | 1020 |
| gctctgtcca | ccaccggaga | gatccctttt | tacggcaagg | ctatcccct cgaagtaatc | 1080 |
| aagggggggga | gacatctcat | cttctgtcat | tcaaagaaga | agtgcgacga actcgccgca | 1140 |
| aagctggtcg | cattgggcat | caatgccgtg | gcctactacc | gcggtcttga cgtgtccgtc | 1200 |
| atcccgccca | tcggcgatgt | tgtcgtcgtg | gcaaccgatg | ccctcatgac cggctatacg | 1260 |
| ggcgacttcg | actcggtgat | agactgcaat | acgtgtgtca | cccagacagt cgatttcagc | 1320 |
| cttgacccta | ccttcaccat | tgagacaatc | acgctccccc | aagatgctgt ctcccgcact | 1380 |
| caacgtcggg | gcaggactgg | caggggggaag | ccaggcatct | acagatttgt ggcaccgggg | 1440 |
| gagcgcccct | ccggcatgtt | cgactcgtcc | gtcctctgtg | agtgctatga cgcaggctgt | 1500 |
| gcttggtatg | agctcacgcc | cgccgagact | acagttaggc | tacgagcgta catgaacacc | 1560 |
| ccggggcttc | ccgtgtgcca | ggaccatctt | gaattttggg | agggcgtctt acaggcctc | 1620 |
| actcatatag | atgcccactt | tctatcccag | acaaagcaga | gtgggagaa ccttccttac | 1680 |
| ctggtagcgt | accaagccac | cgtgtgcgct | agggctcaag | ccctccccc atcgtgggac | 1740 |

```
cagatgtgga agtgtttgat tcgcctcaag cccaccctcc atgggccaac accctgcta    1800 tacagactgg gcgctgttca gaatgaaatc accctgacgc acccagtcac caaatacatc    1860
atgacatgca tgtcggccga cctggaggtc gtcacgagca cctgggtgct cgttggcggc    1920
gtcctggctg ctttggccgc gtattgcctg tcaacaggct gcgtggtcat agtgggcagg    1980
gtcgtcttgt ccgggaagcc ggcaatcata cctgacaggg aagtcctcta ccgagagttc    2040
gatgagatgg aagagtgc                                                  2058
```

<210> SEQ ID NO 6
<211> LENGTH: 686
<212> TYPE: PRT
<213> ORGANISM: Artificial
<220> FEATURE:
<223> OTHER INFORMATION: a representative NS3/4a conformational antigen
      (NS3/4a PI)

<400> SEQUENCE: 6

```
Met Ala Pro Ile Thr Ala Tyr Ala Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Ile Val Ser Thr Ala Ala Gln Thr Phe Leu Ala Thr Cys
        35                  40                  45

Ile Asn Gly Val Cys Trp Thr Val Tyr His Gly Ala Gly Thr Arg Thr
    50                  55                  60

Ile Ala Ser Pro Lys Gly Pro Val Ile Gln Met Tyr Thr Asn Val Asp
65                  70                  75                  80

Gln Asp Leu Val Gly Trp Pro Ala Pro Gln Gly Ser Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Ile Ser Tyr Leu Lys Gly Ser Ser Gly Gly Pro Leu
    130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
            180                 185                 190

Val Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ala Thr Ser Ile Leu Gly Ile
    290                 295                 300
```

```
Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
            325                 330                 335

Ile Glu Glu Val Ala Leu Ser Thr Thr Gly Glu Ile Pro Phe Tyr Gly
            340                 345                 350

Lys Ala Ile Pro Leu Glu Val Ile Lys Gly Gly Arg His Leu Ile Phe
        355                 360                 365

Cys His Ser Lys Lys Lys Cys Asp Glu Leu Ala Ala Lys Leu Val Ala
    370                 375                 380

Leu Gly Ile Asn Ala Val Ala Tyr Tyr Arg Gly Leu Asp Val Ser Val
385                 390                 395                 400

Ile Pro Pro Ile Gly Asp Val Val Val Ala Thr Asp Ala Leu Met
                405                 410                 415

Thr Gly Tyr Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Ile Thr Leu Pro Gln Asp Ala Val Ser Arg Thr Gln Arg Arg Gly
    450                 455                 460

Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Thr Val
        500                 505                 510

Arg Leu Arg Ala Tyr Met Asn Thr Pro Gly Leu Pro Val Cys Gln Asp
    515                 520                 525

His Leu Glu Phe Trp Glu Gly Val Phe Thr Gly Leu Thr His Ile Asp
530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
            565                 570                 575

Pro Ser Trp Asp Gln Met Trp Lys Cys Leu Ile Arg Leu Lys Pro Thr
        580                 585                 590

Leu His Gly Pro Thr Pro Leu Leu Tyr Arg Leu Gly Ala Val Gln Asn
    595                 600                 605

Glu Ile Thr Leu Thr His Pro Val Thr Lys Tyr Ile Met Thr Cys Met
610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
            645                 650                 655

Ile Val Gly Arg Val Val Leu Ser Gly Lys Pro Ala Ile Ile Pro Asp
        660                 665                 670

Arg Glu Val Leu Tyr Arg Glu Phe Asp Glu Met Glu Glu Cys
    675                 680                 685

<210> SEQ ID NO 7
<211> LENGTH: 21
<212> TYPE: PRT
<213> ORGANISM: Artificial
<220> FEATURE:
<223> OTHER INFORMATION: HCV epitopes
```

-continued

```
<400> SEQUENCE: 7

Gly Ser Ala Ala Arg Thr Thr Ser Gly Phe Val Ser Leu Phe Ala Pro
1               5                   10                  15

Gly Ala Lys Gln Asn
            20
```

HCV MULTIPLE EPITOPE FUSION ANTIGENS WITH MODIFIED PROTEOLYTIC CLEAVAGE SITES AND USES THEREOF

CROSS-REFERENCE TO RELATED APPLICATIONS

This application is a national stage application filed under 35 U.S.C. §371 of PCT Application No. PCT/US2005/030324, filed Aug. 26, 2005, from which application priority is claimed pursuant to 35 U.S.C. §120, which application claims the benefit under 35 U.S.C. §119(e)(1) of U.S. Provisional Applications Ser. Nos. 60/621,790, filed Oct. 25, 2004; 60/621,502, filed Oct. 22, 2004; 60/618,390, filed Oct. 12, 2004; and 60/604,858, filed Aug. 27, 2004. All of the foregoing applications are incorporated herein by reference in their entireties.

TECHNICAL FIELD

The present invention pertains generally to hepatitis C virus (HCV) constructs and methods of using the same. More particularly, the invention relates to immunogenic HCV multiple epitope fusion antigens (MEFAs) containing multiple HCV epitopes, with modified amino acid sequences to inhibit proteolytic cleavage of the MEFA by NS3. The proteins are useful in immunoassays for diagnosing HCV infection.

BACKGROUND OF THE INVENTION

HCV is an enveloped virus with a single-stranded positive-sense RNA genome of approximately 9.5 kb that encodes about 3010 amino acids (Choo et al., *Proc. Natl. Acad. Sci. USA* (1991) 88:2451-2455; Takamizawa et al., *J. Virol.* (1991) 65:1105-1113). The HCV polyprotein is processed by host and viral proteases into several mature proteins: core protein (C), envelope glycoproteins (E1 and E2), and six nonstructural proteins (NS2, NS3, NS4a, NS4b, NS5a, NS5b) (Hijikata et al. *Proc. Natl. Acad. Sci. USA* (1993) 90:10773-10777; Grakoui et al., *J. Virol.* (1993) 67:1385-1395). NS3 is a 630 amino acid protein with three enzymatic activities: the approximately N-terminal 180 amino acids provide serine protease function whereas the remaining C-terminal domains have both helicase and NTPase activities (Bartenschlager et al., *J. Virol.* (1993) 67:3835-3844; Kim et al., *Biochem. Biophys. Res. Commun.* (1995) 215:160-166; Preugschat et al., *J. Biol. Chem.* (1996) 271:24449-24457). The NS3 protease is responsible for cleavages at the NS3/4a, NS4a/4b, NS4b/5a and NS5a/5b junction sites (Grakoui et al., *J. Virol.* (1993) 67:2832-2843). NS4a includes approximately 54 amino acids and acts as a cofactor of the NS3 protease and is essential for polyprotein processing (Failla et al., *J. Virol.* (1994) 68:3753-3760).

HCV is the major etiologic agent for blood transfusion-associated and community-acquired non-A, non-B viral hepatitis (Alter et al., *N. Engl. J. Med.* (1989) 321:1494-1500; Choo et al., *Science* (1989) 244:359-362; Kuo et al., *Science* (1989) 244:362-364). HCV currently affects approximately 3% of the world's population. 70% of these individuals develop HCV chronic infection, which often progresses to liver cirrhosis and hepatocellular carcinomas (Bruix et al., *Lancet* (1989) 2:1004-1006; Saito et al., *Proc. Natl. Acad. Sci. USA* (1990) 87:6547-6549). The incidence of posttransfusion HCV has steadily declined since the implementation of routine screening for HCV antibodies among blood donors (Pillonel et al., *Transfusion* (2002) 42:980-988). Despite the proven utility of these assays for blood screening and for the diagnosis of HCV infection in symptomatic patients, important challenges to the improvement of assay performance remain. Such challenges include reducing the window of seronegativity, improving the detection of HCV samples from immunosuppressed patients, and increasing assay sensitivity to detect antibodies to the different HCV genotype-specific epitopes.

Several assays have been developed for the serodiagnosis of HCV infection. See, e.g., Choo et al., *Science* (1989) 244:359-362; Kuo et al., *Science* (1989) 244:362-364; Choo et al., *Br. Med. Bull.* (1990) 46:423-441; Ebeling et al., *Lancet* (1990) 335:982-983; van der Poel et al., *Lancet* (1990) 335:558-560; van der Poel et al., *Lancet* (1991) 337:317-319; Chien, D. Y., International Publication No. WO 94/01778; Valenzuela et al., International Publication No. WO 97/44469; and Kashiwakuma et al., U.S. Pat. No. 5,871,904.

The current commercially licensed HCV ELISA antibody tests mainly use recombinant proteins containing linear epitopes. For example, three recombinant HCV proteins from core (C22-3), NS3 and NS4 regions (C200) and NS5 are used in one of the commercially available HCV assays (Uyttendaele et al., *Vox Sang.* (1994) 66:122-129).

U.S. Pat. No. 6,632,601, incorporated herein by reference in its entirety, describes immunoassays using NS3/4a conformational epitopes, in combination with multiple epitope fusion antigens (MEFAs). For a description of HCV MEFAs see, e.g., Chien et al., *J. Clin. Microbiol.* (1999) 37:1393-1397; International Publication No. WO 97/44469; U.S. Pat. Nos. 6,514,731, 6,428,792; 6,632,601; and U.S. Patent Publication No. 20040142321. The assays using these reagents provide sensitive and reliable methods for detecting early HCV seroconversion. NS3/4a, expressed in yeast and purified under non-denaturing conditions as described in U.S. Pat. No. 6,632,601, contains both protease and helicase function. Because NS3/4a purified in this manner preserves the native conformation, it has been found to be more sensitive than the c200 or c33c antigens in early seroconversion antibody detection. In antibody assays using NS3/4a and MEFA 7.1 as antigens, seroconversion antibodies were detected 2-14 days earlier than currently marketed HCV assays. However, the NS3/4 protein undergoes self-hydrolysis and also cleaves MEFA 7.1 due to the NS3 protease activity.

International Publication Nos. WO 04/00547 and WO 01/38360, and commonly owned Provisional Patent Application No. 60/604,858, describe HCV proteins including mutated NS3 protease domains with reduced proteolytic activity. However, there remains a need for sensitive, accurate diagnostic and prognostic tools in order to provide adequate patient care as well as to prevent transmission of HCV by blood and blood products or by close personal contact.

SUMMARY OF THE INVENTION

The present invention is based in part on the finding that MEFAs with mutated cleavage sites for NS3 protease are capable of detecting HCV infection. The modified HCV MEFAs are immunoreactive and are less susceptible to proteolytic cleavage by HCV NS3 protease. Thus, the MEFAs can be used in immunoassays in combination with additional HCV polypeptides, such as HCV polypeptides that retain NS3 proteolytic activity. In one representative embodiment of the invention, the modified MEFA is used in combination with an NS3/4a conformational epitope on an immunoassay solid support. The MEFAs of the invention are not degraded during production of the immunoassay components and therefore provide superior reagents for use in HCV assays.

The use of MEFAs provides the advantages of decreased masking problems, improved selectivity and improved sensitivity for detecting antibodies by allowing a greater number of epitopes on a unit area of substrate. The assays described herein may be used to detect HCV infection caused by any of the six known genotypes of HCV.

Accordingly, in one embodiment, the invention is directed to a modified HCV multiple epitope fusion antigen (MEFA), wherein the MEFA comprises at least one epitope from the HCV helicase domain that comprises an HCV NS3 proteolytic cleavage site, and at least one epitope from an NS4 region that comprises an HCV NS3 proteolytic cleavage site, wherein the HCV NS3 proteolytic cleavage sites present in the helicase domain epitope and the NS4 epitope are mutated, such that proteolytic cleavage of the modified MEFA by NS3 is inhibited relative to proteolytic cleavage of a corresponding MEFA lacking the mutations, and further wherein the modified MEFA reacts specifically with anti-HCV antibodies present in a biological sample from an HCV-infected individual.

In certain embodiments, the mutations to the cleavage sites comprise a substitution of at least one amino acid at each of the sites, such as a substitution of the naturally occurring amino acids found at positions 1428, 1429, 1455 and 1456, numbered relative to the HCV-1 sequence. In other embodiments, the modified MEFA comprises a substitution at the NS3/4a junction of the naturally occurring amino acids found at positions 1657 and 1658, numbered relative to the HCV-1 sequence.

In yet further embodiments, the epitope from the NS4 region is 5-1-1 and comprises a substitution of the naturally occurring amino acids found at positions 1711 and 1712, numbered relative to the HCV-1 sequence. In certain embodiments, the MEFA comprises three 5-1-1 epitopes from HCV strains 1, 2 and 3, respectively, wherein each of the naturally occurring amino acids found at positions 1711 and 1712 in each of the 5-1-1 epitopes, numbered relative to the HCV-1 sequence, are substituted.

In additional embodiments, the MEFA comprises the contiguous sequence of amino acids corresponding to amino acids 1193-1658, numbered relative to HCV-1 with a substitution of the naturally occurring amino acids found at positions 1428, 1429, 1455, 1456, 1657 and 1658, numbered relative to the HCV-1 sequence, and said MEFA further comprises three 5-1-1 epitopes from HCV strains 1, 2 and 3, respectively, wherein each of the 5-1-1 epitopes comprises the contiguous sequence of amino acids corresponding to amino acids 1689-1735, numbered relative to HCV-1 with a substitution of each of the naturally occurring amino acids found at positions 1711 and 1712, numbered relative to the HCV-1 sequence.

In further embodiments, the MEFA comprises a sequence of amino acids with at least 80% sequence identity to, or an amino acid sequence with at least 80% sequence identity thereto, such as at least 90% or at least 98% sequence identity to the contiguous sequence of amino acids depicted in SEQ ID NO:4, with the proviso that the amino acids at positions 466, 467, 493, 494, 695, 696, 721, 722, 770, 771, 819 and 820 of SEQ ID NO:4 maintain the mutation that inhibits NS3 proteolytic cleavage of the MEFA. In certain embodiments, the MEFA comprises the contiguous sequence of amino acids depicted in SEQ ID NO:4. In yet further embodiments, the MEFA consists of the contiguous sequence of amino acids depicted in SEQ ID NO:4.

In additional embodiments, the invention is directed to an immunoassay solid support comprising a modified MEFA as described above. In further embodiments, the immunoassay solid support further comprises at least one HCV NS3/4a conformational epitope, wherein the NS3/4a conformational epitope reacts specifically with anti-HCV antibodies present in a biological sample from an HCV-infected individual.

In certain embodiments, the NS3/4a conformational epitope comprises a sequence of amino acids with at least 80% sequence identity to, such as at least 90% or at least 98% sequence identity to the contiguous sequence of amino acids depicted in SEQ ID NO:6. In certain embodiments, the NS3/4a conformational epitope comprises the contiguous sequence of amino acids depicted in SEQ ID NO:6. In other embodiments, the NS3/4a conformational epitope consists of the contiguous sequence of amino acids depicted in SEQ ID NO:6.

In additional embodiments, the invention is directed to a method of detecting hepatitis C virus (HCV) infection in a biological sample. The method comprises:

(a) providing an immunoassay solid support as described above;

(b) combining a biological sample with the solid support under conditions which allow HCV antibodies, when present in the biological sample, to bind to the MEFA and the NS3/4a conformational epitope if present, to form a first immune complex;

(c) adding to the solid support from step (b) under complex forming conditions a detectably labeled antibody, wherein the labeled antibody is reactive with the immune complex; and (d) detecting second immune complexes formed between the detectably labeled antibody and the first immune complex, if any, as an indication of HCV infection in the biological sample.

In yet further embodiments, the invention is directed to an immunodiagnostic test kit comprising an immunoassay solid support as described above, and instructions for conducting the immunodiagnostic test.

In additional embodiments, the invention is directed to a polynucleotide comprising a coding sequence for a modified MEFA as described above, and a recombinant vector comprising the polynucleotide and control elements operably linked to the polynucleotide whereby the coding sequence can be transcribed and translated in a host cell. In additional embodiments, the invention is directed to a host cell transformed with the recombinant vector. In still further embodiments, the invention is directed to a method of producing a recombinant MEFA comprising:

(a) providing a population of host cells described above; and (b) culturing the population of cells under conditions whereby the multiple epitope fusion antigen encoded by the coding sequence present in the recombinant vector is expressed.

In yet further embodiments, the invention is directed to a method of producing an immunoassay solid support, comprising:

(a) providing a solid support; and (b) binding to the solid support at least one modified MEFA as described above.

In certain embodiments, the invention further comprises binding to the solid support at a discrete position an HCV NS3/4a conformational epitope, wherein the conformational epitope reacts specifically with anti-HCV antibodies present in a biological sample from an HCV-infected individual. In certain embodiments, the NS3/4a conformational epitope comprises a sequence of amino acids with at least 80% sequence identity to, such as at least 90% or at least 98% sequence identity to the contiguous sequence of amino acids depicted in SEQ ID NO:6. In certain embodiments, the NS3/4a conformational epitope comprises the contiguous sequence of amino acids depicted in SEQ ID NO:6. In other embodiments, the NS3/4a conformational epitope consists of the contiguous sequence of amino acids depicted in SEQ ID NO:6.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIGS. 5A-5F (SEQ ID NOS:1 and 2) depict the DNA and corresponding amino acid sequence of MEFA 7.1.

FIGS. 9A-9F (SEQ ID NOS:3 and 4) depict the DNA and corresponding amino acid sequence of MEFA 7.2.

FIGS. 10A-10B show a comparison between the amino acid sequences of MEFA 7.1 (SEQ ID NO:2) and MEFA 7.2 (SEQ ID NO:4). The changes are bolded.

FIGS. 12A-12C show representative MEFAs that can be modified for use with the subject immunoassays. FIG. 12A is a diagrammatic representation of MEFA 3. FIG. 12B is a diagrammatic representation of MEFA 5. FIG. 12C is a diagrammatic representation of MEFA 6.

FIGS. 13A through 13D (SEQ ID NOS:5 and 6) depict the DNA and corresponding amino acid sequence of a representative NS3/4a conformational antigen for use in the present assays, termed "NS3/4a PI" herein. The amino acids at positions 403 and 404 of FIGS. 13A through 13D represent substitutions of Pro for Thr, and Ile for Ser, of the native amino acid sequence of HCV-1.

FIG. 14A shows an SDS-PAGE gel and FIG. 14B shows a Western blot.

DETAILED DESCRIPTION OF THE INVENTION

Figure 1:
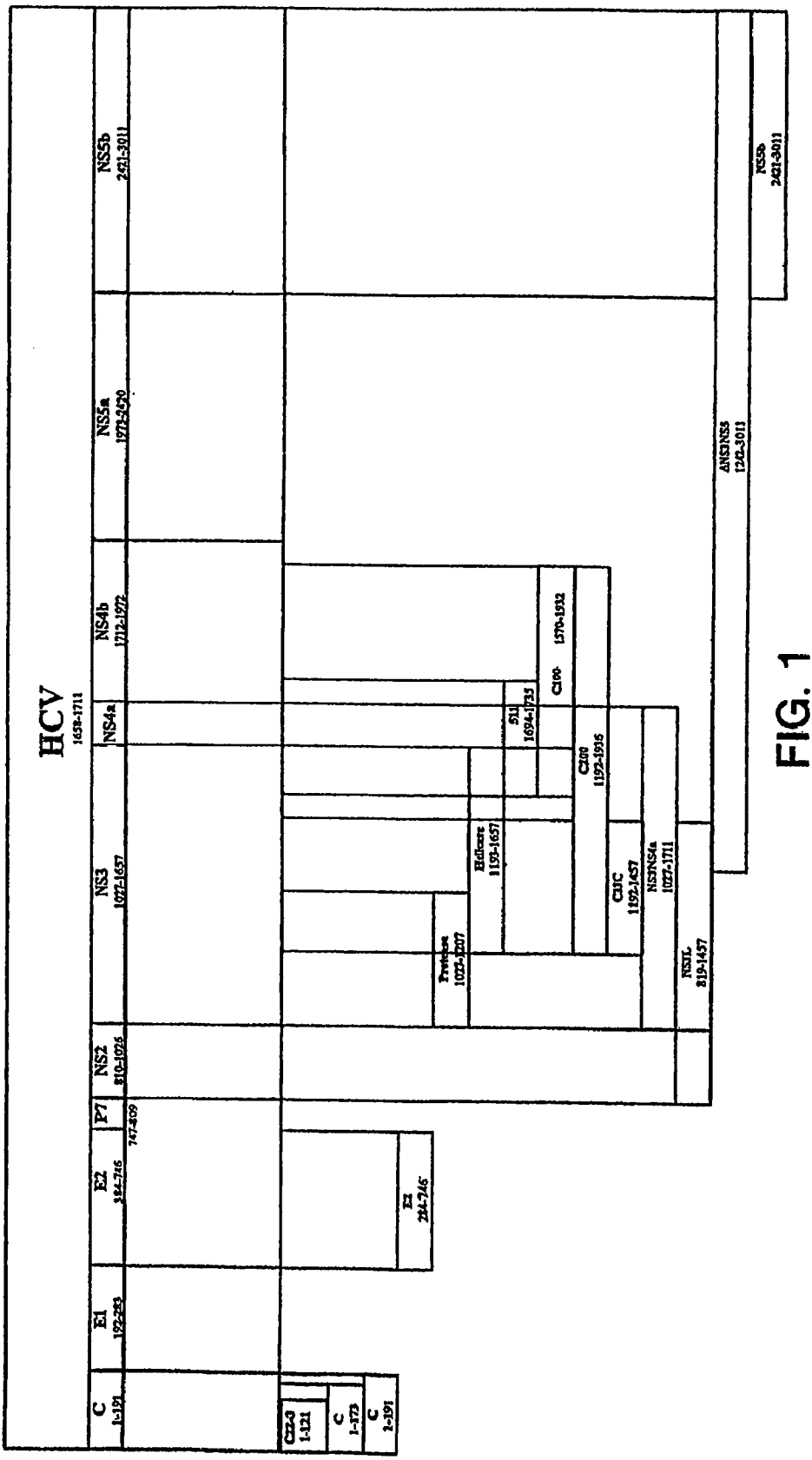
FIG. 1 is a diagrammatic representation of the HCV genome, depicting the various regions of the polyprotein from which the present assay reagents (proteins and antibodies) are derived.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology,* 2nd Edition, vol. I & II (B. N. Fields and D. M. Knipe, eds.); *Handbook of Experimental Immunology,* Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The term "comprising" encompasses "including" as well as "consisting" e.g., a composition "comprising" X may consist exclusively of X or may include something additional, for example X+Y.

The term "substantially" does not exclude "completely" e.g., a composition that is "substantially free" from Y may be completely free from Y. Where necessary, the word "substantially" may be omitted from the definition of the invention.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains and isolates, such as, but not limited to, any of the isolates from strains 1, 2, 3, 4, 5 or 6 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS3/4a" polypeptide refers to native NS3/4a from any of the various HCV strains, as well as NS3/4a analogs, muteins and immunogenic fragments, as defined further below. The complete genotypes of many of these strains are known. See, e.g., U.S. Pat. No. 6,150,087 and GenBank Accession Nos. AJ238800 and AJ238799.

A polypeptide "derived from" an HCV polyprotein intends a polypeptide which comprises a sequence of one or more regions or portions of regions of the reference HCV polyprotein. Typically, the polypeptide is composed of regions or portions of regions that include epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature, or in the case of a modified MEFA, generally non-conservative in nature at the NS3 proteolytic cleavage sites) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., *Chem. Biol.* (2000) 7:463-473; and Simon et al., *Proc. Natl. Acad. Sci. USA* (1992) 89:9367-9371 for descriptions of peptoids). Preferably, the analog or mutein has at least the same immunoactivity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact.

One of skill in the art may readily determine regions of the molecule of interest that can tolerate change by reference to Hopp/Woods and Kyte-Doolittle plots, well known in the art.

The term "multiple epitope fusion antigen" or "MEFA" as used herein intends a polypeptide in which multiple viral antigens are arranged as a single, continuous chain of amino acids, which chain does not occur in nature. As used herein, the MEFAs are limited to HCV antigens. The HCV antigens may be connected directly to each other by peptide bonds or may be separated by intervening amino acid sequences. The fusion antigens may also contain sequences exogenous to the HCV polyprotein. Moreover, the HCV sequences present may be derived from multiple genotypes and/or isolates of HCV. Examples of particular MEFAs that can be modified for use in the present immunoassays are detailed in, e.g., International Publication No. WO 97/44469; U.S. Pat. Nos. 6,514,731, 6,428,792 and 6,632,601, all of which are incorporated herein by reference. MEFAs are described further below.

By "modified MEFA" is meant a MEFA as defined above, with a mutation to the naturally occurring HCV antigen sequence at one or more NS3 proteolytic cleavage sites, such that protease activity of NS3 on the MEFA is inhibited. The modified MEFAs therefore are less susceptible to proteolytic cleavage by NS3 protease as compared with the parent, unmodified MEFA. The modified MEFA will include at least one modified epitope from the helicase domain and preferably epitopes from NS4a/NS4b and/or NS5a. By "modified epitope" is meant that one or more NS3 proteolytic cleavage sites within the epitope is mutated as compared to the naturally occurring amino acid sequence such that proteolytic cleavage of the MEFA by the NS3 protease is inhibited. The mutations present in the modified MEFA can include one or more amino acid additions, substitutions (generally non-conservative in nature) and/or deletions, relative to the native molecule, wherein the susceptibility to NS3 proteolytic cleavage is reduced or eliminated. Methods of measuring proteolytic cleavage of the subject MEFA are known in the art and include incubating the MEFAs in question with a protein known to have NS3 proteolytic activity, such as the NS3/4a conformational antigen discussed further below and shown in FIGS. 13A-13D, and monitoring the MEFA for cleavage. This assay is described in detail in the examples.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunoreactivity in the assays described herein. For example, preferred immunogenic fragments, include but are not limited to fragments of HCV core that comprise, e.g., amino acids 10-45, 10-53, 67-88, and 120-130 of the polyprotein, epitope 5-1-1 (in the NS4a/NS4b region of the viral genome) as well as defined epitopes derived from any of the regions of the polyprotein shown in FIG. 1, such as but not limited to the E1, E2, NS3 (e.g., polypeptide c33c from the NS3 region), NS4 (e.g., polypeptide c100 from the NS3/NS4 regions), NS3/4a and NS5 regions of the HCV polyprotein, as well as any of the other various epitopes identified from the HCV polyprotein. See, e.g., Chien et al., *Proc. Natl. Acad. Sci. USA* (1992) 89:10011-10015; Chien et al., *J. Gastroent.*

*Hepatol.* (1993) 8:S33-39; Chien et al., International Publication No. WO 93/00365; Chien, D. Y., International Publication No. WO 94/01778; U.S. Pat. Nos. 6,150,087 and 6,121,020, all of which are incorporated by reference herein in their entireties.

The term "epitope" as used herein refers to a polypeptide sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715, all incorporated herein by reference in their entireties. Using such techniques, a number of epitopes of HCV have been identified See, e.g., Chien et al., *Viral Hepatitis and Liver Disease* (1994) pp. 320-324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three-dimensional structure. The length of the epitope-defining sequence can be subject to wide variations as these epitopes are believed to be formed by the three-dimensional shape of the antigen (e.g., folding). Thus, amino acids defining the epitope can be relatively few in number, but widely dispersed along the length of the molecule (or even on different molecules in the case of dimers, etc.), being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in, e.g., the NS3/4a region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest. Additionally, in the case of NS3/4a, a molecule which preserves the native conformation will also have protease and, optionally, helicase enzymatic activities. Such activities can be detected using enzymatic assays, as described further below. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are incorporated by reference herein in their entireties. Alternatively, it is possible to express the antigens and further renature the protein after recovery. It is also understood that chemical synthesis may also provide conformational antigen mimitopes that cross-react with the "native" antigen's conformational epitope.

An "antibody" intends a molecule that specifically binds to an epitope of interest present in an antigen. By "specifically binds" is meant that the antibody recognizes and interacts with the epitope in a "lock and key" type of interaction to form a complex between the antigen and antibody, as opposed to non-specific binding that might occur between the antibody and, for instance, the test substrate. Thus, for example, an HCV core antibody is a molecule that specifically binds to the HCV core protein, an HCV NS3/4a antibody is a molecule that specifically binds to an epitope of an HCV NS3/4a protein, and so on. Similarly, an antigen of interest "reacts specifically" with an antibody, when the antibody "specifically binds" to an epitope present in the antigen. The term "antibody" as used herein includes antibodies obtained from both polyclonal and monoclonal preparations, as well as, the following: hybrid (chimeric) antibody molecules (see, for example, Winter et al. (1991) *Nature* 349:293-299; and U.S. Pat. No. 4,816,567); F(ab')2 and F(ab) fragments; Fv molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. *Monclonal Antibodies and Cancer Therapy*, Alan R. Liss, 1985, p. 77.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, or 3 of HCV. More specifically, epitopes are known, such as "5-1-1", occurring at approximately positions 1694-1735, numbered relative to the HCV-1 polyprotein sequence (see, FIG. 1), and such epitopes vary between the strains 1, 2, and 3. Thus, the epitope 5-1-1 from the three different strains are equivalent antigenic determinants and therefore are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs are readily available. Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

As used herein, a "biological sample" refers to a sample of tissue or fluid isolated from a subject, that commonly includes antibodies produced by the subject. Typical samples that include such antibodies are known in the art and include but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

"Solid support" intends a solid matrix to which the HCV polypeptides used in the subject immunoassays are bound covalently or by noncovalent means such as hydrophobic adsorption.

"Immunologically reactive" or "immunoreactive" means that the antigen in question will react specifically with anti-HCV antibodies present in a biological sample from an HCV-infected individual.

"Immunogenic" intends that the antigen is question will elicit an immune reaction when administered to an individual.

"Immune complex" intends the combination formed when an antibody binds to an epitope on an antigen.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, fluorescent nanoparticles, dyes, metal ions, metal sols, ligands (e.g., biotin, avidin, streptavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel HCV MEFAs with modified NS3 protease cleavage sites such that proteolytic cleavage of the modified MEFA by HCV NS3 protease is inhibited. Such modified MEFAs are especially useful in diagnostic methods for accurately detecting early HCV infection. The modified MEFAs include various HCV polypeptides, either from the same or different HCV genotypes and isolates, such as multiple immunodominant epitopes, for example, major linear epitopes of HCV core, E1, E2, NS3, NS4, 5-1-1, c100-3 and NS5 sequences.

The modified MEFAs can be used in immunoassays alone or in combination with other HCV antigens, preferably in combination with highly immunogenic conformational epitopes derived from the NS3/4a region of the HCV polyprotein. The immunoassays can be used to detect HCV infection during the early stages of HCV seroconversion, thereby increasing detection accuracy and reducing the incidence of false results. The methods can be conveniently practiced in a single assay, using any of the several assay formats described below, such as but not limited to, assay formats which utilize a solid support to which the HCV antigens are bound. In order to further an understanding of the invention, a more detailed discussion is provided below regarding modified MEFAs, HCV conformational NS3/4a epitopes, as well as production of the proteins, and methods of using the proteins.

HCV MEFAs

The genomes of HCV strains contain a single open reading frame of approximately 9,000 to 12,000 nucleotides, which is transcribed into a polyprotein. As shown in FIG. 1 and Table 1, an HCV polyprotein, upon cleavage, produces at least ten distinct products, in the following order:

NH$_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) *Proc. Natl. Acad. Sci. USA* 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, in combination with NS3, (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657 ("the helicase domain"). NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011). Completion of polyprotein maturation is initiated by autocatalytic cleavage at the NS3-NS4a junction, catalyzed by the NS3 serine protease.

TABLE 1

| Domain | Approximate Boundaries* |
| --- | --- |
| C (core) | 1-191 |
| E1 | 192-383 |
| E2 | 384-746 |
| P7 | 747-809 |
| NS2 | 810-1026 |
| NS3 | 1027-1657 |
| NS4a | 1658-1711 |
| NS4b | 1712-1972 |
| NS5a | 1973-2420 |
| NS5b | 2421-3011 |

*Numbered relative to HCV-1. See, Choo et al. (1991) Proc. Natl. Acad. Sci. USA 88: 2451-2455.

Nucleic acid and amino acid sequences of a number of HCV strains and isolates, including nucleic acid and amino acid sequences of the various regions of the HCV polyprotein, including Core, NS2, p7, E1, E2, NS3, NS4, NS5a, NS5b genes and polypeptides have been determined.

Publications that describe HCV-1 isolates include Choo et al. (1990) *Brit. Med. Bull.* 46:423-441; Choo et al. (1991) *Proc. Natl. Acad. Sci. USA* 88:2451-2455 and Han et al. (1991) *Proc. Natl. Acad. Sci. USA* 88:1711-1715. HCV isolates HC-J1 and HC-J4 are described in Okamoto et al. (1991) *Japan J. Exp. Med.* 60:167-177. HCV isolates HCT 18~, HCT 23, Th, HCT 27, EC1 and EC10 are described in Weiner et al. (1991) *Virol.* 180:842-848. HCV isolates Pt-1, HCV-K1 and HCV-K2 are described in Enomoto et al. (1990) *Biochem. Biophys. Res. Commun.* 170:1021-1025. HCV isolates A, C, D & E are described in Tsukiyama-Kohara et al. (1991) *Virus Genes* 5:243-254. Isolate HCV J1.1 is described in Kubo et al. (1989) *Japan. Nucl. Acids Res.* 17.10367-10372; Takeuchi et al. (1990) *Gene* 91:287-291; Takeuchi et al. (1990) *J. Gen. Virol.* 71:3027-3033; and Takeuchi et al. (1990) *Nucl. Acids Res.* 18:4626. The complete coding sequences of two independent isolates, HCV-J and BK, are described by Kato et al., (1990) *Proc. Natl. Acad. Sci. USA* 87:9524-9528 and Takamizawa et al., (1991) *J. Virol.* 65:1105-1113 respectively.

As explained above, the invention pertains to modified multiple epitope fusion antigens (MEFAs) for use in immunoassays for HCV detection. The modified MEFAs include multiple HCV epitopes derived from any of the various HCV viral regions shown in FIG. 1 and Table 1, and as described further below. Typically, the modified MEFAs include at least 3 epitopes, preferably 3-25 or more epitopes, for example at least 5, 6, 7, 8, 9, 10, 11, 12, 13, 14, 15, 16, 17, 18, 19, or 20 epitopes or more, such as 10-20 epitopes, derived from at least 3 different regions of the HCV polyprotein, more typically from 4-10 regions of the HCV polyprotein, such as from 5-8, e.g., 5, 6, 7, 8, regions of the HCV polyprotein. The modified MEFA will include at least one modified epitope from the helicase domain and preferably epitopes from NS4a/NS4b and/or NS5a. The modified MEFAs can also include non-HCV sequences, such as sequences that aid in recombinant expression of the MEFA, including superoxide dismutase sequences, as described further below.

In the modified MEFA, the multiple HCV antigens are arranged as a single, continuous chain of amino acids, which chain does not occur as such in nature. Thus, the linear order of the epitopes is different from the linear order of these epitopes in the genome in which they occur. The linear order of the sequences of the modified MEFAs for use herein is preferably arranged for optimum antigenicity. Preferably, the epitopes are from more than one HCV strain, such as 2, 3, 4, 5, 6 or more strains, thus providing the added ability to detect multiple strains of HCV in a single assay. Additionally, the polypeptides present in the MEFA can be selected based on the particular viral clades endemic in specific geographic regions where immunodiagnostic will be used. It is readily apparent that such MEFAs provide an effective means of diagnosing HCV infection in a wide variety of contexts. Moreover, the use of modified MEFAs assures that proteolytic cleavage of the MEFA by NS3 protease will not occur, thus providing better reagents for use in HCV immunoassays.

The modified MEFAs of the invention are mutated at NS3 proteolytic cleavage sites such that cleavage of the modified MEFA by NS3 is inhibited. The NS3 proteolytic cleavage sites are found at the NS3/4a, NS4a/4b, NS4b/5a and NS5a/5b junction sites (Grakoui et al., *J. Virol.* (1993) 67:2832-2843). Thus, referring to Table 1, these sites occur at amino acid positions 1657/1658, 1711/1712, 1972/1973 and 2420/2421, respectively, numbered relative to the HCV-1 polyprotein sequence. Moreover, cleavage sites also occur within the helicase domain of NS3 at positions 1428/1429 and 1455/1456, numbered relative to the HCV-1 polyprotein sequence. Additional sites for modification can be determined by one of skill in the art based on the known structure and function of the HCV NS3 protease as described in e.g., De Franceco et al., *Antivir. Ther.* (1998) 3:99-109; and Schechter and Berger, *Biochim. Biophys. Res. Commun.* (1967) 27:157-162.

The MEFA can be modified by deletion of all or some of the NS3 proteolytic cleavage sites. Alternatively, proteolytic cleavage by NS3 protease can be inhibited by substitution of amino acids within the proteolytic cleavage sites such that the sites do not act as a substrate for NS3 protease. Finally, additions of amino acids such that the proteolytic cleavage site is modified so that NS3 protease does not act on it, will also serve to inhibit proteolytic activity. Additional modifications that do not affect proteolytic cleavage, may also, but need not be, present in the epitopes found in the MEFAs of the invention. As will be apparent in keeping with the use of the modified MEFA, any modifications to eliminate protease cleavage sites should not affect the immunoreactivity of the MEFA so modified.

Thus, for example, one or more of the amino acids at one or more of the above sites, such as 1, 2, 3, 4, 5, 6, 7, 8, or all of these amino acids, can be substituted or deleted in order to retard proteolytic cleavage of the MEFA by NS3 protease. Alternatively, additions can be made to these cleavage sites in order to inhibit cleavage by NS3 protease.

In preferred embodiments, each of the amino acids at all of the proteolytic cleavage sites present in the MEFA are modified in order to prevent cleavage by NS3 protease. Thus, if the MEFA includes one or more epitopes that span cleavage sites in the helicase domain, the NS3/4a junction, the NS4a/NS4b junction, etc., the amino acids defining the sites will be substituted or modified. Particular substitutions for sites in the helicase domain include a substitution of the amino acid Leu for Thr which normally occurs at position 1428 of the HCV-1 polyprotein; a substitution of Pro for Ser which normally occurs at position 1429 of the HCV-1 polyprotein; a substitution of Leu for Asn which normally occurs at position 1455 of the HCV-1 polyprotein; and a substitution of Pro for Thr which normally occurs at position 1456 of the HCV-1 polyprotein. Particular substitutions at the NS3/4a junction include a substitution of Leu for Thr which normally occurs at position 1657 of the HCV-1 polyprotein; and a substitution of Pro for Ser which normally occurs at position 1658 of the HCV-1 polyprotein. It is to be understood that the amino acids stated above at these positions are with reference to the HCV-1 sequence and that the MEFA may also include epitopes from helicase and NS3/4a domains of any of the other HCV genotypes which may or may not have the same amino acids in these positions, in which case the corresponding amino acid would be substituted with an amino acid that serves to inhibit proteolytic cleavage of the MEFA by NS3.

Moreover, other appropriate amino acid modifications at these sites can be readily determined by one of skill in the art based on the known structure and function of the HCV NS3 protease as described in e.g., De Francesco et al., *Antivir. Ther.* (1998) 3 (Suppl 3):99-109; and Schechter and Berger, *Biochim. Biophys. Res. Commun.* (1967) 27:157-162. In particular, it is known that NS3 protease is a serine protease and the proteolytic mechanism is based on nucleophilic attack of the targeted peptidic bond by a serine. Aligned side chains of serine, histidine and aspartate build the catalytic triad common to most serine proteases. The active site of serine proteases is shaped as a cleft where the polypeptide substrate binds. Schechter and Berger, *Biochim. Biophys. Res. Commun.* (1967) 27:157-162 labeled amino acid residues from N to C terminus of the polypeptide substrate (Pi, . . . , P3, P2, P1, P1', P2', P3', . . . , Pj) and their respective binding subsides (Si, . . . , S3, S2, S1, S1', S2', S3', . . . , Sj) and found the cleavage is catalyzed between P1 and P1'. The NS3 protease adopts a chymotrypsin-like fold and includes a very long, solvent exposed substrate-binding site, consistent with the requirement for very long peptide substrates (P6-P4'). The NS3 protease has a preference for cysteine residues in the substrate P1 position. Thus, based on the known structure and function as described above and in the art, one of skill in the art can readily determine other amino acid substitutions, additions and deletions that will serve to disrupt the proteolytic cleavage sites for NS3 protease and therefore produce a MEFA less susceptible to cleavage.

Particular substitutions at the NS4a/4b junction, found in the 5-1-1 epitope, if present in the MEFA, include a substitution of Pro for Cys which normally occurs at position 1711 of the HCV-1 polyprotein and a substitution of Ile for Ser which normally occurs at position 1712 of the HCV-1 polyprotein. The 5-1-1 epitope is found at approximately positions 1694-1735, numbered relative to the HCV-1 polyprotein sequence. It is to be understood that the amino acids stated above at these positions are with reference to the HCV-1 sequence and that the MEFA may also, and preferably does, include epitopes from 5-1-1 domains of any of the other HCV genotypes which may or may not have the same amino acids in these positions, in which case the corresponding amino acid would be substituted with an amino acid that serves to inhibit proteolytic cleavage of the MEFA by NS3. For example, the native amino acids at positions 1711 and 1712 of HCV-3 are the same as those found in HCV-1. The amino acid at position 1711 of HCV-2 is the same as HCV-1 and HCV-3. However, the amino acid occurring at position 1712 of HCV-2 is Ala. This Ala can be substituted with, e.g., Ile, in order to inhibit proteolytic cleavage of the MEFA by NS3. Moreover, other appropriate amino acid modifications at these sites can be readily determined by one of skill in the art based on the known structure and function of the HCV NS3 protease as described in e.g., De Francesco et al., *Antivir. Ther.* (1998) 3:99-109; and Schechter and Berger, *Biochim. Biophys. Res. Commun.* (1967) 27:157-162.

As explained above, the MEFAs of the present invention include at least one or more epitopes derived from the NS3 and NS4a regions (either linear or conformational), such as from the helicase and/or protease regions of NS3. The MEFA may therefore include multiple immunodominant epitopes derived from the NS3/4a region from one or more HCV isolates. If multiple NS3/4a epitopes are used in the multiple epitope fusion, they may be the same or different epitopes. Alternatively, the fusion antigen may include one or more epitopes derived from the NS3/4a region, as well as major linear epitopes from other HCV regions such as, without limitation, HCV core, E1, E2, P7, NS4b, NS5a and NS5b sequences.

Polypeptides comprising epitopes derived from the NS3/4a region include, without limitation, polypeptides comprising all or a portion of the NS3, NS4a and NS3/4a regions and may include epitopes from the helicase and/or protease domain of NS3. A number of epitopes from these regions are known, including, but not limited to antigens derived from the c33c, c200 and c100 regions, as well as fusion proteins comprising an NS3 epitope, such as c25. These and other NS3 epitopes are useful in the present MEFAs and are known in the art and described in, e.g., Houghton et al, U.S. Pat. No. 5,350,671; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and U.S. Pat. Nos. 6,346,375 and 6,150,087, the disclosures of which are incorporated herein by reference in their entireties.

Moreover, the antigenic determinant known as 5-1-1 is partially within the NS4a region (see, FIG. 1) and is particularly useful in the MEFAs for use in the subject assays. The 5-1-1 epitope is found at approximately positions 1694-1735, numbered relative to the HCV-1 polyprotein sequence. This antigenic determinant appears in different forms on HCV-1, HCV-2 and HCV-3. Accordingly, in a preferred embodiment of the invention all of these forms of 5-1-1 appear in the multiple epitope fusion antigen used in the subject immunoassays.

The modified MEFAs can also include epitopes from the core region of any of the various HCV isolates. This region occurs at amino acid positions 1-191 of the HCV polyprotein, numbered relative to HCV-1. Either the full-length protein, fragments thereof, such as amino acids 1-150, e.g., amino acids 1-130, 1-120, for example, amino acids 1-121, 1-122, 1-123, etc., or smaller fragments containing epitopes of the full-length protein may be present in the subject MEFAs, such as those epitopes found between amino acids 9-32, 10-53, 10-45, 39-42, 64-88, 67-84, 67-88, 120-130, or any of the core epitopes identified in, e.g., Houghton et al., U.S. Pat. No. 5,350,671; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and U.S. Pat. Nos. 6,280,927 and 6,150,087, the disclosures of which are incorporated herein by reference in their entireties. Moreover, a protein resulting from a frameshift in the core region of the polyprotein, such as described in International Publication No. WO 99/63941, may be used.

Similarly, polypeptides from the HCV E1 and/or E2 regions can be used in the modified MEFAs. E2 exists as multiple species (Spaete et al., *Virol.* (1992) 188:819-830; Selby et al., *J. Virol.* (1996) 70:5177-5182; Grakoui et al., *J. Virol.* (1993) 67:1385-1395; Tomei et al., *J. Virol.* (1993) 67:4017-4026) and clipping and proteolysis may occur at the N- and C-termini of the E2 polypeptide. Thus, an E2 polypeptide for use herein may comprise full-length or N- and/or C-terminally truncated immunogenic proteins, such as proteins having amino acids 405-661, e.g., 400, 401, 402 . . . to 661, e.g., 405-444, 383 or 384-661, 383 or 384-715, 383 or 384-746, 383 or 384-749 or 383 or 384-809, or 383 or 384 to any C-terminus between 661-809, of an HCV polyprotein, numbered relative to the full-length HCV-1 polyprotein. Additional HCV epitopes for use in the MEFAs include epitopes derived from the hypervariable region of E2, such as a region spanning amino acids 384-414 or 390-410, or the consensus sequence from this region, Gly-Ser-Ala-Ala-Arg-Thr-Thr-Ser-Gly-Phe-Val-Ser-Leu-Phe-Ala-Pro-Gly-Ala-Lys-Gln-Asn (SEQ D NO:7), which represents a consensus sequence for amino acids 390-410 of the HCV type 1 genome. A representative E2 epitope present in a MEFA of the invention can comprise a hybrid epitope spanning amino acids 384-414. Such a hybrid E2 epitope can include a consensus sequence representing amino acids 390-410 fused to a consensus sequence from a second strain. Alternatively, the E2 epitope present may comprise a hybrid epitope spanning amino acids 390-444. Such a hybrid E2 epitope can include a consensus sequence representing amino acids 390-410 as detailed above, fused to e.g., the native amino acid sequence for amino acids 411-444 of HCV E2.

Additionally, the modified MEFAs may include E1 polypeptides, such as epitopes that comprise amino acids 192-326, 192-330, 192-333, 192-360, 192-363, 192-383, or 192 to any C-terminus between 326-383, of an HCV polyprotein, such as an E1 epitope including amino acids 303-320.

As explained above, the antigens may be derived from various HCV strains. Multiple viral strains of HCV are known, and epitopes derived from any of these strains can be used in a fusion protein. It is well known that any given species of organism varies from one individual organism to another and further that a given organism such as a virus can have a number of different strains. For example, as explained above, HCV includes at least 6 genotypes. Each of these genotypes includes equivalent antigenic determinants. More specifically, each strain includes a number of antigenic determinants that are present on all strains of the virus but are slightly different from one viral strain to another. For example, HCV includes the antigenic determinant known as 5-1-1 (see, FIG. 1). As explained above, this particular antigenic determinant appears in different forms HCV-1, HCV-2 and HCV-3. Accordingly, in a preferred embodiment of the invention all of these forms of 5-1-1 appear on the multiple epitope fusion antigen used in the subject immunoassays. Similarly, equivalent antigenic determinants from the core region of different HCV strains may also be present. In general, equivalent antigenic determinants have a high degree of homology in terms of amino acid sequence which degree of homology is generally 30% or more, preferably 40% or more, when aligned. The multiple copy epitope of the present invention can also include multiple copies which are exact copies of the same epitope.

FIG. 8 shows a representative modified MEFA, termed "MEFA 7.2" herein. However, it is to be understood that other epitopes derived from the HCV genome will also find use in the modified MEFAs of the invention. The parent MEFA that formed the template for MEFA 7.2 was "MEFA 7.1." The map of MEFA 7.1 and the corresponding DNA and amino acids sequences of MEFA 7.1 are shown in FIGS. 4 and 5A-5F, respectively. MEFA 7.1 is described in detail in U.S. Pat. No. 6,632,601, incorporated herein by reference in its entirety. A comparison of the amino acid sequences of MEFA 7.1 and MEFA 7.2 is shown in FIGS. 10A-10B, with the differences between the two constructs highlighted in bold. All differences occur at the proteolytic cleavage sites detailed above. Thus, the mutations numbered relative to the MEFA sequence occur at positions 466, 467, 493, 494, 695, 696, 721, 722, 770, 771, 819 and 820 of FIGS. 10A-10B. These amino acid positions correspond to positions 1428, 1429, 1455, 1456, 1657, 1658, 1711, 1712, 1711, 1712, 1711 and 1712 (due to the three 5-1-1 repeats), respectively, numbered relative to the HCV-1 polyprotein sequence.

The DNA sequence and corresponding amino acid sequence of MEFA 7.2, is shown in FIGS. 9A-9F. The general structural formula for MEFA 7.2 is shown in FIG. 8 and is as follows: hSOD-E1(type 1)-E2 HVR consensus(type 1a)-E2 HVR consensus(types 1 and 2)-mutated helicase(type 1)-mutated 5-1-1(type 1)-mutated 5-1-1(type 3)-mutated 5-1-1 (type 2)-c100(type 1)-NS5(type 1)-NS5(type 1)-core epitopes (types 1+2)-core epitopes (types 1+2). This MEFA includes the following amino acid sequence, numbered relative to HCV-1 (the numbering of the amino acids set forth below follows the numbering designation provided in Choo, et al. (1991) *Proc. Natl. Acad. Sci. USA* 88:2451-2455, in which amino acid #1 is the first methionine encoded by the coding sequence of the core region): amino acids 1-156 of superoxide dismutase (SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1193-1658 of the HCV-1 polyprotein which define the helicase, with mutations at amino acids corresponding to amino acids 1428, 1429, 1455, 1456, 1657 and 1658 of the polyprotein (amino acids 466, 467, 493, 494, 695 and 696, numbered relative to the MEFA sequence shown in FIGS. 9A-9F); three copies of an epitope from 5-1-1, amino acids 1689-1735, one from HCV-1, one from HCV-3 and one from HCV-2, which copies are equivalent antigenic determinants from the three different viral strains of HCV and each of which copies have mutations at amino acids corresponding to 1711 and 1712 of the polyprotein (amino acids 721, 722, 770, 771, 819 and 820, numbered relative to the MEFA sequence shown in FIGS. 9A-9F); HCV polypeptide C100 of HCV-1, amino acids 1901-1936 of the polyprotein; two exact copies of an epitope from the NS5 region of HCV-1, each with amino acids 2278 to 2313 of the HCV polyprotein; and two copies of several epitopes from the core region, one from HCV-1 and one from HCV-2, which copies are equivalent antigenic determinants represented by amino acids 9 to 32, 39-42 and 64-88 of HCV-1 and 67-84 of HCV-2.

Table 2 shows the amino acid positions of the various epitopes with reference to FIGS. 9A-9F herein.

TABLE 2

| MEFA 7.2 | | | | |
|---|---|---|---|---|
| MEFA aa# | 5' end site | epitope | HCV aa# | strain |
| 1-156 | Nco1 | hSOD | | |
| 159-176 | EcoR1 | E1 | 303-320 | 1 |
| 179-199 | HindIII | E2 HVR1a consensus | 390-410 | 1 |
| 200-230 | HindIII | E2 HVR1 + 2 consensus | 384-414 | 1 + 2 |
| 231-696 | Sal1 | Helicase 3 LP mutants | 1193-1658 | 1 |
| 699-745 | Sph1 | 5-1-1 PI mut | 1689-1735 | 1 |
| 748-794 | Nru1 | 5-1-1 PI mut | 1689-1735 | 3 |
| 797-843 | Cla1 | 5-1-1 PI mut | 1689-1735 | 2 |
| 846-881 | Ava1 | C100 | 1901-1936 | 1 |
| 884-919 | Xba1 | NS5 | 2278-2313 | 1 |
| 922-957 | Bgl11 | NS5 | 2278-2313 | 1 |
| 958-1028 | Nco1 | core epitopes | 9-32, 39-42<br>64-88<br>67-84 | 1<br>1<br>2 |
| 1029-1099 | Bal1 | core epitopes | 9-32, 39-42,<br>64-88<br>67-84 | 1<br>1<br>2 |

Thus, one particular modified MEFA is represented by MEFA 7.2. MEFAs showing substantial homology to MEFA 7.2, as defined above, are also intended. Such MEFAs may have sequences that exhibit at least about 50%, preferably at least about 75%, more preferably at least about 80%-85%, preferably at least about 90%, and most preferably at least about 95%-98% sequence identity over the entire length of the molecules, so long as at least one modification to the proteolytic cleavage sites, and preferably all of the modifications to the proteolytic cleavage sites remain, and the MEFAs are immunoreactive and hence useful in HCV immunodiagnostics as described herein.

As explained above, MEFA 7.2 was made using MEFA 7.1 as a template. However, numerous other known MEFAs can be modified as described above, to provide additional modified MEFAs with decreased susceptibility to proteolytic cleavage by NS3. MEFAs that can be modified as described herein include MEFA-3, MEFA-5 and MEFA-6, depicted in FIGS. 12A, 12B and 12C, respectively, and described in International Publication Nos. WO 01/96875, WO 01/09609, WO 97/44469 and U.S. Pat. Nos. 6,514,731 and 6,428,792, incorporated herein by reference in their entireties. For example, the epitope sequence arrangement of MEFA 6 is similar to MEFA 7.2. However, MEFA 7.2 incorporates the E2 hypervariable (HVR) region and the E2 HVR 1+2 consensus sequence. Additionally, the entire helicase region of NS3 is included in MEFA 7.2. Thus, MEFA 7.2 is considerably larger than MEFA 6, with a molecular weight of approximately 120 kDa. The expression level in yeast, however, is similar to that of MEFA 6, and can be purified to more than 95% purity and is scalable.

The modified MEFAs are used alone, or preferably in combination with another HCV antigen, such as any of the HCV immunogenic proteins described above with reference to the MEFAs. In preferred embodiments, the modified MEFA is used in combination with an HCV NS3/4a epitope, preferably a conformational epitope, in immunoassays to detect HCV virus. Thus, in one embodiment of the invention, depicted in FIG. 2, a rapid capture ligand immunoassay is performed using a MEFA 7.2 and an NS3/4a epitope. The sample is combined with the antigens, which may be present on a solid support, as described further below. If the sample is infected with HCV, HCV antibodies to those epitopes present on the solid support will bind to the solid support components. Detection is by the attachment of a detectable marker (such as horse radish peroxidase (HRP) as shown in FIG. 2) to a member of the antigen/antibody complex. Attachment may be by covalent means or by subsequent binding of detectably labeled antibodies, or known antigens, such as in a standard sandwich assay, or by enzyme reaction, the product of which reaction is detectable. The detectable marker may include, but is not limited to, a chromophore, an antibody, an antigen, an enzyme, an enzyme reactive compound whose cleavage product is detectable, rhodamine or rhodamine derivative, biotin, avidin, streptavidin, a fluorescent compound, a chemiluminescent compound, such as dimethyl acridinium ester (DMAE, Ciba Corning Diagnostics Corp.), derivatives and/or combinations of these markers. A detectably labeled anti-human antibody, capable of detecting a human IgG molecule present, can be conveniently used. Alternatively, a detectably labeled HCV antigen, e.g., an NS3/4a or a MEFA, can be used.

HCV NS3/4a Conformational Epitopes

As explained above, it is particularly preferred to use the modified MEFAs of the invention in immunoassays in combination with an epitope from the NS3/4a region. The NS3/4a region of the HCV polyprotein has been described and the amino acid sequence and overall structure of the protein are disclosed in, e.g., Yao et al., *Structure* (November 1999) 7:1353-1363; Sali et al., *Biochem*. (1998) 37:3392-3401; and Bartenschlager, R., *J. Viral Hepat*. (1999) 6:165-181. See, also, Dasmahapatra et al., U.S. Pat. No. 5,843,752, incorporated herein by reference ill its entirety. The subject immunoassays can utilize at least one conformational epitope derived from the NS3/4a region that exists in the conformation as found in the naturally occurring HCV particle or its infective product, as evidenced by the preservation of protease and, optionally, helicase enzymatic activities normally displayed by the NS3/4a gene product and/or by maintenance of the immunoreactivity of the antigen with antibodies in a biological sample from an HCV-infected subject, and a loss of the epitope's immunoreactivity upon denaturation of the antigen. For example, the conformational epitope can be disrupted by heating, changing the pH to extremely acid or basic, or by adding known organic denaturants, such as dithiothreitol (DTT) or an appropriate detergent. See, e.g., *Protein Purification Methods, a practical approach* (E. L. V. Harris and S. Angal eds., IRL Press) and the denatured product compared to the product which is not treated as above.

Protease and helicase activity may be determined using standard enzyme assays well known in the art. For example, protease activity may be determined using assays well known in the art. See, e.g., Takeshita et al., *Anal. Biochem*. (1997) 247:242-246; Kakiuchi et al., *J. Biochem*. (1997) 122:749-755; Sali et al., *Biochemistry* (1998) 37:3392-3401; Cho et al., *J. Virol. Meth*. (1998) 72:109-115; Cerretani et al., *Anal. Biochem*. (1999) 266:192-197; Zhang et al., *Anal. Biochem*. (1999) 270:268-275; Kakiuchi et al., *J. Virol. Meth*. (1999) 80:77-84; Fowler et al., *J. Biomol. Screen*. (2000) 5:153-158; and Kim et al., *Anal. Biochem*. (2000) 284:42-48. A particularly convenient assay for testing protease activity is set forth in the examples below.

Similarly, helicase activity assays are well known in the art and helicase activity of an NS3/4a epitope may be determined using, for example, an ELISA assay, as described in, e.g., Hsu et al., *Biochem. Biophys. Res. Commun.* (1998) 253: 594-599; a scintillation proximity assay system, as described in Kyono et al., *Anal. Biochem.* (1998) 257:120-126; high throughput screening assays as described in, e.g., Hicham et al., *Antiviral Res.* (2000) 46:181-193 and Kwong et al., *Methods Mol. Med.* (2000) 24:97-116; as well as by other assay methods known in the art. See, e.g., Khu et al., *J. Virol.* (2001) 75:205-214; Utama et al., *Virology* (2000) 273:316-324; Paolini et al., *J. Gen. Virol.* (2000) 81:1335-1345; Preugschat et al., *Biochemistry* (2000) 39:5174-5183; Preugschat et al., *Methods Mol. Med.* (1998) 19:353-364; and Resson et al., *Biochemistry* (2000) 39:2619-2625.

If a conformational NS3/4a epitope is used, the length of the antigen is sufficient to maintain an immunoreactive conformational epitope. Often, the polypeptide containing the antigen used will be almost full-length, however, the polypeptide may also be truncated to, for example, increase solubility or to improve secretion. Generally, the conformational epitope found in NS3/4a is expressed as a recombinant polypeptide in a cell and this polypeptide provides the epitope in a desired form, as described in detail below.

A representative amino acid sequence for an NS3/4a polypeptide is shown in FIGS. 13A through 13D. The amino acid sequence shown at positions 2-686 of FIGS. 13A through 13D corresponds to amino acid positions 1027-1711 of HCV-1. An initiator codon (ATG) coding for Met, is shown as position 1. Additionally, the Thr normally occurring at position 1428 of HCV-1 (amino acid position 403 of FIG. 13) is mutated to Pro, and the Ser normally occurring at position 1429 of HCV-1 (amino acid position 404 of FIG. 13) is mutated to Ile. This NS3/4a conformational epitope is termed "NS3/4a PI" and "NS3NS4a PI" herein. However, either the native sequence, with or without an N-terminal Met, the depicted analog (i.e., the "PI" analog), with or without the N-terminal Met, or other analogs and fragments can be used in the subject assays, so long as the epitope is produced using a method that retains or reinstates its native conformation. Dasmahapatra et al., U.S. Pat. No. 5,843,752 and Zhang et al., U.S. Pat. No. 5,990,276, both describe analogs of NS3/4a.

The NS3 protease of NS3/4a is found at about positions 1027-1207, numbered relative to HCV-1, positions 2-182 of FIG. 13. The structure of the NS3 protease and active site are known. See, e.g., De Francesco et al., *Antivir. Ther.* (1998) 3:99-109; Koch et al., *Biochemistry* (2001) 40:631-640. Changes to the native sequence that will normally be tolerated will be those outside of the active site of the molecule. Particularly, it is desirable to maintain amino acids 1- or 2-155 of FIG. 13, with little or only conservative substitutions. Amino acids occurring beyond position 155 will tolerate greater changes. Additionally, if fragments of the NS3/4a sequence are used, these fragments will generally include at least amino acids 1- or 2-155, preferably amino acids 1- or 2-175, and most preferably amino acids 1- or 2-182, with or without the N-terminal Met. The helicase domain is found at about positions 1193-1657 of HCV-1 (positions 207-632 of FIG. 13). Thus, if helicase activity is desired, this portion of the molecule will be maintained with little or only conservative changes. One of skill in the art can readily determine other regions that will tolerate change based on the known structure of NS3/4a.

As explained above, a number of antigens including epitopes derived from NS3/4a are known, including, but not limited to antigens derived from the c33c, c200, c100 and 5-1-1 regions, as well as fusion proteins comprising an NS3 epitope, such as c25.

For a description of these and various other HCV epitopes from other HCV regions, see, e.g., Houghton et al, U.S. Pat. No. 5,350,671; Chien et al., *Proc. Natl. Acad. Sci. USA* (1992) 89:10011-10015; Chien et al., *J. Gastroent. Hepatol.* (1993) 8:S33-39; Chien et al., International Publication No. WO 93/00365; Chien, D. Y., International Publication No. WO 94/01778; and U.S. Pat. Nos. 6,280,927 and 6,150,087, incorporated herein by reference in their entireties.

Production of HCV Antigens

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using $T_4$ DNA polymerase (Queen et al. (1989) *Proc. Natl. Acad. Sci. USA* 86:10029-10033) can be used under the invention to provide molecules having altered proteolytic cleavage sites and/or reduced protease susceptibility.

Methods for making MEFAs are known in the art and described in e.g., U.S. Pat. Nos. 6,428,792; 6,514,731; 6,632,601; 6,797,809, the disclosures of which are incorporated herein by reference in their entireties. Briefly, DNA encoding the desired epitopes for use in the MEFA is either synthetically produced or obtained from vectors including the same, as described above. Unique restriction enzyme sites can be introduced in order to connect the sequences encoding the epitopes in the prescribed order and enhance the usefulness of the invention by facilitating modifications in design of the MEFA. The choice of restriction enzyme sites and cloning procedures are readily determined by one of ordinary skill in the art of recombinant DNA technology. Preferably, the epitope junctions (amino acid sequences created between epitopes due to cloning) do not generate non-specific epitopes. Non-specific epitopes are, for example, non-HCV sequences which do not exist adjacent to the HCV epitopes in nature. Non-specific epitopes may bind antibodies in a test sample causing false positive assay results. To avoid non-specific interactions with the MEFA due to junction sequences, the DNA sequence encoding the junction may, for example, be mutated such that non-specific interactions with the mutant amino acid sequence are reduced, and cloning of the epitope fragments is possible. The nucleotide sequence is then placed within an expression cassette and a suitable host is transformed with the cassette. The host is allowed to express the sequences to provide the MEFA. The MEFA produced is then purified, for example, by affinity chromatography, which process is expedited to a certain degree due to the presence of the multiple copies of a given epitope.

Methods for producing mutants or analogs of the desired nucleotide sequence, such as HCV mutants, are well known. See, e.g., Dasmahapatra et al., U.S. Pat. No. 5,843,752 and Zhang et al., U.S. Pat. No. 5,990,276. Mutants or analogs of HCV antigens for use in immunoassays may be prepared by deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci. USA* 79:6409.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

As explained above, in order to facilitate recombinant expression, the coding sequence for the MEFA can be fused to another sequence, such as a fusion with, e.g., a sequence encoding the 50 kDa *E. coli* maltose binding protein, a fusion with a sequence encoding a yeast superoxide dismutase (SOD) or fragment thereof, or as a fusion with a sequence encoding ubiquitin. The nucleotide and amino acid sequences for human SOD are known and reported in Hallewell et al., U.S. Pat. No. 5,710,033.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The recombinant production of various HCV antigens, including antigens used in the various fusions described above, has been described. See, e.g., International Publication Nos. WO 94/01778, WO 93/00365, WO 04/00547 and WO 01/38360; U.S. Pat. Nos. 5,350,671, 5,683,864, 6,346,375, 6,150,087, 6,514,731, 6,428,792 and 6,632,601; Chien et al., *J. Gastroent. Hepatol.* (1993) 8:S33-39; Chien, D. Y., International Publication No. WO 94/01778; Chien et al., *Proc. Natl. Acad. Sci. USA* (1992) 89:10011-10015; the disclosures of all of which are incorporated herein by reference in their entireties.

Immunodiagnostic Assays

Once produced, the HCV antigens may be used in virtually any assay format that employs a known antigen to detect antibodies. A common feature of all of these assays is that the antigen is contacted with the body component suspected of containing HCV antibodies under conditions that permit the antigen to bind to any such antibodies present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules, as discussed in detail above. Assays which amplify the signals from the immune complex are also known; examples of which are assays which utilize biotin and avidin, and enzyme-labeled and mediated immunoassays, such as ELISA assays.

The immunoassay may be, without limitation, a heterogenous or a homogeneous format, and of a standard or competitive type. In a heterogeneous format, the antigen is typically bound to a solid matrix or support to facilitate separation of antigen-antibody complexes from the sample after incubation. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N—N'-bis-acryloyl-ethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

The antigen need not be bound directly to the solid support, but may be bound indirectly, e.g., through another binding molecule. For example, known antibodies that bind the antigen can be biotinylated and combined with a streptavidin- or avidin-coated solid support. The antigen of interest (e.g., a MEFA or NS3/4a conformational epitope) is attached to the solid support by binding to the biotinylated antibody. Alternatively, the antigen of interest can be biotinylated and combined with a streptavidin- or avidin-coated solid support.

If more than one HCV antigen is used in the assays, for example, a modified MEFA and a conformational NS3/4a epitope, the antigens can be provided on the same solid substrate or on different solid substrates that are combined in the assay. Thus, for example, the antigens can be present as discrete entities on, e.g., a plate, or can be present on, for example, individual microbeads that are added together for use in the assay of interest.

Figure 2:
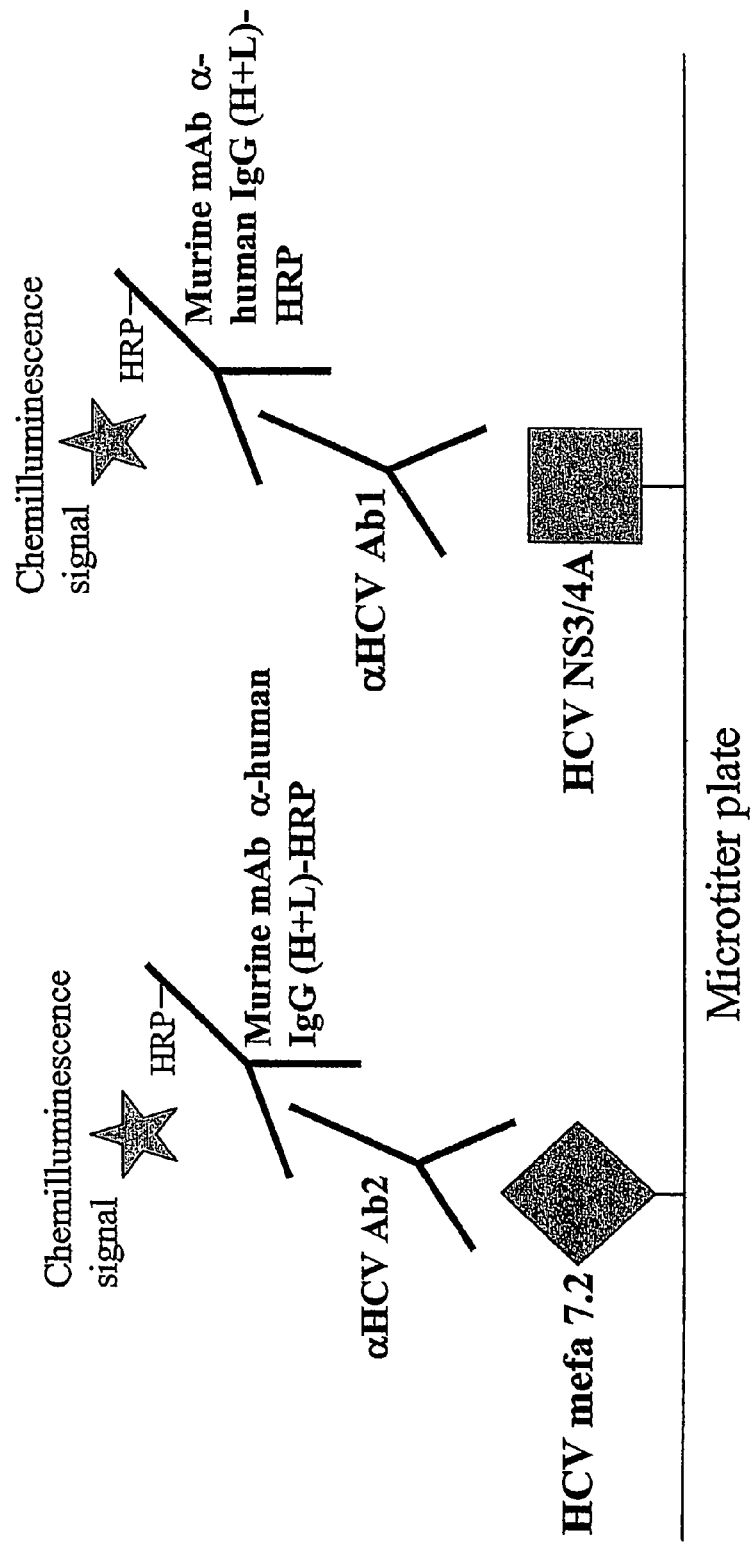
FIG. 2 is a schematic drawing of a representative immunoassay using a modified MEFA according to the invention where HCV antigens are immobilized on a solid support.

In one context, as depicted in FIG. 2, a solid support is first reacted with the HCV antigens e.g., HCV MEFA 7.2 and NS3/4a (collectively called "the solid-phase components" herein), under suitable binding conditions such that the molecules are sufficiently immobilized to the support. Sometimes, immobilization to the support can be enhanced by first coupling the antigen to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem.* 3:2-13; Hashida et al. (1984) *J. Appl. Biochem.* 6:56-63; and Anjaneyulu and Staros (1987) *International J. of Peptide and Protein Res.* 30:117-124.

After reacting the solid support with the solid-phase components, any nonimmobilized solid-phase components are removed from the support by washing, and the support-bound components are then contacted with a biological sample suspected of containing HCV antibodies (collectively called "ligand molecules" herein) under suitable binding conditions. If HCV antibodies are present in the sample, they will form a complex with the HCV antigens on the solid support. After washing to remove any nonbound ligand molecules, detectably labeled antibodies, such as anti-xenogenic (e.g., anti-human) antibodies, which recognize an epitope on anti-HCV antibodies, are added. These antibodies bind due to complex formation.

Figure 3:
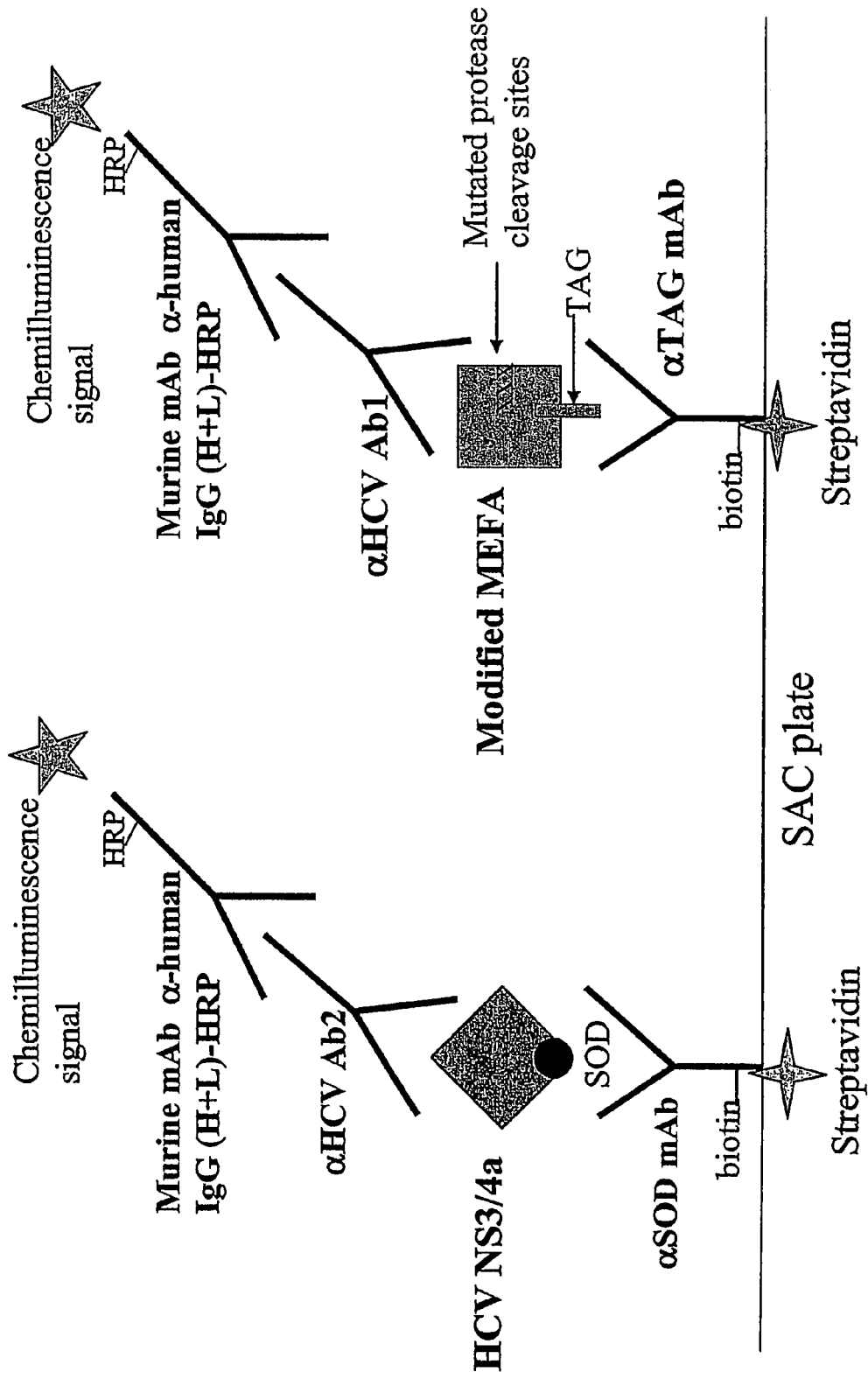
FIG. 3 is a schematic drawing of a representative immunoassay format using a modified MEFA with a streptavidin-coated solid support.

Another assay format is shown in FIG. 3. This assay format, well known in the art, uses a streptavidin-coated solid support reacted with biotin labeled antibodies that bind the modified MEFA and, optionally, NS3/4a, such as an NS3/4a conformational epitope. The sample is added under suitable binding conditions. If HCV antibodies are present in the sample, they will form a complex with the HCV antigens. After washing to remove any nonbound ligand molecules, detectably labeled antibodies are added, as described above.

In a homogeneous format, the test sample is incubated with the combination of antigens in solution. For example, it may be under conditions that will precipitate any antigen-antibody complexes which are formed. Both standard and competitive formats for homogeneous assays are also known in the art.

In a standard format, the amount of HCV antibodies forming the antibody-antigen complex is directly monitored. This may be accomplished by determining whether labeled antixenogenic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

More particularly, complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of anti-xenogeneic Ig complexed with a label, (e.g., an enzyme label). In an immunoprecipitation or agglutination assay format, the reaction between the HCV antigens and the antibody forms a network that precipitates from the solution or suspension and forms a visible layer or film of precipitate. If no anti-HCV antibody is present in the test specimen, no visible precipitate is formed.

In an alternative embodiment, the NS3/4a or modified MEFA can be used in a sandwich-type assay format as the detection agent. Sandwich assays are well known in the art.

The above-described assay reagents, including the immunoassay solid support with bound antibodies and antigens, as well as antibodies and antigens to be reacted with the captured sample, can be provided in kits, with suitable instructions and other necessary reagents, in order to conduct immunoassays as described above. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular immunoassay used, other packaged reagents and materials (i.e. wash buffers and the like). Various immunoassays, such as those described above, can be conducted using these kits.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Construction of MEFA 7.1 and MEFA 7.2

The following example illustrates the preparation of a polyprotein cassette of multiple HCV epitopes. The polyprotein expressed from the multiple epitope cassette is referred to herein as a Multiple Epitope Fusion Antigen (MEFA). Preferably, where an epitope is repeated, the extra copy or copies are tandemly arrayed in the same orientation. It is understood that the region of a viral coding sequence used as an epitope may be varied slightly and still retain antigenic activity, and that the amino acid numbering designation may vary from strain to strain. Thus, the repeated epitopes may vary one from another in amino acid sequence due to strain sequence variations and/or numbering designation. Preferably, the amino acid sequences of repeated epitopes within a MEFA are at least 30% homologous at the amino acid level, more preferably at least 40% homologous at the amino acid level.

Unique restriction enzyme sites were introduced in order to connect the epitopes in the prescribed order and enhance the usefulness of the invention by facilitating modifications in design of a chimeric antigen. The choice of restriction enzyme sites and cloning procedures are readily determined by one of ordinary skill in the art of recombinant DNA technology. Preferably, the epitope junctions (amino acid sequences created between epitopes due to cloning) do not generate non-specific epitopes. Non-specific epitopes are, for example, non-HCV sequences which do not exist adjacent to the HCV epitopes in nature. Non-specific epitopes may bind antibodies in a test sample causing false positive assay results. Preferably, the multiple epitope fusion protein is tested for false positive results due to such sequences generated at the epitope junctions. To avoid non-specific interactions with the MEFA due to junction sequences, the DNA sequence encoding the junction may, for example, be mutated such that non-specific interactions with the mutant amino acid sequence are reduced, and cloning of the epitope fragments is possible.

Figure 4:
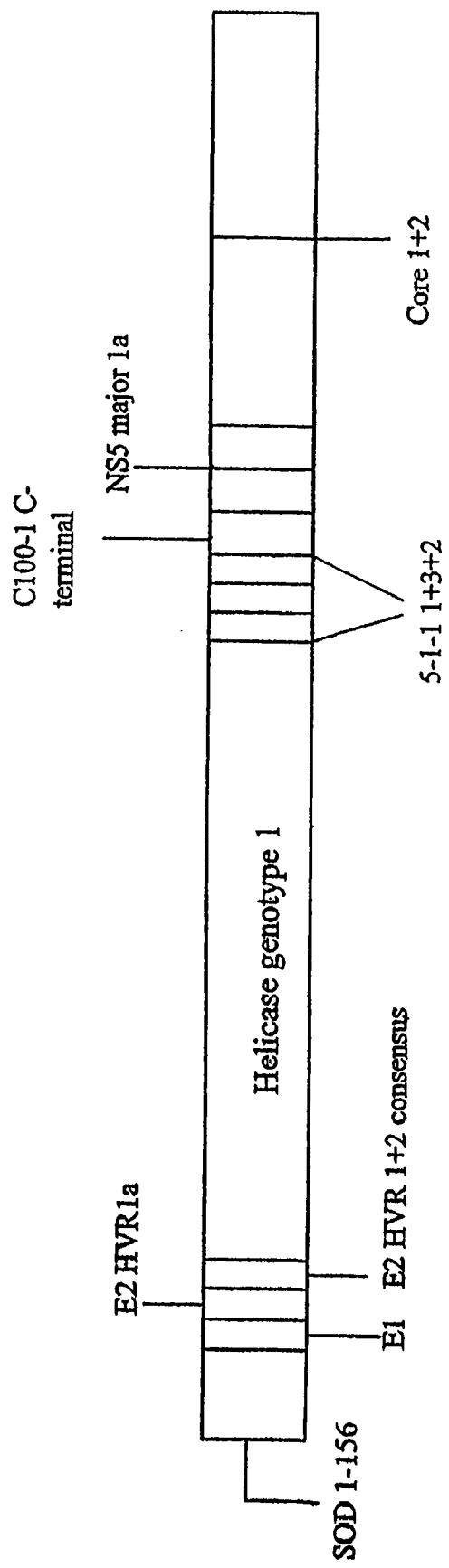
FIG. 4 is a diagrammatic representation of MEFA 7.1.
Figure 8:
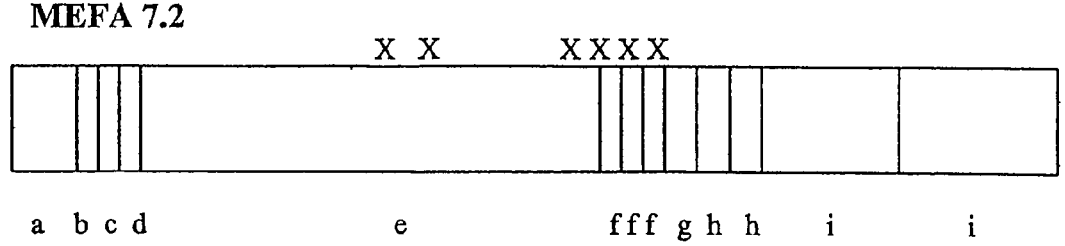
FIG. 8 is a diagrammatic representation of MEFA 7.2

The HCV MEFA 7.1 and 7.2 expression cassettes were constructed by cloning the coding nucleotide sequences containing major epitopes in a tandem array as shown in, e.g., FIGS. 4 and 8 that show diagrammatic representations of MEFA 7.1 and 7.2, respectively. A major epitope was chosen based on antibody reaction frequency and reaction intensity (titer) to the epitope (Chein, D. Y. et al. (1994) Viral Hepatitis and Liver Disease, pp. 320-324). The various DNA segments coding for the HCV epitopes were constructed by PCR amplification or by synthetic oligonucleotides. The amino acids in each segment of MEFA 7.2 are set forth in Table 2 above and shown in FIGS. 9A-9F. The complete HCV-1 amino acid sequence (3011 amino acids) was determined by Choo, et al. (1991) *Proc. Natl. Acad. Sci. USA* 88:2451-2455, herein incorporated by reference in its entirety. Oligonucleotides capable of binding to HCV are described in U.S. Pat. No. 5,350,671, herein incorporated by reference in its entirety. The numbering of the amino acids in epitopes of the invention follows the numbering designation provided in Choo, et al., supra, in which amino acid number 1 is the first methionine encoded by the coding sequence of the core region, unless otherwise specified. For example, one epitope segment from NS5 is represented by amino acids 2278 to 2313 of the HCV polyprotein. An epitope from the E1 region is represented by amino acids 303 to 320, numbered relative to the HCV-1 polyprotein. MEFAs 7.1 and 7.2 each contain epitopes from HCV-1, HCV-2 and HCV-3, allowing for detection of multiple types of a virus in a single assay. Methods of determining HCV serotype are found in WO 96/27153, herein incorporated by reference in its entirety. For example, epitopes from the 5-1-1 region have been found to vary between serotypes of HCV. A copy of each of the HCV type-specific 5-1-1 epitopes present in the MEFAs described herein allows binding of any of the HCV types that may be present in the test biological sample.

The MEFA constructs were genetically engineered for expression in *Saccharomyces cerevisiae*, utilizing the yeast expression vector pBS24.1 which contains 2μ sequences for autonomous replication in yeast and the yeast genes leu2-d and URA3 as selectable markers. The β-lactamase gene and the ColE1 origin of replication, required for plasmid replication in bacteria, were also present in this expression vector. The yeast expression vector for MEFA 7, ps.MEFA7, was constructed first. Subsequently, the plasmid was modified in the coding region for the HCV core epitopes to create the plasmid ps.MEFA7.1, encoding the MEFA 7.1 antigen. Finally, the MEFA 7.2 antigen was created by mutating the NS3 proteolytic cleavage sites present at amino acid positions 1428/1429, 1455/1456, 1657/1658 and 1711/1712 (in the 5-1-1 epitope, present as three repeats).

In particular, as shown in FIGS. 6A-6D, a yeast expression plasmid for MEFA 7 was constructed as follows. First, a BamHI/HindIII fragment of 1896 bp, encoding the ADH2/GAPDH hybrid promoter, hSOD (human SOD, amino acids 1-156), followed by an E1 epitope (amino acids 303-320, HCV1 strain), was isolated from ps.MEFA6, the expression plasmid encoding MEFA 6 (FIG. 12C), described in International Publication No. WO 97/44469. Next, a HindIII/SphI synthetic DNA fragment of 269 bp which contains the coding sequence for E2 HVR1a consensus epitope (amino acids 390-410, HCV-1), E2 HVR1+2 consensus epitope (amino acids 384-414, HCV1+2) and the 5' end of the helicase domain (amino acids 1193-1229, HCV-1) was created. An SphI/EclXI fragment of 1264 bp, encoding the remainder of the helicase domain (amino acids 1230-1651, HCV-1), was gel-purified from pTac5/HeII plasmid DNA. The HindIII/SphI synthetic DNA fragment and the SphI/EclXI 1264 bp fragment were ligated into vector pSP72new.HindIII/EclXI vector, to produce pSP72new.HindIII/EclXI/e2.helicase. This vector was derived from pSP72 an *E. coli* vector commercially available from Promega, Madison, Wis. (see, GenBank/EMBL Accession Number X65332). In particular, to facilitate the subcloning of several MEFA 7 epitopes, a new multiple cloning site (MCS) polylinker was introduced, via synthetic oligos, between the SphI and BglII sites of pSP72. This new plasmid, named pSP72new, was digested with HindIII and EclXI (also known as EagI), which have unique sites in the MCS. It was then dephosphorylated and gel-purified.

*E. coli* HB101 competent cells were transformed with the plasmid, and plated on Luria agar plates containing 100 μg/ml ampicillin. Desired clones were identified using miniprep DNA analysis. After sequence verification, the plasmid pSP72new.HindIII/EclXI/e2.helicase subclone #4 was digested with HindIII and EclXI(EagI) to generate a 1534 bp fragment. The HindIII/EclX1 fragment was gel-purified and ligated with EclXI/SphI oligonucleotides, encoding the last amino acids of the helicase domain (amino acids 1651-1658, HCV-1), into a pGEM7 HindIII/SphI vector. HB101 competent cells were transformed and plated on Luria-ampicillin (100 μg/ml). After identification of the desired clones and sequence confirmation, pGEM7HindIII/SphI subclone #9 was digested with HindIII and SphI to generate a 1560 bp fragment, which was gel purified (see, FIG. 6A).

To assemble the 3' end portion of MEFA 7, the following steps were performed. The 5-1-1 epitopes (amino acids 1689-1735) from HCV-1, HCV-3 and HCV-2 (in this order) were gel-isolated from ps.MEFA6, the expression plasmid encoding MEFA 6, described in International Publication No. WO 97/44469, as an SphI/AvaI fragment of 441 bp. This fragment was ligated with synthetic AvaI/XbaI oligonucleotides encoding the c100 epitope (amino acids 1901-1936) into a pSP72new.SphI/XbaI vector. After HB101 transformation, clone identification, and sequence verification, pSP72newSXi subclone #6 was digested with XbaI and NotI to prepare a pSP72newXbaI/NotI vector. Additionally, an XbaI/NcoI fragment of 221 bp, which encoded a double repeat of an NS5 epitope (amino acids 2278-2313, HCV-1), was isolated from ps.MEFA6. The XbaI/NcoI fragment was ligated with NcoI/NotI oligonucleotides, encoding the first amino acids of the HCV-1 core epitope, amino acids 9-17, in which the Lys at position 9 was changed to Arg, and the Asn at position 11 was changed to Thr, into the pSP72newXbaI/NotI vector prepared above. HB101 transformants were analyzed and their plasmid DNA sequenced. A subclone, termed pSP72newSX/XNi #3, was digested with NotI/SalI to prepare a vector for subsequent subcloning (see, FIG. 6B).

To complete the assembly of the 3' end of MEFA 7, a double repeat of the sequence encoding a core epitope with amino acids 9-53 from HCV-1, plus two genotype-specific epitopes of the core region (amino acids 64-88, HCV-1 and amino acids 67-84, HCV-2) were subcloned as follows into NotI-SalI digested pSP72newSX/XNi subclone #3. First, a NotI/XmnI fragment of 92 bp encoding amino acids 18-51 of a core epitope was isolated from pd.Core191RT clone #20. Plasmid pd.Core191RT was constructed by ligating into the pBS24.1 BamHI-SalI yeast expression vector, a 1365 bp BamHI-NcoI fragment for the ADH2/GAPDH promoter, and a 615 bp NcoI-SalI fragment encoding the first 191 amino acids of HCV-1 core with amino acid 9 mutated from Lys to Arg and amino acid 11 mutated from Asn to Thr. The 615 bp NcoI-SalI fragment was derived from an *E. coli* expression vector in which the core sequence for amino acids 1-191, with the same two mutations described above, had been cloned.

The 92 bp NotI/XmnI fragment was ligated with a pSP72newNot/Kpn vector and with XmnI/KpnI oligonucleotides which encode the 3' end of the complete core epitope. After sequence verification of the positive clones, pSP72newNKi subclone #4 was digested with NotI and KpnI, and a 224 bp fragment was gel-isolated. This NotI/KpnI fragment was ligated with 284 bp of oligonucleotides (KpnI-SalI ends) encoding a complete repeat of the core epitope described above into the pSP72newSX/XNi NotI/SalI vector described above. After HB101 transformation, clone identification and sequence verification, pSP72newSX/N/NSi subclone #18 was digested with SphI and SalI and a fragment of 1317 bp was gel-isolated (see, FIG. 6C).

Figure 6A:
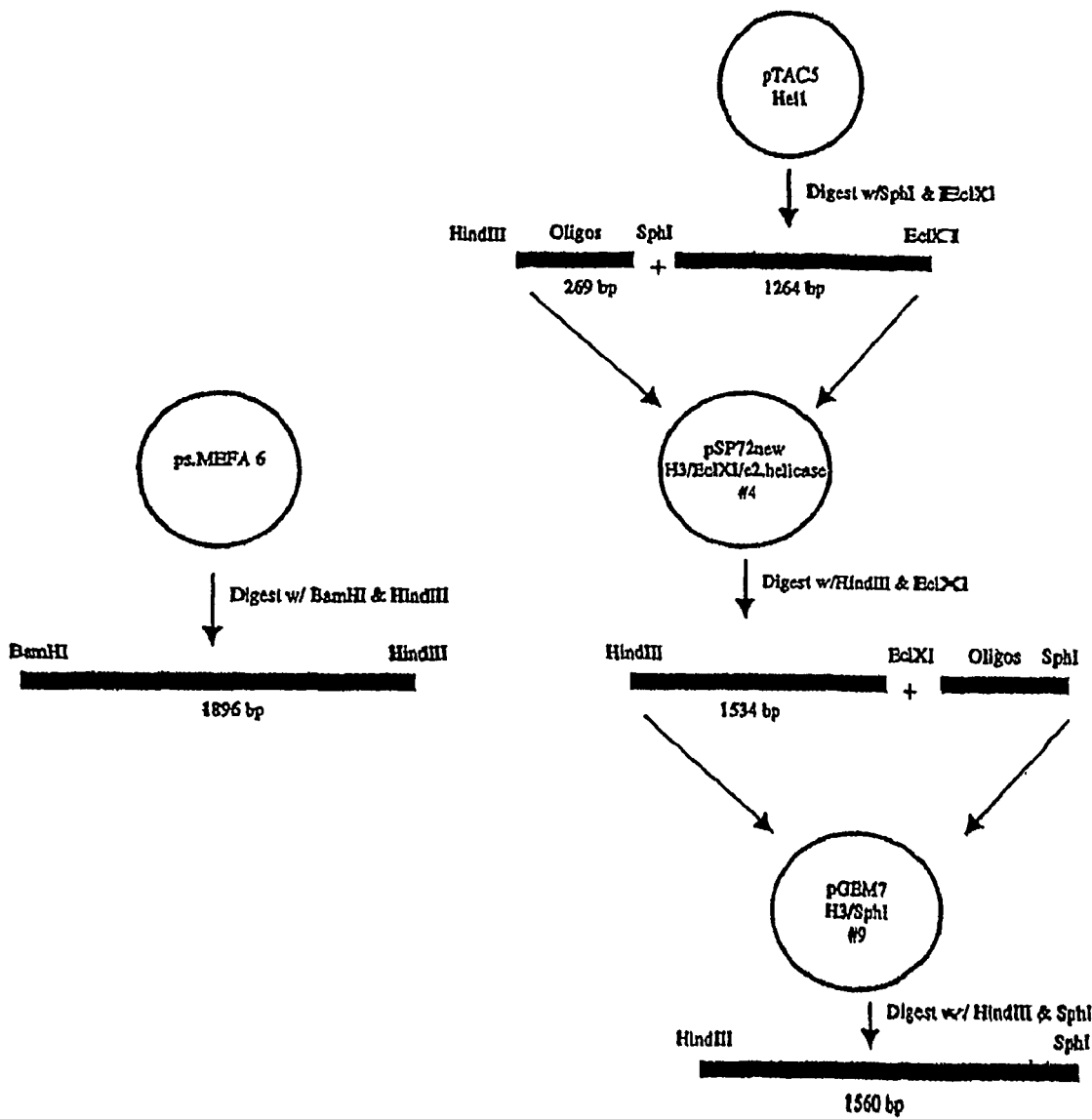
FIGS. 6A-6D are diagrams of the construction of psMEFA7.
Figure 6B:
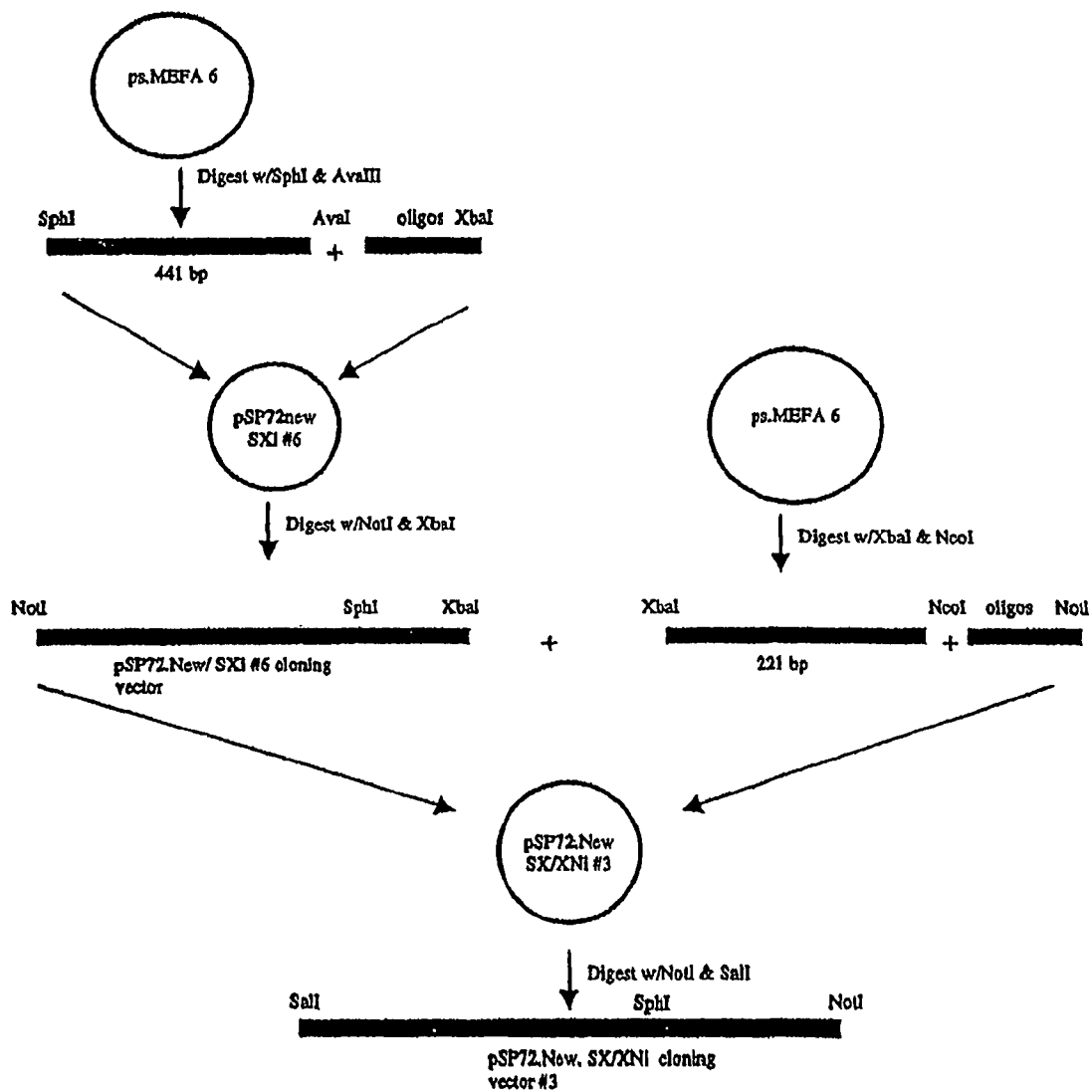
Figure 6C:
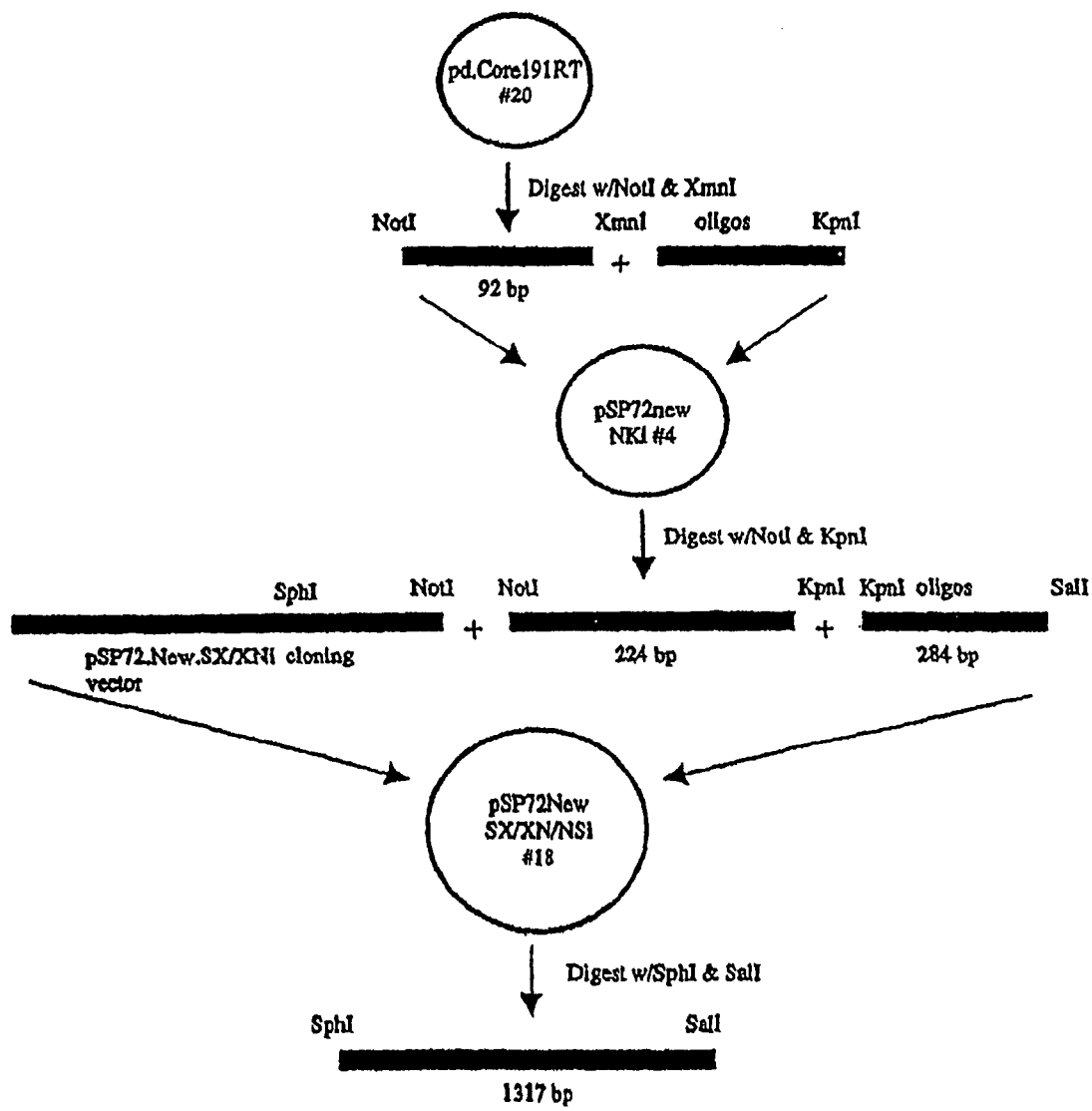
Figure 6D:
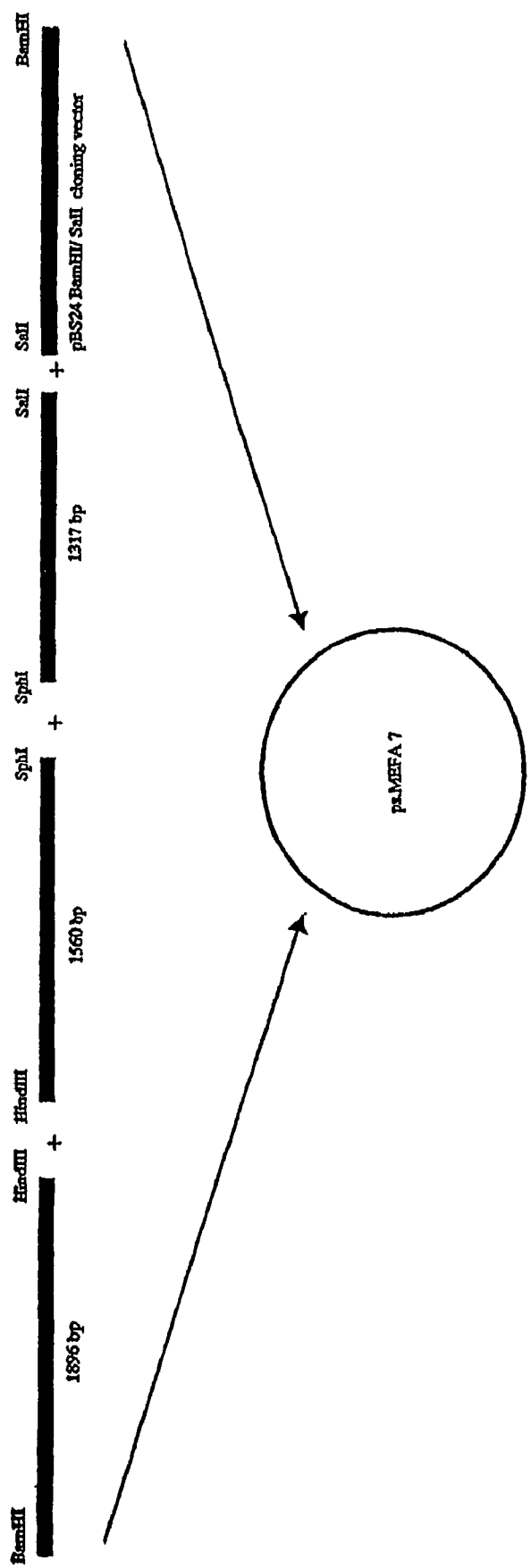
Figure 7:
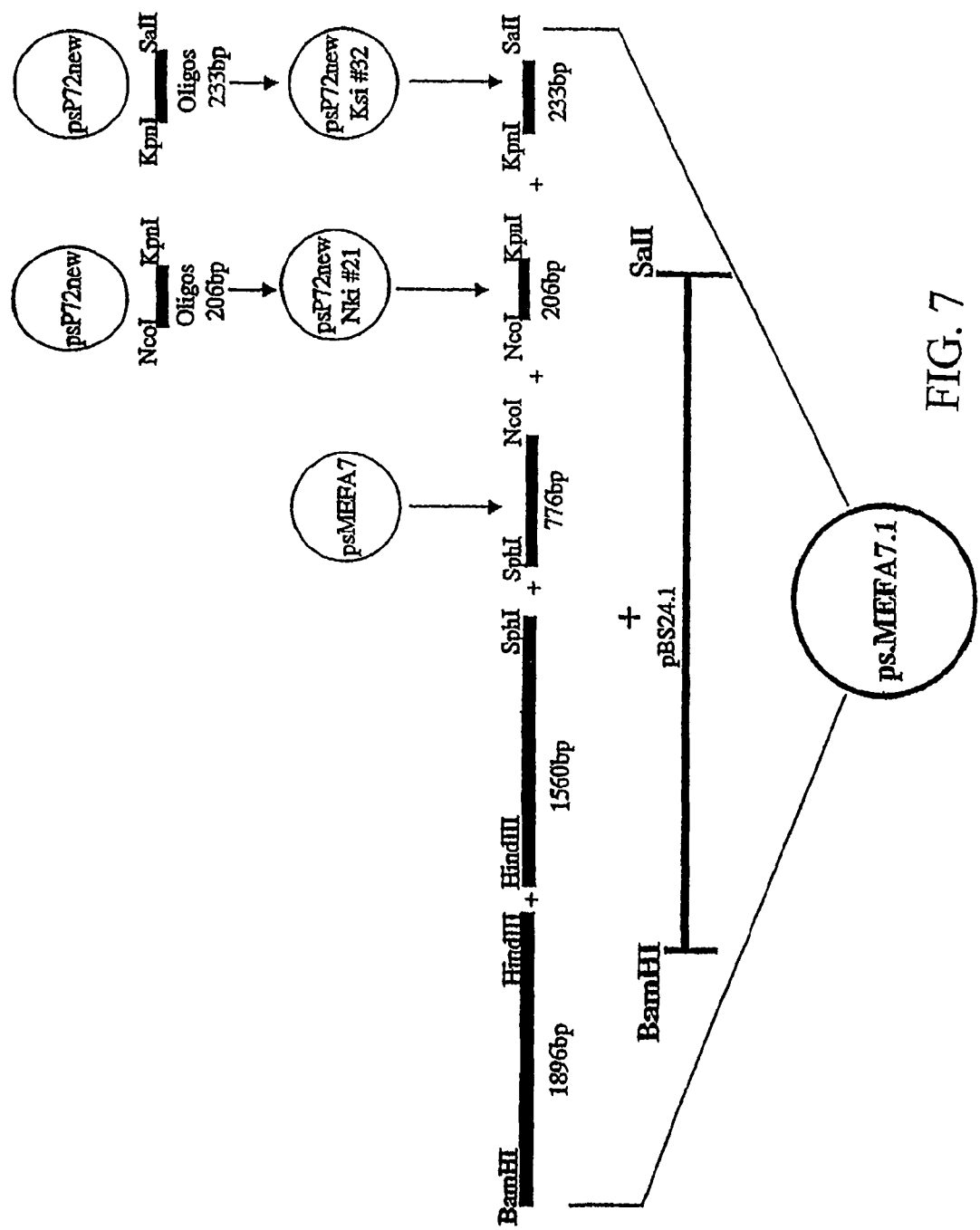
FIG. 7 is a diagram of the construction of psMEFA7.1.

Lastly, the following fragments, described above, were ligated into the pBS24.1 BamHI/SalI yeast expression vector to create ps.MEFA7 (see, FIG. 6D):

the BamHI/HindIII fragment of 1896 bp (FIG. 6A)
the HindIII/SphI fragment of 1560 bp (FIG. 6A)
the SphI/SalI fragment of 1317 bp (FIG. 6C)

*S. cerevisiae* strain AD3 was transformed with ps.MEFA7 and single transformants were checked for expression after depletion of glucose in the medium. The recombinant protein was expressed at high levels in yeast, as detected by Coomassie blue staining. In particular, yeast cells were transformed with the MEFA expression plasmid using a lithium acetate protocol. Ura⁻ transformants were streaked for single colonies and patched onto Leu⁻/8% glucose plates to increase plasmid copy number. Leu⁻starter cultures were grown for 24 hours at 30° C. and then diluted 1:20 in YEPD (yeast extract bactopeptone 2% glucose) media. The cells were grown for 48 hours at 30° C. and harvested. To test for expression of the MEFA 7 recombinant antigen, an aliquot of the cells was lysed with glass beads in lysis buffer (10 mM Tris-Cl pH 7.5, 1 mM EDTA, 10 mM DTT). The lysate was centrifuged at high speed. The supernatant and insoluble pellet were analyzed on SDS protein gels. MEFA 7 was highly enriched in the insoluble pellet fraction.

The MEFA 7 antigen was purified as follows. *S. cerevisiae* cells expressing MEFA 7 were harvested as described above. The cells were suspended in lysis buffer (50 mM Tris, 0.15 M NaCl, 1 mM EDTA, 1 mM PMSF, pH 8.0) and lysed in a Dyno-Mill (Wab Willy A. Bachofon, Basel, Switzerland) or equivalent apparatus using glass beads. The lysate was centrifuged at low speed conditions (3,000 to 5,000 rpm, 15 min) and the pellet containing the insoluble protein fraction was washed with increasing concentrations of urea (1 M, 2 M, 3 M) in lysis buffer. Protein was solubilized from the centrifugation pellet with 0.1 N NaCl, 4 M urea in lysis buffer. Cell debris was removed by low speed centrifugation at 3,000 to 5,000 rpm, 15 min. The supernatant was adjusted to pH 8.0 with 6 N HCl to precipitate proteins insoluble under these conditions.

The precipitate was removed by centrifugation and the supernatant was adjusted to 2.3% SDS, 50 mM DTT, pH 8.0 and boiled for 3 min. Proteins in the mixture were fractionated by gel filtration on a Pharmacia Sephacryl S-400 in phosphate buffered saline containing 0.1% SDS, 1 mM EDTA and adjusted to pH 7.4. Column eluate fractions containing MEFA 7 were collected, pooled, and concentrated on an Amicon YM-30 membrane. Gel filtration was repeated on the pooled fractions using the same column and conditions.

During the analysis of MEFA 7 in a trial assay, it was discovered that a monoclonal antibody used as a detection conjugate reacted with a specific sequence of the core epitope (amino acids 33-38). Thus, ps.MEFA7.1 was designed to eliminate amino acids 33-38 from the core epitope region.

Figure 11A:
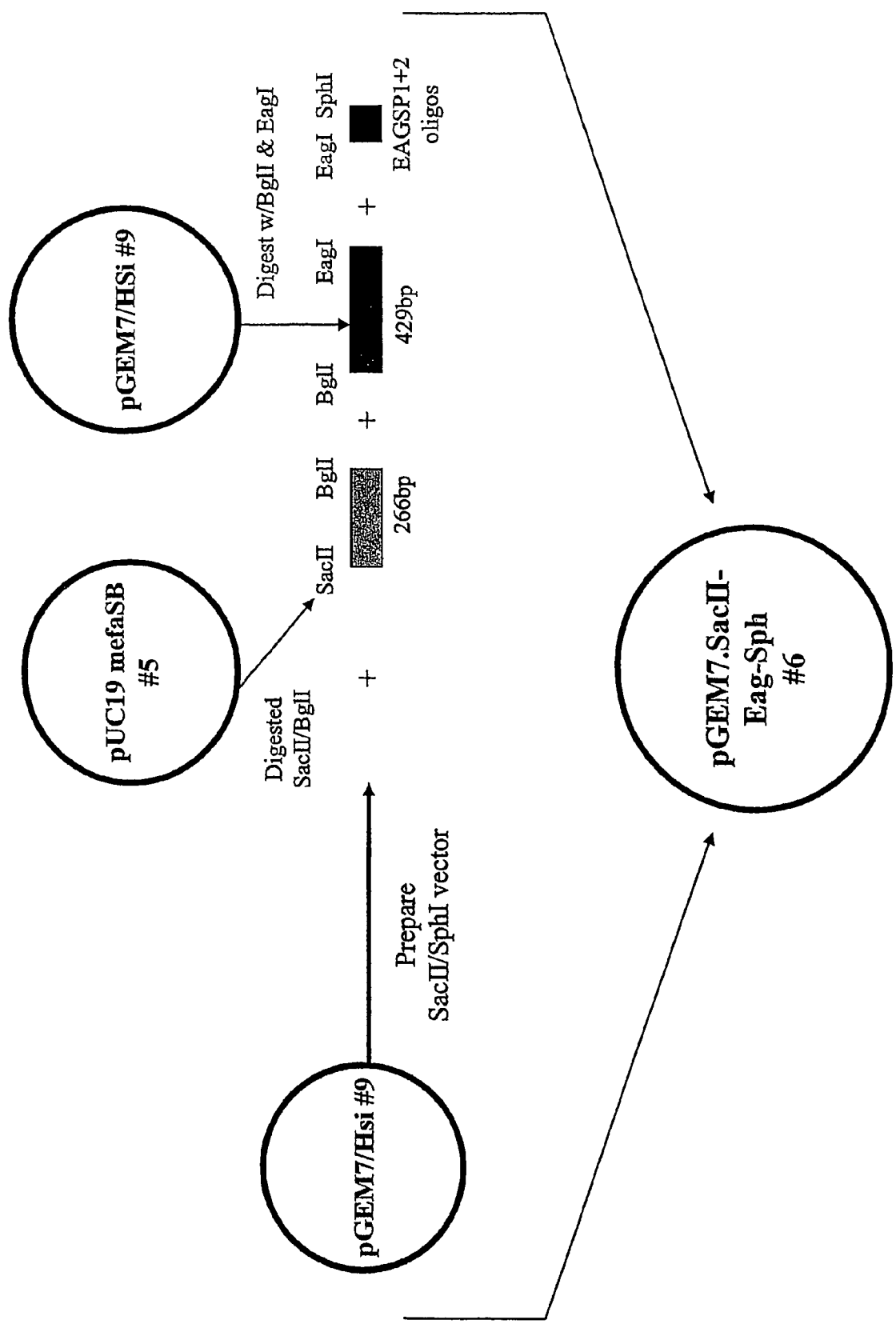
FIGS. 11A-11C are diagrams of the construction of ps.mefa7.2.
Figure 11B:
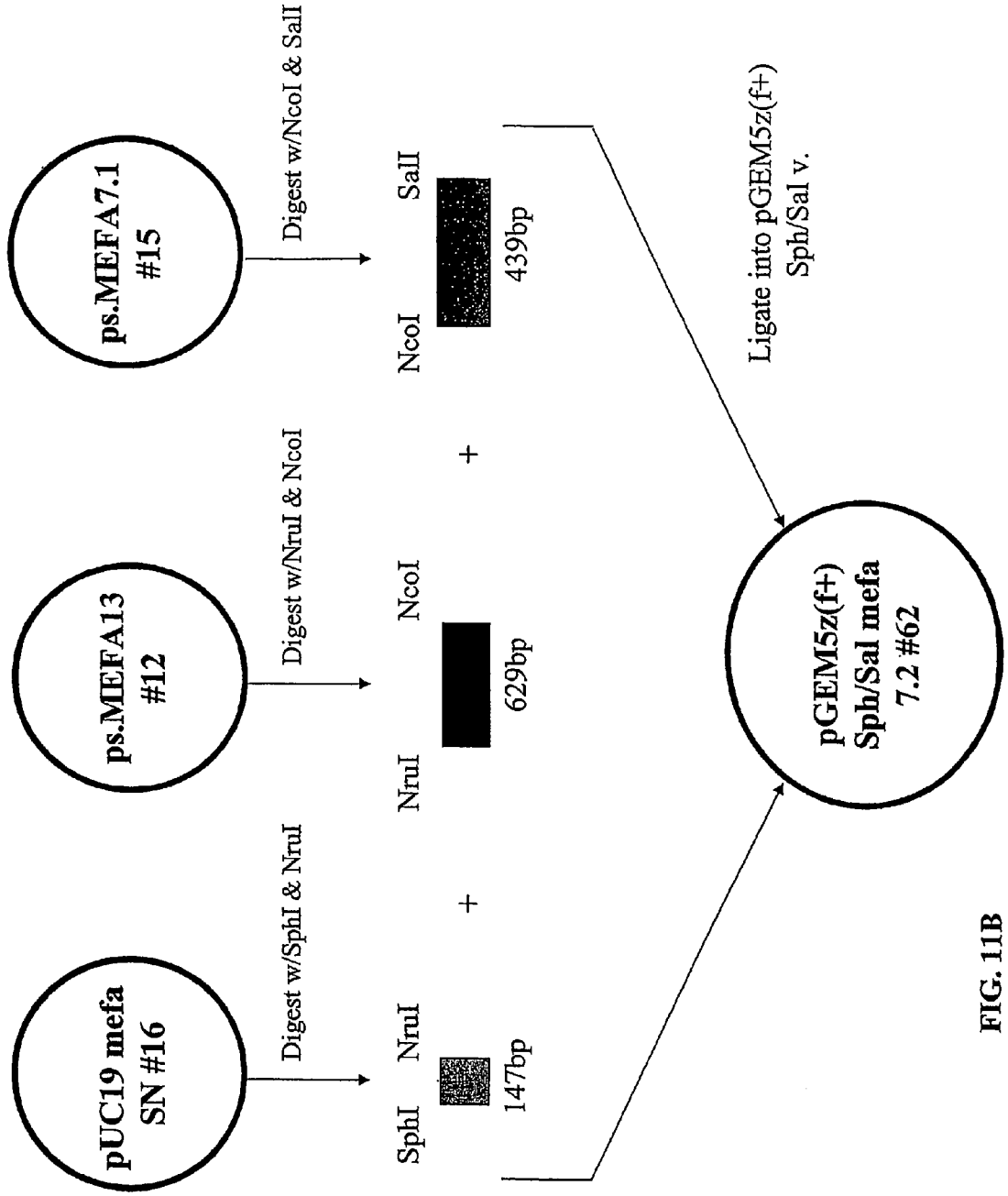

A yeast expression vector for MEFA 7.1 was made as follows. First, the double repeat of the core epitope at the 3' end of ps.MEFA7 was modified. To do so, an NcoI/KpnI synthetic fragment of 206 bp, encoding the first core epitope repeat (amino acids 9-32, 39-42 and 64-88 of HCV-1, and amino acids 67-82 of HCV-2), and a KpnI/SalI synthetic fragment of 233 bp encoding amino acids 83 and 84 of HCV-2, followed by the second core epitope repeat (amino acids 9-32, amino acids 39-42 and amino acids 64-88, HCV-1, amino acids 67-84, HCV-2) were subcloned respectively into a pSP72new.NcoI/KpnI vector and a pSP72new.KpnI/SalI vector. After HB101 transformation, clone identification and sequence confirmation, pSP72newNKi clone #21 was digested with NcoI and KpnI to isolate the NcoI/KpnI fragment of 206 bp and pSP72newKSi clone #32 was digested with KpnI and SalI to isolate the KpnI/SalI fragment of 233 bp.

Plasmid ps.MEFA7.1 was assembled by ligating the following fragments into the pBS24.1 BamHIII/SalI yeast expression vector (see, FIG. 7):

the BamHIII/HindIII fragment of 1896 bp, described above for ps.MEFA7;

the HindIII/SphI fragment of 1560 bp described above for ps.MEFA7;

an SphI/NcoI fragment of 776 bp isolated from ps.MEFA7 encoding the 5-1-1 epitopes, c100 epitope and NS5 epitope;

the NcoI/KpnI fragment of 206 bp;

and KpnI/SalI fragment of 233 bp.

*S. cerevisiae* strain AD3 was transformed with ps.MEFA7.1 and single transformants were checked for expression after depletion of glucose in the medium, as described above. The recombinant protein was expressed at high levels in yeast, as detected by Coomassie blue staining.

The MEFA 7.1 antigen was purified as follows. *S. cerevisiae* cells expressing MEFA 7.1 were harvested as described above. The cells were suspended in lysis buffer (50 mM Tris, 0.15 M NaCl, 1 mM EDTA, pH 8.0) and lysed in a Dyno-Mill (Wab Willy A. Bachofen, Basel, Switzerland) or equivalent apparatus using glass beads. The lysate was centrifuged at 10,000 rpm, 30 min in a JA-10 rotor, and the pellet containing the insoluble protein fraction was washed with increasing concentrations of Urea (1 M, 2 M, 3 M) in lysis buffer. Protein was solubilized from the centrifugation pellet with 0.1 N NaCl, 4 M Urea, 50 mM DTT in lysis buffer. Cell debris was removed by centrifugation at 14,000 rpm, 20 min in a JA-14 rotor. The supernatant was adjusted to pH 8.0 with 6 N HCl to precipitate proteins insoluble under these conditions.

The precipitate was removed by centrifugation at 14,000 rpm, 20 min in a JA-14 rotor. The supernatant was adjusted to 2.3% SDS and heated to 70-75° C. in boiling water then cooled to room temperature. Proteins in the mixture were fractionated by gel filtration on a Pharmacia Sephacryl S-400 HR in PBS containing 0.1% SDS, 1 mM EDTA and adjusted to pH 7.4. Column eluate fractions containing MEFA 7.1 were collected, pooled, and concentrated on an Amicon YM-30 membrane. Pooled gel filtration fractions were adjusted to 2.3% SDS, 50 mM DTT, and heated/cooled as above. This pool was subjected to a second gel filtration step on a Pharmacia Sephacryl S-300 HR column under the same conditions as the first gel filtration step.

A yeast expression vector for MEFA 7.2 was made as follows. For ease in cloning this large multiple epitope fusion antigen, the molecule was divided into three restriction fragments. First, a BamHI-HindIII fragment of 1896 bp was gel-purified from ps-mefa7.1 (described above). This fragment encoded the ADH2/GAPDH promoter, human SOD, and the E1 epitope of HCV-1.

The next fragment, a HindIII-SphI fragment of 1560 bp, encoding the E2 HVR-1a consensus, the E2 HCV1+2 consensus, and the helicase domain (HCV-1, amino acids 1193-1658, with mutations at amino acids 1428, 1429, 1455, 1456, 1657 and 1658, to eliminate protease cleavage sites), was subcloned into a pGEM7 vector. In particular, the coding sequence was mutated such that each of the naturally occurring amino acids at positions 1428, 1455 and 1657 were substituted with a leucine, and each of the naturally occurring amino acids at positions 1429, 1456 and 1658 were substituted with a proline. Hence, the mutation at each of the above pairs is termed "LP" herein. This subclone was derived as follows from pGEM7HindIII/SphI subclone #9 (termed "pGEM7/HSi #9" and described above): (1) pGEM7HindIII/SphI subclone #9, which contains a 1560 bp HindIII-SphI insert, was digested with SacII+SphI, dephosphorylated, and gel-purified, thereby removing the 721 bp of helicase in which the three protease cleavage sites were located. (2)

Synthetic oligos were used to clone the 266 bp SacII-BglI portion of helicase containing the first two LP mutations. To facilitate the cloning, the oligos contained EcoR1 and SalI sites at the 5-prime and 3-prime ends, respectively. The oligos were cloned into a pUC19 EcoRI-SalI vector. After HB101 transformation and sequence verification of positive clones, pUC19 mefaSB #5 was amplified and the 266 bp SacII-BglI fragment gel-purified. (3) A 429 bp BglI-EagI fragment was gel-purified from pGEM7HindIII/SphI subclone #9. There are no mutations in this region of helicase. (4) To complete the 26 bp EagI-SphI portion of helicase, which contains the third mutation, two additional oligos were used. (5) The 266 bp SacII-BglI fragment, the 429 bp BglI-EagI fragment, and these two oligos were ligated into the pGEM7HindIII/SphI subclone #9 vector. From one of the resultant HB101 clones, named pGEM7/SacII-EagI-SphI #6 (FIG. 11A), the 1560 bp HindIII-SphI fragment was gel-purified for MEFA 7.2.

The third restriction fragment needed for MEFA 7.2, a 1215 bp SphI-SalI fragment encoding the 5-1-1 domains for HCV 1,2,3, each with a PI mutation at a protease cleavage site, C100 epitope, NS5 epitope in duplicate, and core epitopes in duplicate, was subcloned as follows: (1) The 5-1-1 PI epitope for HCV-1 was cloned with synthetic oligos into a pUC19 EcoR1-SalI vector. The oligos contained SphI and NruI sites adjacent to the EcoR1 and SalI cloning sites, respectively. After HB101 transformation and sequence verification of the positive clones, pUC19 mefaSN #16 was amplified and the 147 bp SphI-NruI insert gel-purified. (2) A 629 bp NruI-NcoI fragment encoding 5-1-1PI for HCV-3 and HCV-2, C100, and the NS5 repeats, was gel-purified from ps.mefa13 #12 (described in U.S. Pat. No. 6,630,298, incorporated herein by reference in its entirety). (3) A 439 bp NcoI-SalI fragment encoding the two repeats of core epitopes was gel-purified from ps.mefa7.1 #15. (4). The 147 bp SphI-NruI fragment, the 629 bp NruI-NcoI fragment, and the 439 bp NcoI-SalI fragment were ligated into a pGEM5 SphI-SalI vector. From one of the resultant clones, pGEM5 SphI-SalI.mefa7.2 #62 (FIG. 11B), the 1215 bp SphI-SalI insert was gel-isolated.

Figure 11C:
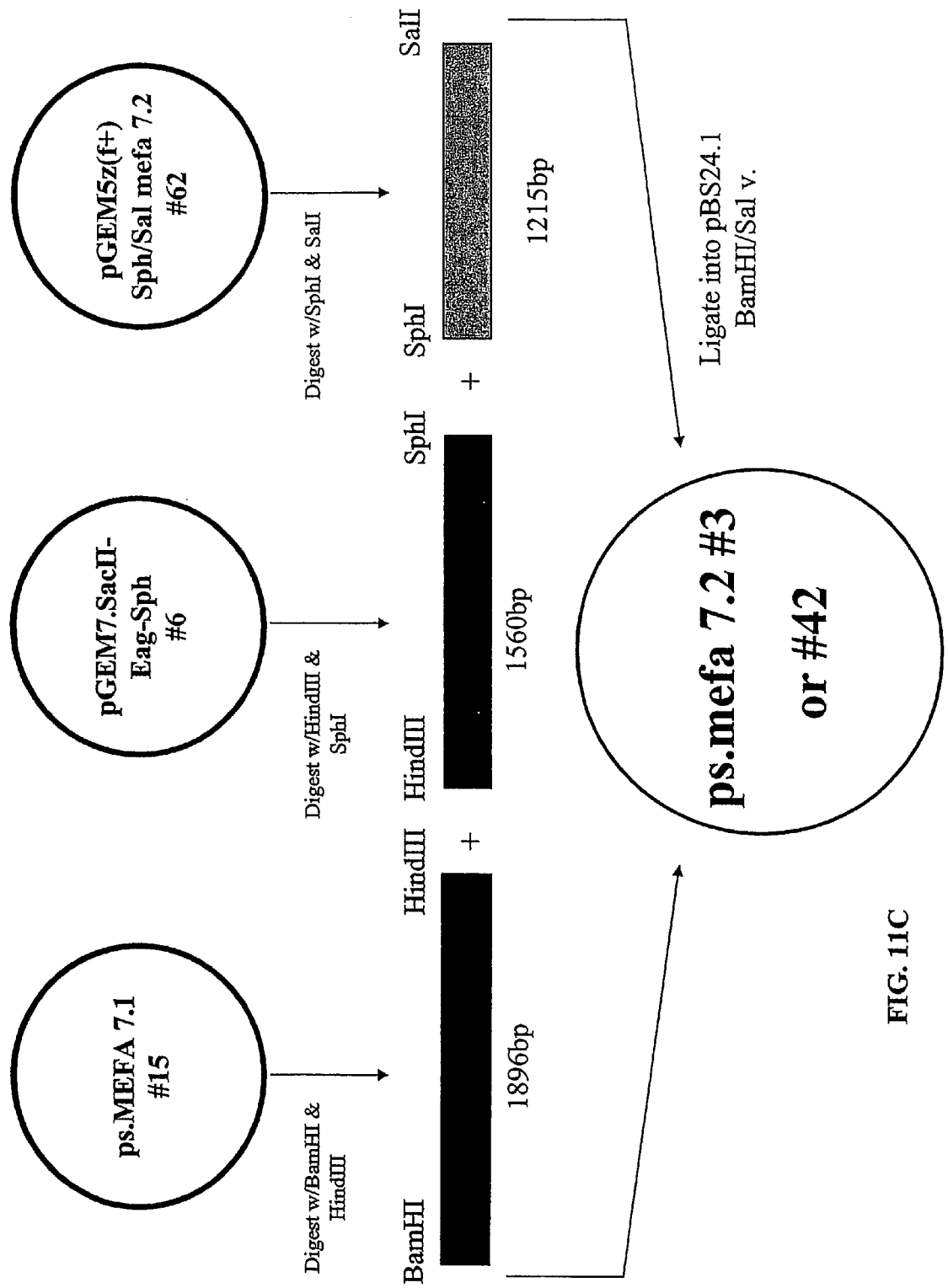

Lastly, the 1869 bp BamHI-HindIII fragment, the 1560 bp HindIII-SphI fragment, and the 1215 bp SphI-SalI fragment were ligated into the BamHI-SalI pBS24.1 yeast expression vector. After HB101 transformation and miniscreen analysis, two positive clones were found to have the correct size BamHI-SalI insert. Plasmid DNA was amplified for ps.mefa7.2 #3 and #42 (FIG. 11C).

S. cerevisiae strain AD3 was transformed with ps.mefa7.2 using the Invitrogen Easy Comp Sc transformation kit (Invitrogen, San Diego Calif.). Ura-transformants were streaked for single colonies and patched onto leu48% glucose plates to increase plasmid copy number. Leu-starter cultures were grown for 24 hours at 30° C. and then diluted 1:20 in YEPD (yeast extract bactopeptone 2% glucose) media. Cells were grown for 48 hours at 30° C. and harvested. To test for expression of the recombinant protein, aliquots of cells were lysed with glass beads in lysis buffer (10 mM Tris-Cl pH 7.5, 1 mM EDTA, 10 mM DTT). The lysates were cleared by centrifugation at high speed. The insoluble pellet fractions were analyzed by Coomassie staining of SDS protein gels. The 120 kDa MEFA 7.2 protein was highly expressed.

The presence of MEFAs were confirmed using SDS-PAGE (4-20% Tris-glycine gel) and Western blot, using a monoclonal antibody directed against h-SOD, since each of the MEFAs above included amino acids 1-156 of human SOD.

The DNA and corresponding amino acid sequence for MEFA 7.2 are shown in FIGS. 9A-9F.

EXAMPLE 2

Production of NS3/4aPI

NS3/4aPI is a full-length NS3NS4a protein (amino acids 1027-1711) with mutations of the amino acids normally occurring at positions 1428 and 1429, to remove the putative autohydrolysis site of the protease. See, U.S. Pat. Nos. 6,630,298 and 6,632,601. This epitope has the sequence specified in FIGS. 13A through 13D and differs from the native sequence at positions 403 (amino acid 1428 of the HCV-1 full-length sequence) and 404 (amino acid 1429 of the HCV-1 full-length sequence). Specifically, the Thr normally occurring at position 1428 of the native sequence has been mutated to Pro and Ser which occurs at position 1429 of the native sequence has been mutated to Ee. The molecule was termed "NS3/4aPI." The molecule is also called "NS3NS4a PI" herein.

NS3/4aPI was produced and expressed in yeast as described in U.S. Pat. No. 6,632,601, incorporated herein by reference in its entirety. The presence of the NS3/4aPI protein was confirmed by Western blotting using a polyclonal antibody directed against the NS3 protease domain and a monoclonal antibody against the NS4 5-1-1 epitope. Protease activity of the NS3/4a epitope was demonstrated using MEFA 7.1 as a substrate, as described further below.

EXAMPLE 3

Proteolytic Cleavage Activity of NS3/4aPI on MEFA 7.1 and 7.2

Figure 14:
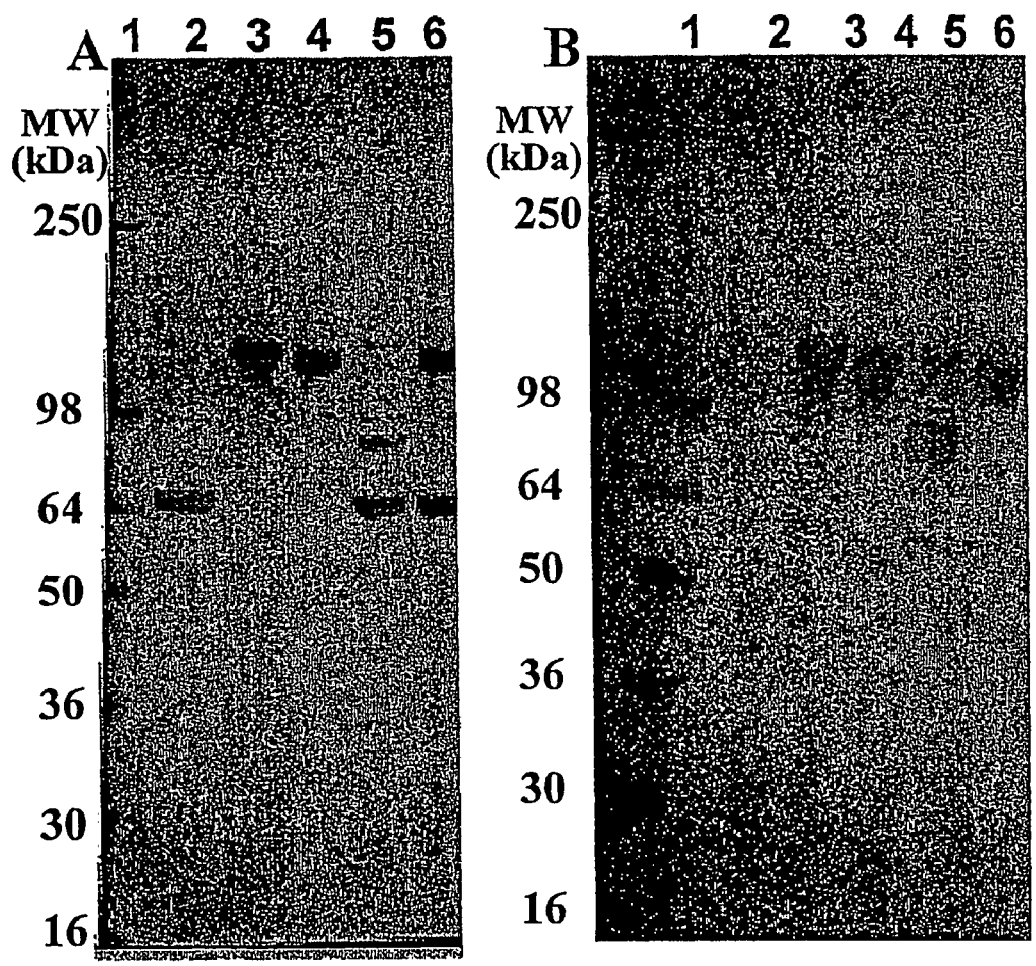
FIGS. 14A and 14B show the protease activity of NS3/4a PI and its effect on MEFA 7.1 and MEFA 7.2.

In order to confirm that the modified MEFA, MEFA 7.2, did not undergo proteolytic cleavage, the following experiment was conducted. MEFAs 7.1 and 7.2 were each incubated with NS3/4aPI, produced as described above, at room temperature for 30 minutes. Protein gel samples were prepared and run on 4-20% Tris-glycine SDS-PAGE and the gels were stained using Coomassie blue. Additionally, Western blots were conducted using an antibody against hSOD. As described above, both of MEFA 7.1 and 7.2 are fusions with hSOD. Results are shown in FIGS. 14A (SDS-PAGE) and 14B (Western blot). As can be seen, the NS3/4a cleaved MEFA 7.1 (lane 5, FIGS. 14A and 14B). MEFA 7.2, on the other hand, showed no degradation (lane 6, FIGS. 14A and 14B). Thus, NS3 proteolytic cleavage sites were successfully mutated in MEFA 7.2.

EXAMPLE 4

Monoclonal and Polyclonal Antibody Binding Assays

Monoclonal and polyclonal antibodies raised against HCV-specific recombinant core, E1, E2, NS3, NS4, and NS5 antigens were used to evaluate the antigenicity and epitope exposure of MEFA 7.1, MEFA 7.2 and NS3/4a PI. Purified MEFA or NS3/4a PI were diluted to optimal coating concentrations in PBS (pH 7.4) and were coated on Costar high binding plates (Corning Inc., Corning, N.Y.). Antibodies, either against linear epitopes or conformational epitopes, were diluted appropriately and added to the plate. After incubation at 37° C. for 1 hr, the plate was washed and incubated with goat-anti-mouse or goat-anti-rabbit IgG conjugated to horseradish peroxidase (HRP) for 1 hr at 37° C. Finally, a developing buffer containing $H_2O_2$ and the substrate o-phenylenediamine dihydrochloride (OPD) was added to the wells, and optical density (O.D.) at 492 and 620 nm was determined with a plate reader.

As shown in Table 3, each of the epitope-specific antibodies tested reacted with both MEFA 7.1 and MEFA 7.2, indicating (i) all the major epitopes on the MEFAs were exposed and thus accessible for detection, and (ii) amino acid mutations in MEFA 7.2 did not distort exposure of the linear epitopes.

EXAMPLE 5

Immunoassays Using MEFAs and NS3/4aPI

The C33c antigen of NS3 and the C22 core antigen are very immunogenic, and antibodies to C33c and C22 are found in early seroconversion panels (Chien et al., Proc. Natl. Acad. Sci. USA (1992) 89:10011-10015.) Thus, the performance of the antigens in immunoassays was studied using well-characterized, commercially available C33c and C22 panels of HCV-infected human blood samples to assess seroconversion sensitivity.

The PHV panels shown in the tables below were purchased from Boston Biomedica, Inc., West Bridgewater, Mass. (BBI); Bioclinical Partners, Franklin, Mass. (BCP); and North American Biologics, Inc., BocoRatan, Fla. (NABI). Assays were conducted as follows.

The HCV antigens were coated onto plates for immunoassays as follows. HCV coating buffer (50 mM $Na_3PO_4$ pH 7.0, 2 mM EDTA and 0.1% Chloroacetamide) was filtered through a 0.22 μL filter unit. The following reagents were then added sequentially to the HCV coating buffer and stirred after each addition: 2 μg/ml BSA-Sulfhydryl Modified, from a 10 mg/ml solution (Bayer Corp. Pentex, Kankakee, Ill.); 5 mM DTT from a 1 M solution (Sigma, St. Louis, Mo.); 0.45 μg/ml NS3/4a (protein concentration of 0.3 mg/ml); 0.375 μg/ml NS3.4aPI, MEFA 7.1 or MEFA 7.2 (protein concentration of 1 mg/ml). The final solution was stirred for 15 minutes at room temperature.

200 μl of the above solution was added to each well of a Costar high binding, flat bottom plate (Corning Inc., Corning, N.Y.) and the plates were incubated for 16 hours at room temperature. The plates were then washed with wash buffer (1×PBS, 0.1% TWEEN-20), tapped dry and 285 μl Ortho Post-Coat Buffer (1×PBS, pH 7.4, 1% BSA, 3% sucrose) added. The plates were incubated for at least 1 hour, tapped and dried overnight at 2-8° C. The plates were pouched with desiccants and stored at 4° C. for future use.

The HCV assay was conducted as follows. 200 μl of specimen diluent buffer (1 g/l casein, 100 mg/l recombinant human SOD, 1 g/l chloracetamide, 10 g/l BSA, 500 mg/l yeast extract, 0.366 g/l EDTA, 1.162 g/l $KPO_4$, 5 ml/l Tween-20, 29.22 g/l NaCl, 1.627 g/l $NaPO_4$, 1% SDS) was added to the coated plates. 20 μl of sample was then added. This was incubated at 37° C. for one hour. The plates were washed with wash buffer (1×PBS, pH 7.4, 0.1% Tween-20). 200 μl conjugate solution (a mouse anti-human IgG-HRP, such as mouse anti-human IgG-HRP diluted 1:22,000 in ORTHO HCV 3.0 ELISA Test System with Enhanced SAVe bulk conjugate diluent (Ortho-Clinical Diagnostics, Raritan, N.J.) was added and incubated for 60 minutes at 37° C. This was washed as above, and 200 μl substrate solution (1 OPD tablet/10 ml) was added. The OPD tablet contains o-phenylenediamine dihydrochloride and hydrogen peroxide for horse radish peroxidase reaction color development. This was incubated for 30 minutes at room temperature in the dark. The reaction was stopped by addition of 50 μl $4NH_2SO_4$ and the plates were read at 492 μm, relative to absorbance at 690 nm as control. The cutoff value was set at 0.6000+average signal (O.D.) of three negative control sera. Samples with S/CO values (O.D. of Signal over Cutoff ratio) equal or greater than 1.0 were considered to be positive, and those below 1.0 were considered to be negative.

Results using this immunoassay were compared to those obtained using commercial anti-HCV ELISA kits. In particular, the Abbott PRISM assay (Abbott Laboratories, Abbott Park, Ill.), is commercially available and is an antibody-based detection assay. The assay was performed using the manufacturer's instructions. The ORTHO HCV Version 3.0 ELISA Test System (HCV 3.0) (Ortho Clinical Diagnostics, Raritan, N.J.) is an antibody-based detection assay. The assay was conducted using the manufacturer's instructions. The Pasteur MONOLISA anti-HCV Plus Version 2 assay (Sanofi Diagnostics Pasteur, Marnes-la-Coquette, France) is an antibody-based detection assay. The assay was performed using the manufacturer's instructions.

Results are shown in Table 4. For the panels tested, MEFA 7.1 alone and MEFA 7.2 alone had very similar immunoreactivities, and both detected C22 type antibodies in seroconversion panel PHV 913 and C33c type antibodies in later bleeds of PHV 904 and PHV 914 panels (Table 4). NS3/4a PI, on the other hand, detected C33c type antibody in early bleeds of PHV 904 and PHV 914 panels (Table 4). Thus the combination of MEFA 7.1 or MEFA 7.2 and NS3/4a PI detected antibodies to C22 and C33c in early seroconversion samples. The detections were 2, and 12 days ahead of currently licensed Ortho HCV 3.0 and Abbott Prism assays in C33c and C22 type antibodies, respectively.

A total of 17 commercially available HCV seroconversion panels were tested. For anti-C33c type panels, the new antigens were 2 to 14 days ahead of both Ortho 3.0 and Abbott Prism in 9 out of 9 panels. For anti-C22 (core) type panels, the new antigens were 2 to 5 days ahead of Ortho HCV 3.0 in 3 out of 8 panels and Abbott Prism in 2 out 8 panels. The rest of the panels were equivalent. It should be emphasized that among the five anti-core panels showing equivalent performance between the new assay and the licensed assay, three panels had large bleed intervals between the shift from antibody negative to antibody positive: PHV 909 (28 days), PHV 911 (11 days), and SC-0010 (7 days). See, Table 6. Due to the length of the bleed intervals, it was difficult to compare seroconversion sensitivity between the new assay and the licensed assays using these three panels.

Genotype dilutional sensitivity was also compared using the antigens versus these commercially available assays. All three immunoassays were run simultaneously. As shown in Table 5, all the HCV genotypes 1-6 serially diluted were strongly detected with MEFA 7.1 and NS3/4a PI in the ELISA assay as compared to HCV 3.0 or Monolisa Ver. 2 Pasteur. In a separate experiment, genotype dilutional sensitivity using MEFA 7.1 or NS3/4a PI alone was compared.

In summary, the HCV antibody assay employing NS3/4a PI and MEFA 7.1 or MEFA 7.2 achieved greater sensitivity in both early seroconversion detection and in detection of varying genotype samples. The assay specificity matched the current licensed assays. Both antigens were highly purified and were produced in quantities suitable for product development. Once NS3/4a PI and MEFA 7.1 or MEFA 7.2 were coated on solid phase, they were remarkably stable. MEFA 7.1 has multiple NS3/4a PI protease cleavage sites, and it was degraded to several fragments during coating of the antigens (FIGS. 14A and 14B), although the immunoreactivity of the fusion protein appeared to be unaffected in these experiments (Tables 4 and 5). The improved MEFA 7.2 is intact in the presence of NS3/4a PI (FIGS. 14A and 14B), and the epitope exposure and immunoreactivity are very similar to MEFA 7.1 (Tables 3, 4 and 5). These data evidence that the increased detection sensitivity in early seroconversion samples is derived from multiple epitopes in MEFAs 7.1 and 7.2; the overall structure of the MEFA fusion protein itself, either being intact as in MEFA 7.2 or degraded as in MEFA 7.1, has little effect on early seroconversion detection. However, maintaining the integrity of the MEFA makes manufacturing the immunoassay components more efficient.

Accordingly, novel modified MEFAs and uses thereof in detection assays have been disclosed. From the foregoing, it will be appreciated that, although specific embodiments of the invention have been described herein for purposes of illustration, various modifications may be made without deviating from the spirit and scope thereof.

TABLE 3

ELISA ANALYSIS OF MEFA 7.1 AND MEFA 7.2 FOR EXPOSED HCV EPITOPES

| ANTIBODY | CLONE | OD WITH: MEFA 7.1 | MEFA 7.2 |
|---|---|---|---|
| MOUSE MONOCLONAL | | | |
| ANTI-CORE | 5H8/H6 | 0.830 | 0.745 |
| ANTI-CORE | 6H4/H8 | 0.742 | 0.807 |
| ANTI-5-1-1 | 6C10/D1 | 3.368 | 3.366 |
| ANTI-C33C | 4D1-1 | 3.142 | 3.237 |
| ANTI-NS5 | 3E1/F1 | 3.510 | 3.477 |
| NORMAL MOUSE SERUM | | 0.152 | 0.122 |
| RABBIT POLYCLONAL | | | |
| ANTI-E1 | | 1.649 | 1.223 |
| ANTI-E2 HVR1A CONSENSUS | | 1.784 | 1.783 |
| ANTI-E2 HVR1 + 2 CONSENSUS | | 1.302 | 1.441 |
| ANT-C22 | | 1.528 | 1.483 |
| ANTI-HELICASE | | 1.802 | 1.815 |
| ANTI-C100 | | 1.795 | 1.811 |
| NORMAL RABBIT SERUM | | 0.100 | 0.102 |

TABLE 4

Comparison of HCV seroconversion detection

| Seroconversion Panel | Bleed Day | MEFA 7.1 | MEFA 7.2 | NS3NS4a PI | MEFA 7.1 + NS3NS4a PI | MEFA 7.2 + NS3NS4a PI | Ortho HCV 3.0 | Abbott PRISM | Days Ahead[b] |
|---|---|---|---|---|---|---|---|---|---|
| PHV904-1 | 0 | 0.04 | 0.03 | 0.04 | 0.05 | 0.05 | 0.01 | 0.12 | 2 |
| PHV904-2 | 2 | 0.02 | 0.03 | 0.03 | 0.04 | 0.04 | 0.01 | 0.08 | |
| PHV904-3 | 7 | 0.33 | 0.23 | 1.83 | 1.79 | 2.47 | 0.33 | 0.51 | |
| PHV904-4 | 9 | 1.28 | 1.28 | 5.19 | 3.99 | 5.39 | 1.10 | 1.56 | |
| PHV904-5 | 14 | 2.17 | 2.75 | 5.76 | 5.14 | 5.70 | 3.27 | 3.54 | |
| PHV904-6 | 21 | 2.43 | 3.29 | 5.81 | 5.24 | 5.78 | 3.92 | 4.45 | |
| PHV904-7 | 23 | 2.73 | 3.57 | 6.31 | 6.36 | 6.31 | 4.26 | 4.69 | |
| PHV914-1 | 0 | 0.02 | 0.02 | 0.02 | 0.03 | 0.03 | 0.00 | 0.06 | 12 |
| PHV914-2 | 5 | 0.02 | 0.02 | 0.03 | 0.03 | 0.03 | 0.01 | 0.06 | |
| PHV914-3 | 9 | 0.03 | 0.02 | 0.07 | 0.11 | 0.14 | 0.01 | 0.06 | |
| PHV914-4 | 12 | 0.09 | 0.03 | 1.25 | 1.38 | 2.09 | 0.04 | 0.09 | |
| PHV914-5 | 16 | 0.44 | 0.28 | 3.22 | 2.80 | 4.28 | 0.33 | 0.47 | |
| PHV914-6 | 19 | 0.73 | 0.65 | 3.51 | 3.23 | 4.75 | 0.82 | 0.90 | |
| PHV914-7 | 24 | 2.00 | 2.23 | 4.69 | 4.72 | 5.52 | 3.10 | 2.41 | |
| PHV914-8 | 30 | 2.73 | 4.23 | 5.47 | 5.15 | 5.62 | 4.85 | 4.09 | |
| PHV914-9 | 33 | 2.95 | 4.64 | 5.65 | 5.36 | 5.66 | 4.85 | 4.52 | |
| PHV913-1 | 0 | 0.08 | 0.09 | 0.03 | 0.11 | 0.08 | 0.01 | 0.08 | >2 |
| PHV913-2 | 2 | 0.41 | 0.55 | 0.02 | 0.71 | 0.56 | 0.02 | 0.10 | |
| PHV913-3 | 7 | 1.62 | 2.47 | 0.07 | 2.66 | 2.90 | 0.43 | 0.50 | |
| PHV913-4 | 9 | 1.88 | 2.71 | 0.43 | 2.83 | 3.41 | 0.54 | 0.59 | |

AQ: K

[a] An S/CO greater than or equal to 1 is positive and is indicated by boldfacing. The cutoff value is calculated as described in materials and Methods.
[b] Number of days by which detection with NS3NS4a PI in combination with MEFA 7.1 or MEFA 7.2 precedes, detection by currently licensed assays.

TABLE 5

Comparison of HCV genotype dilution sensitivities

| Genotype | Dilution | NS3NS4a PI | MEFA 7.1 + NS3NS4a PI | MEFA 7.2 + NS3NS4a PI | Ortho HCV 3.0 | Monolisa Ver 2 Pasteur |
|---|---|---|---|---|---|---|
| 1b | 1:5,000 | 1.929 | 1.396 | 2.074 | 0.393 | 0.218 |
|  | 1:10,000 | 1.506 | 0.826 | 1.699 | 0.159 | 0.084 |
|  | 1:20,000 | 0.382 | 0.355 | 0.403 | 0.045 | 0.028 |
| 2a/c | 1:5,000 | 0.868 | 0.717 | 0.917 | 0.136 | 0.782 |
|  | 1:10,000 | 0.386 | 0.312 | 0.395 | 0.049 | 0.286 |
| 3a | 1:5,000 | 1.879 | 0.964 | 1.622 | 0.218 | 0.353 |
|  | 1:10,000 | 0.676 | 0.432 | 0.873 | 0.067 | 0.164 |
| 4a | 1:5,000 | 1.392 | 0.824 | 1.752 | 0.193 | 0.181 |
|  | 1:10,000 | 1.169 | 0.265 | 0.717 | 0.069 | 0.076 |
| 5a | 1:5,000 | 2.889 | 1.763 | 2.744 | 0.827 | 0.988 |
|  | 1:10,000 | 1.317 | 1.036 | 1.587 | 0.316 | 0.395 |
|  | 1:20,000 | 0.715 | 0.416 | 0.726 | 0.097 | 0.120 |

TABLE 5-continued

Comparison of HCV genotype dilution sensitivities

| | | | OD with: | | | |
|---|---|---|---|---|---|---|
| Genotype | Dilution | NS3NS4a PI | MEFA 7.1 + NS3NS4a PI | MEFA 7.2 + NS3NS4a PI | Ortho HCV 3.0 | Monolisa Ver 2 Pasteur |
| 6 | 1:5,000 | 2.978 | 2.455 | 3.224 | 2.863 | ND[a] |
|   | 1:10,000 | 2.841 | 0.984 | 1.192 | 0.380 | ND |

AQ: L
[a]ND, not determined

TABLE 6

Summary of study of 17 seroconversion panels

| Panel | Predominant antibody[a] | Genotype[a] | Days Ahead of Licensed Assay[b] |
|---|---|---|---|
| PHV 904 | NS3 | 1a | 2 |
| PHV 905 | NS3 | 1a | 7 |
| PHV 908 | NS3 | 3 | 8 |
| PHV 914 | NS3, core | 2b | 12 |
| HCV 6212 | NS3 | Unknown | 14 |
| HCV 6213 | NS3 | Unknown | 6 |
| HCV 6214 | NS3 | Unknown | 7 |
| HCV 6222 | NS3 | Unknown | 4 |
| SC-0040 | NS3 | 2b | 9 |
| PHV 913 | Core | 2b | >2 |
| PHV 907 | Core | 1b | 3 |
| PHV 909 | Core | 3 | 0[c] |
| PHV 910 | Core | 1b | 0 |
| PHV 911 | Core | 1a | 0[c] |
| PHV 912 | Core | 2b/3 | 0 |
| SC-0030 | Core | 1a | 5 |
| SC-0010 | Core | 3a | 0[c] |

[a]Data Provided by the HCV panel vendors.
[b]Comparison of assay sensitivity using MEFA 7.1 in combination with NS3NS4a PI versus a currently licensed assay, the Ortho HCV Version 3.0 ELISA Test System or Abbott PRISM.
[c]Bleed Intervals between the shift from antibody negative to antibody positive: 28 days for PHV 909, 11 days for PHV 911, and 7 days for the SC-0010 Panel.

We claim:

1. A modified hepatitis C virus (HCV) multiple epitope fusion antigen (MEFA), wherein said MEFA comprises at least one epitope from the HCV helicase domain that comprises an HCV NS3 proteolytic cleavage site, and at least one epitope from an NS4 region that comprises an HCV NS3 proteolytic cleavage site, wherein the HCV NS3 proteolytic cleavage sites present in said helicase domain epitope and said NS4 epitope are mutated, such that proteolytic cleavage of the modified MEFA by NS3 is inhibited relative to proteolytic cleavage of a corresponding MEFA lacking the mutations, and further wherein said modified MEFA reacts specifically with anti-HCV antibodies present in a biological sample from an HCV-infected individual, wherein the MEFA comprises a sequence of amino acids with at least 90% sequence identity to the contiguous sequence of amino acids depicted in SEQ ID NO:4, with the proviso that the amino acids at positions 466, 467, 493, 494, 695, 696, 721, 722, 770, 771, 819 and 820 of SEQ ID NO:4 are maintained.

2. The modified MEFA of claim 1, wherein said MEFA comprises the contiguous sequence of amino acids depicted in SEQ ID NO:4.

3. The modified MEFA of claim 1, wherein said MEFA consists of the contiguous sequence of amino acids depicted in SEQ ID NO:4.

4. An immunoassay solid support comprising the modified MEFA of claim 1.

5. The immunoassay solid support of claim 4, further comprising at least one HCV NS3/4a conformational epitope, wherein said NS3/4a conformational epitope reacts specifically with anti-HCV antibodies present in a biological sample from an HCV-infected individual.

6. The immunoassay solid support of claim 5, wherein said NS3/4a conformational epitope comprises the contiguous sequence of amino acids depicted in SEQ ID NO:6.

7. The immunoassay solid support of claim 5, wherein said NS3/4a conformational epitope consists of the contiguous sequence of amino acids depicted in SEQ ID NO:6.

8. A method of detecting hepatitis C virus (HCV) infection in a biological sample, said method comprising:
   (a) providing an immunoassay solid support according to claim 4;
   (b) combining a biological sample with said solid support under conditions which allow HCV antibodies, when present in the biological sample, to bind to said MEFA and said NS3/4a conformational epitope if present, to form a first immune complex;
   (c) adding to the solid support from step (b) under complex forming conditions a detectably labeled antibody, wherein said labeled antibody is reactive with said immune complex;
   (d) detecting second immune complexes formed between the detectably labeled antibody and the first immune complex, if any, as an indication of HCV infection in the biological sample.

9. An immunodiagnostic test kit comprising the immunoassay solid support of claim 4, and instructions for conducting the immunodiagnostic test.

10. A method of producing an immunoassay solid support, comprising:
    (a) providing a solid support; and
    (b) binding to the solid support at least one modified MEFA according to claim 1.

11. The method of claim 10, further comprising binding to the solid support at a discrete position an HCV NS3/4a conformational epitope, wherein the conformational epitope reacts specifically with anti-HCV antibodies present in a biological sample from an HCV-infected individual.

12. The method of claim 11, wherein said NS3/4a conformational epitope comprises the contiguous sequence of amino acids depicted in SEQ ID NO:6.

13. The method of claim 11, wherein said NS3/4a conformational epitope consists of the contiguous sequence of amino acids depicted in SEQ ID NO:6.

14. A polynucleotide comprising a coding sequence for the modified MEFA of claim 1.

15. A recombinant vector comprising:
    (a) a polynucleotide according to claim 14;
    (b) and control elements operably linked to said polynucleotide whereby the coding sequence can be transcribed and translated in a host cell.

16. A host cell transformed with the recombinant vector of claim 15.

17. A method of producing a recombinant MEFA comprising:
    (a) providing a population of host cells according to claim 16; and
    (b) culturing said population of cells under conditions whereby the multiple epitope fusion antigen encoded by the coding sequence present in said recombinant vector is expressed.

* * * * *